US009072706B2

(12) United States Patent
Hocking et al.

(10) Patent No.: US 9,072,706 B2
(45) Date of Patent: Jul. 7, 2015

(54) CHIMERIC FIBRONECTIN MATRIX MIMETICS AND USES THEROF

(75) Inventors: Denise Hocking, Rochester, NY (US); Daniel Roy, San Antonio, TX (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/994,179

(22) PCT Filed: Dec. 14, 2011

(86) PCT No.: PCT/US2011/064987

§ 371 (c)(1), (2), (4) Date: Sep. 6, 2013

(87) PCT Pub. No.: WO2012/082950

PCT Pub. Date: Jun. 21, 2012

(65) Prior Publication Data

US 2013/0337038 A1 Dec. 19, 2013

Related U.S. Application Data

(60) Provisional application No. 61/422,923, filed on Dec. 14, 2010.

(51) Int. Cl.

| | |
|---|---|
| ***A61K 38/00*** | (2006.01) |
| ***C07K 2/00*** | (2006.01) |
| ***C07K 4/00*** | (2006.01) |
| ***C07K 5/00*** | (2006.01) |
| ***C07K 7/00*** | (2006.01) |
| ***C07K 14/00*** | (2006.01) |
| ***C07K 16/00*** | (2006.01) |
| ***C07K 17/00*** | (2006.01) |
| ***A61K 38/18*** | (2006.01) |
| ***C07K 14/78*** | (2006.01) |
| ***A61K 38/17*** | (2006.01) |
| ***C07K 14/47*** | (2006.01) |
| *A61K 38/39* | (2006.01) |

(52) U.S. Cl.

CPC ................ *A61K 38/18* (2013.01); *A61K 38/00* (2013.01); *A61K 38/39* (2013.01); *C07K 14/78* (2013.01); *A61K 38/1709* (2013.01); *C07K 14/47* (2013.01)

(58) Field of Classification Search

None

See application file for complete search history.

(56) References Cited

U.S. PATENT DOCUMENTS

2005/0282747 A1 12/2005 Clark et al.

OTHER PUBLICATIONS

GenBank EJU06436-1, Aug. 23, 2012.*

Djarwanto et al, Screening of Fungi Capable of Degrading Lignocellulose from Plantation Forests (Pakistan Jownal of Biological Sciences 12 (9): 669-675, 2009).*

Gui et al. "Identification of the Heparin-binding Determinants within Fibronectin Repeat III, Role in Cell Spreading and Growth," J. Biol. Chem. 281(46):34816-34825 (2006).

Roy et al. "Development of Novel Fibronectin Matrix Mimetics for Use as Growth-promoting Adhesive Substrates," Upstate New York Biomedical Engineering Career Conference, Apr. 16, 2010 Abstract available at http://www.unybecconference.org/posters/list.

GenBank Accession No. P02751.4 for Fibronectin, http://www.ncbi.nlm.nih.gov/protein/300669710?sat+13&satkey=2854214 (Nov. 30, 2010).

Hocking et al. "A Cryptic Fragment from Fibronectin's III1 Module Localizes to Lipid Rafts and Stimulates Cell Growth and Contractility," J. Cell Biol. 158(1):175-184 (2002).

Vogel V., "Mechanotransduction Involving Multimodular Proteins: Converting Force into Biochemical Signals," Annu. Rev. Biophys. Biomol. Struct. 35:459-488 (2006).

Roy et al. "Chimeric Fibronectin Matrix Mimetic as a Functional Growth- and Migration-promoting Adhesive Substrate," Biomaterials 32(8):2077-2087 (Epub Dec. 24, 2010).

Roy et al. "Synthetic Matrix Mimetics Specify Integrin Adhesion and Direct Extracellular Matrix Assembly," http://abstracts.conferencestrategists.com/resources/1165/2805/pdf/TERMIS2011_0146.pdf (Oct. 2011).

Tang et al. "N-terminal and C-terminal Heparin-binding Domain Polypeptides Derived from Fibronectin Reduce Adhesion and Invasion of Liver Cancer Cells," BMC Cancer 10:552 (2010).

Gao et al. "Molecular Mechanisms of Cellular Mechanics," Phys. Chem. Chem. Phys. 8(32):3692-3706 (2006).

PCT International Search Report and Written Opinion for PCT/US2011/064987, completed Jun. 29, 2012.

Roy et al., "Development of Novel Fibronectin Matrix Mimetics for Use as Growth-Promoting Adhesive Substrates," Poster Presented at UNYBECC 2010, Rochester New York (Apr. 16, 2010).

Roy et al., "Engineered Matrix Mimetics Support Assembly of a Growth-Promoting Fibronectin Matrix," Poster Presented at Annual Meeting of Biomedical Engineering Society, Austin, Texas (Oct. 2010).

Roy et al., "Synthetic Matrix Mimetics Specify Integrin Adhesion and Direct Extracellular Matrix Assembly," TERMIS-NA Annual Meeting (Dec. 13, 2011).

Roy et al., "Engineered Matrix Mimetics Support Assembly of Two Distinct Forms of Fibronectin Matrix," Society for Biomaterials Annual Meeting (Apr. 15, 2011).

Supplementary European Search Report for Application No. 11848326.2 (Apr. 8, 2015).

Hocking et al., "Extracellular Matrix Fibronectin Mechanically Couples Skeletal Muscle Contraction with Local Vasodilation," Circ. Res. 102:372-379 (2008).

* cited by examiner

*Primary Examiner* — Marcela M Cordero Garcia
*Assistant Examiner* — Sergio Coffa
(74) *Attorney, Agent, or Firm* — LeClairRyan, a Professional Corporation

(57) ABSTRACT

The present invention is directed to recombinant fibronectin peptide mimetics and wound healing compositions containing the same. Other aspects of the present invention include wound healing dressings that comprise the wound healing composition of the present invention and a wound dressing material and methods of treating wounds using these compositions.

2 Claims, 19 Drawing Sheets

A.

B.

A.

B.

A.

C.

B.

D.

A.

B.

A.

B.

A.

B.

A.

B.

C.

A

B

C

D

CHIMERIC FIBRONECTIN MATRIX MIMETICS AND USES THEROF

This application is a national stage application under 35 U.S.C. §371 from PCT International Application No. PCT/US2011/064987, filed Dec. 14, 2011, which claims the benefit of U.S. Provisional Patent Application Ser. No. 61/422,923, filed Dec. 14, 2010, which is hereby incorporated by reference in its entirety.

This invention was made with government support under grant number R01GM081513 awarded by the National Institutes of Health. The government has certain rights in this invention.

FIELD OF THE INVENTION

The present invention relates to recombinant fibronectin peptide mimetics and wound healing compositions containing the same. The present invention further relates to methods of treating wounds using the recombinant fibronectin peptide mimetics or compositions of the present invention.

BACKGROUND OF THE INVENTION

Fibronectin is an abundant glycoprotein that is evolutionarily conserved and broadly distributed among vertebrates (Hynes et al., "Fibronectins: Multifunctional Modular Glycoproteins," *J. Cell Biol.* 95:369-377 (1982)). Soluble fibronectin is composed of two nearly identical subunits that are joined by disulfide bonds (Petersen et al., "Partial Primary Structure of Bovine Plasma Fibronectin: Three Types of Internal Homology," *Proc. Natl. Acad. Sci. U.S.A.* 80:137-141 (1983)). The primary structure of each subunit is organized into three types of repeating homologous units, termed types I, II, and III. Fibronectin type III repeats are found in a number of extracellular matrix (ECM) proteins and consist of two overlapping β sheets (Bork et al., "Proposed Acquisition of an Animal Protein Domain by Bacteria," *Proc. Natl. Acad. Sci. U.S.A.* 89(19):8990-8994 (1992) and Leahy et al., "Structure of a Fibronectin Type III Domain From Tenascin Phased by MAD Analysis of the Selenomethionyl Protein," *Science* 258:987-991 (1992)). Molecular modeling and atomic force microscopy studies predict that reversible unfolding of the type III repeats contributes to the remarkable elasticity of fibronectin, which may be extended up to six times its initial length without denaturation (Erickson, "Reversible Unfolding of Fibronectin Type III and Immunoglobulin Domains Provides the Structural Basis for Stretch and Elasticity of Titin and Fibronectin," *Proc. Natl. Acad. Sci.* 91:10114-10118 (1994) and Oberhauser et al., "The Mechanical Hierarchies of Fibronectin Observed with Single-Molecule AFM," *J. Mol. Biol.* 319(2):433-447 (2002)). In the ECM, fibronectin is organized as an extensive network of elongated, branching fibrils. The three-dimensional organization of ECM fibronectin likely arises from the ability of cells to repeatedly exert a mechanical force (Balaban et al., "Force and Focal Adhesion Assembly: A Close Relationship Studied Using Elastic Micropatterned Substrates," *Nat. Cell Biol.* 3(5):466-472 (2001)) on discrete regions of the protein (Erickson, "Reversible Unfolding of Fibronectin Type III and Immunoglobulin Domains Provides the Structural Basis for Stretch and Elasticity of Titin and Fibronectin," *Proc. Natl. Acad. Sci.* 91:10114-10118 (1994)) to facilitate the formation of fibronectin-fibronectin interactions (Mao et al., "Fibronectin FibrilloGenesis, a Cell-Mediated Matrix Assembly Process," *Matrix Biol.* 24(6):389-399 (2005)). As cells contact fibronectin fibrils, tractional forces induce additional conformational changes (Baneyx et al., "Coexisting Conformations of Fibronectin in Cell Culture Imaged Using Fluorescence Resonance Energy Transfer," *Proc. Natl. Acad. Sci. U.S.A.* 98(25):14464-14468 (2001)) that are necessary for both lateral growth and branching of the fibrils (Bultmann et al., "Fibronectin Fibrillogenesis Involves the Heparin II Binding Domain of Fibronectin," *J. Biol. Chem.* 273:2601-2609 (1998)).

The polymerization of fibronectin into the ECM is a cell-dependent process that is mediated by coordinated events involving the actin cytoskeleton and integrin receptors (Mao et al., "Fibronectin FibrilloGenesis, a Cell-Mediated Matrix Assembly Process," *Matrix Biol.* 24(6):389-399 (2005) and Magnusson et al., "Fibronectin: Structure, Assembly, and Cardiovascular Implications," *Arterio. Thromb. Vasc. Biol.* 18:1363-1370 (1998)). Most adherent cells, including epithelial cells, endothelial cells, fibroblasts, and smooth muscle cells, polymerize a fibrillar fibronectin matrix (Hynes et al., "Fibronectins: Multifunctional Modular Glycoproteins," *J. Cell Biol.* 95:369-377 (1982)). Recent studies have provided evidence that the interaction of cells with either the soluble or ECM form of fibronectin gives rise to distinct cellular phenotypes (Morla et al., "Superfibronectin is a Functionally Distinct Form of Fibronectin," *Nature* 367:193-196 (1994) and Hocking et al., "Stimulation of Integrin-Mediated Cell Contractility by Fibronectin Polymerization," *J. Biol. Chem.* 275:10673-10682 (2000)). ECM fibronectin stimulates cell spreading (Gui et al., "Identification of the Heparin-Binding Determinants Within Fibronectin Repeat III1: Role in Cell Spreading and Growth," *J. Biol. Chem.* 281(46):34816-34825 (2006)), growth (Sottile et al., "Fibronectin Matrix Assembly Enhances Adhesion-Dependent Cell Growth," *J. Cell Sci.* 111:2933-2943 (1998) and Sottile et al., "Fibronectin Matrix Assembly Stimulates Cell Growth by RGD-Dependent and -Independent Mechanisms," *J. Cell Sci.* 113:4287-4299 (2000)) and migration (Hocking et al., "Fibronectin Polymerization Regulates Small Airway Epithelial Cell Migration," *Am. J. Physiol. Lung Cell Mol. Physiol.* 285:L169-L179 (2003)), as well as collagen deposition (Sottile et al., "Fibronectin Polymerization Regulates the Composition and Stability of Extracellular Matrix Fibrils and Cell-Matrix Adhesions," *Mol. Biol. Cell* 13:3546-3559 (2002) and Velling et al., "Polymerization of Type I and III Collagens is Dependent on Fibronectin and Enhanced by Integrins Alpha 11beta 1 and Alpha 2beta 1," *J. Biol. Chem.* 277(40):37377-37381 (2002)) and organization (Hocking et al., "Stimulation of Integrin-Mediated Cell Contractility by Fibronectin Polymerization," *J. Biol. Chem.* 275:10673-10682 (2000)). Others have shown a role for fibronectin matrix assembly in the deposition of fibrinogen (Pereira et al., "The Incorporation of Fibrinogen Into Extracellular Matrix is Dependent on Active Assembly of a Fibronectin Matrix," *J. Cell Sci.* 115(Pt 3):609-617 (2002)), fibrillin (Sabatier et al., "Fibrillin Assembly Requires Fibronectin," *Mol. Biol. Cell* 20(3):846-858 (2009)), and tenascin C (Chung et al., "Binding of Tenascin-C to Soluble Fibronectin and Matrix Fibrils," *J. Biol. Chem.* 270:29012-29017 (1995)) into the ECM. Fibronectin matrix polymerization stimulates the formation of endothelial 'neovessels' in collagen lattices (Zhou et al., "Fibronectin Fibrillogenesis Regulates Three-Dimensional Neovessel Formation," *Genes. Dev.* 22(9):1231-1243 (2008)). Moreover, blocking fibronectin matrix polymerization inhibits cell growth (Sottile et al., "Fibronectin Matrix Assembly Enhances Adhesion-Dependent Cell Growth," *J. Cell Sci.* 111:2933-2943 (1998) and Mercurius et al., "Inhibition of Vascular Smooth Muscle Growth by Inhibition of Fibronectin Matrix Assembly," *Circ. Res.* 82:548-556 (1998)) and contractility (Hocking et al., "Stimulation of Integrin-Mediated Cell Contractility by Fibronectin Polymerization," *J. Biol. Chem.* 275:10673-10682 (2000)), alters actin organization (Hocking et al., "Inhibition of Fibronectin Matrix Assembly by the Heparin-Binding Domain of Vitronectin," *J. Biol. Chem.* 274:27257-27264 (1999)) and cell signaling (Bourdoulous et al., "Fibronectin Matrix Regulates Activation of RHO and CDC42 GTPases and Cell Cycle Progression," *J. Cell Biol.* 143:267-276 (1998)), and inhibits cell migration (Hocking et al., "Fibronectin Polymerization Regulates Small Airway Epithelial Cell Migration," *Am. J. Physiol. Lung Cell Mol. Physiol.* 285:L169-L179 (2003)). Together, these studies indicate that fibronectin matrix polymerization plays a key role in establishing the biologically-active extracellular environment required for proper tissue function.

Fibronectin matrix assembly is rapidly up-regulated following tissue injury, while reduced fibronectin matrix deposition is associated with abnormal wound repair (Hynes R O, FIBRONECTINS, (Springer-Verlag 1990)). Altered fibronectin matrix deposition is also associated with a large number of chronic diseases including asthma, liver cirrhosis, and atherosclerosis (Hynes R O, FIBRONECTINS, (Springer-Verlag 1990); Roberts C R, "Is Asthma a Fibrotic Disease?" *Chest* 107:111S-117S (1995); and Stenman et al., "Fibronectin and Atherosclerosis," *Acta. Medica. Scandinavia* (*Supplement*) 642:165-170 (1980)). Given the role of the fibronectin matrix in orchestrating ECM organization and in regulating cell and tissue responses critical for tissue repair, defective or diminished fibronectin matrix deposition by cells is likely to have profound effects on the ability of tissues to heal.

The present invention is directed to overcoming these and other deficiencies in the art.

SUMMARY OF THE INVENTION

A first aspect of the present invention is directed to a recombinant fibronectin peptide mimetic that comprises (i) at least a portion of the type III heparin-binding domain FNIII1H of fibronectin, where the portion comprises a heparin binding sequence, and (ii) at least a portion of the type III integrin-binding domain FNIII8-10 of fibronectin, where the portion comprises an integrin binding sequence and wherein the portion does not contain FNIII9 in its entirety.

Other aspects of the present invention are directed to wound healing compositions that comprise the recombinant fibronectin peptide mimetic of the present invention and a synthetic material, and wound healing dressings that comprise the wound healing composition of the present invention and a wound dressing material.

Another aspect of the present invention is directed to a method of treating a wound that involves providing a recombinant fibronectin peptide mimetic or a wound healing composition of the present invention, and applying the peptide mimetic or the composition to the wound under conditions effective to promote healing of the wound.

Several collagen-based dermal substitutes and lyophilized powders derived from porcine, bovine, or human skin are available for wound healing, and a synthetic matrix composed of RGD peptides and hyaluronic acid has shown promise in treating second-degree burn wounds. However, none of these compositions augment extracellular matrix fibronectin function. Described herein is the development of soluble, recombinant fibronectin matrix mimetics that rapidly stimulate cell spreading, migration, and growth upon topical application to tissues in vivo. The use of engineered fibronectin matrix analogs to 'jump-start' extracellular matrix fibronectin-mediated cell responses represents a new approach to enhancing cell and tissue function in chronic wounds. Recombinant fibronectin mimetics have several advantages over plasma fibronectin. Firstly, these recombinant mimetics do not require conversion into an "active" form like plasma fibronectin. Secondly, as small molecules, the mimetics are more likely to reach deeper into the wound than the full-length fibronectin. Third, the recombinant mimetics have fewer binding sites for interactions with other molecules, including proteases. Finally, the mimetics are not derived from human blood products, and as recombinant proteins, they are far easier and less expensive to produce on a large scale, and can be assured to be free of infective agents that can be transmitted via blood products.

The soluble recombinant fibronectin mimetics of the present invention are suitable additives to wound healing dressings, creams, hydrogels, etc. that will rapidly stimulate cell function and up-regulate tissue mechanics in tissue wounds, particularly, chronic, non-healing wounds and in damaged tissues. Addition of the fibronectin matrix mimetics to bioengineered scaffolds will enhance the cellular and mechanical properties of dermal substitutes for use with deep wounds and large surface burns. The use of the fibronectin matrix mimetics to promote proper extracellular matrix organization in burns may also reduce contractures and hypertrophic scars that can develop at these sites.

BRIEF DESCRIPTION OF THE DRAWINGS

FIG. 1A is a schematic representation of a fibronectin subunit and recombinant fibronectin fusion proteins. Relevant type III modules are numbered. GST represents the glutathione s-transferase tag used for peptide purification purposes. FNIII1H (1H) represent the heparin-binding, C-terminal fragment of FNIII1; FNIII8 (8), FNIII9 (9), and FNIII10 (10) represent the $8^{th}$, $9^{th}$, and $10^{th}$ fibronectin type III binding domains; and $ED_B$-C (or EDB) represents the corresponding C-terminal fragment of Extra domain-B. In FIG. 1B, aliquots (5 μg) of recombinant proteins were electrophoresed on a 10% SDS-polyacrylamide gel and stained with Coomassie Blue. Numbered lanes correspond to fusion protein identification numbers in FIG. 1A. Molecular mass markers are shown on left.

FIG. 2A is a panel of phase contrast images that were obtained at 24 h (top row) and 96 h (bottom row). Bar=100 μm. FIG. 2B is a chart quantifying cell number at 96 h as described in the Examples. Data are presented as mean absorbance of quadruplicate wells±SEM and represent 1 of 3 experiments. *Significantly greater than FN, $p<0.05$ (ANOVA).

In FIG. 3B, FN-null MEFs were seeded onto protein-coated wells ($1.5\times10^5$ cells/$cm^2$) and allowed to attach for 30 min. The number of adherent cells was determined as described infra in the Examples. Data are presented as mean absorbance of triplicate wells±SEM and represent 1 of 3 experiments. *Significantly different from GST/III1H,8-10, $p<0.05$ (ANOVA).

In FIGS. 4A and 4C, relative cell number was determined after 4 days. In FIGS. 4B and 4D, cells were allowed to adhere for 30 min and attached cell number was determined. Data are expressed as mean absorbance of quadruplicate wells±SEM and represent 1 of 3 experiments. *Significantly different from GST/III1H, 8-10, $p<0.05$ (ANOVA).

In FIG. 5A, relative cell number was determined after 4 days. In FIG. 5B, cells were allowed to adhere for 30 min and the number of attached cells was determined Data are expressed as mean absorbance of quadruplicate wells±SEM and represent 1 of 3 experiments. *Significantly different from GST/III1H,8-10, $p<0.05$ (ANOVA).

In FIG. 6A, cells were allowed to adhere for 30 min and attached cell number was determined. In FIG. 6B, relative cell number was determined after 4 days. Data are expressed as mean absorbance of triplicate wells (FIG. 6A) or quadruplicate wells (FIG. 6B) ±SEM and represent 1 of 3 experiments. *Significantly different from GST/III1H,8-10, $p<0.05$ (ANOVA).

In FIGS. 9A and 9B, * significantly different from FN, $p<0.05$. In FIG. 9C, * significantly different from GST/III1H,8,10, $p<0.05$ (ANOVA).

FIG. 13A is an immunoblot analysis of whole cell lysates using antibodies directed against fibronectin and α-tubulin Immunoblot represents 1 of 3 experiments each performed in duplicate wells. Fibronectin band intensities of immunoblots were quantified by densitometry and the results are shown in the graph of FIG. 13B. *Significantly different from GST/III1H,8-10, $p<0.05$. # Significantly greater than GST/III1H,8,10, $p<0.05$ (ANOVA). In FIG. 13C, Alexa$^{488}$-fibronectin accumulation was determined. Data are presented as mean fluorescence+/−SEM and represent 1 of 3 experiments. * Significantly different from GST/III1H,8-10, $p<0.05$. #Significantly greater than GST/III1H,8,10, $p<0.05$ (ANOVA).

In FIG. 14A, control wells received either FITC-collagen I only (+cell, −FN) or FITC collagen I in the absence of both cells and fibronectin (−cells, −FN). FITC-collagen I binding was quantified and data are presented as mean fluorescence intensity+/−SEM and represent 1 of 3 experiments performed in quadruplicate. *Significantly different from GST/III1H,8-10, $p<0.05$. # Significantly greater than GST/III1H,8,10, $p<0.05$ (ANOVA). In FIG. 14B, cells were processed for immunofluorescence microscopy and stained using an antibody against fibronectin. Images represent 1 of 3 experiments. Bar=10 μm. Four hours after seeding, cells were treated with fibronectin (10 μg/ml) and FITC-collagen I (10 μg/ml) in the presence of either R1R2 (250 nM) or FNIII11C (250 nM). FITC-collagen I was quantified after 20 h and the results are shown in FIG. 14C. Data are presented as mean fluorescence+/−SEM and represent 1 of 3 experiments performed in quadruplicate. *Significantly different from III11C treatment, $p<0.05$ (ANOVA).

In FIG. 16A, cells were processed for immunofluorescence microscopy and stained using antibodies against α5 integrin and vinculin. Images represent 1 of 3 experiments. Bar=10 μm. In FIG. 16B, cell surface proteins bound to the adhesive substrates were cross-linked using bis(sulfosuccinimidyl) suberate ($BS^3$). Unbound proteins were extracted and cross-linked. α5 integrins were analyzed by immunoblotting Immunoblot represents 1 of 3 experiments each performed in duplicate wells. α5 integrin band intensities of immunoblots were quantified and compiled from 3 separate experiments each performed in duplicate wells (FIG. 16C). *Significantly different from GST/III1H,8-10, $p<0.05$ (ANOVA).

In FIG. 18B, four hours after seeding, $Alexa^{488}$-labeled fibronectin (FN488; 10 μg/ml) was added to cells and incubated an additional 20 h. FN488 accumulation was quantified. Some wells received FN488 in the absence of cells (−cells) to assess fibronectin-substrate binding. Data are presented as mean fluorescence of quadruplicate wells+/−SEM and represent 1 of 3 experiments. *Significantly greater than all other substrates, $p<0.05$ (ANOVA).

FIG. 19B is a graph showing mean granulation tissue thickness quantified for 3 separate hematoxylin and eosin stained slides per mouse. Granulation tissue thickness was defined as the distance from the bottom of the epidermis to the top of the subcutaneous fat layer. Data are compiled from 4 separate experiments and are presented as the mean granulation tissue thickness+/−SEM. *Significantly different from GST, $p<0.05$ (ANOVA). #Significantly different from PBS, $p<0.05$ (ANOVA).

DETAILED DESCRIPTION OF THE INVENTION

The present invention relates generally to recombinant fibronectin matrix mimetics, wound healing compositions containing the recombinant mimetics, and their use in promoting wound healing and tissue regeneration.

A first aspect of the present invention relates to a recombinant fibronectin peptide mimetic that comprises (i) at least a portion of the type III heparin-binding domain FNIII1H of fibronectin, where the portion comprises a heparin binding sequence, and (ii) at least a portion of the type III integrin-binding domain FNIII8-10 of fibronectin, where the portion comprises an integrin binding sequence and wherein the portion does not contain FNIII9 in its entirety. As described herein, nucleic acid molecules encoding the recombinant fibronectin peptide mimetic of the present invention and expression vectors comprising these nucleic acid molecules are also encompassed by the present invention.

Figure 1A:
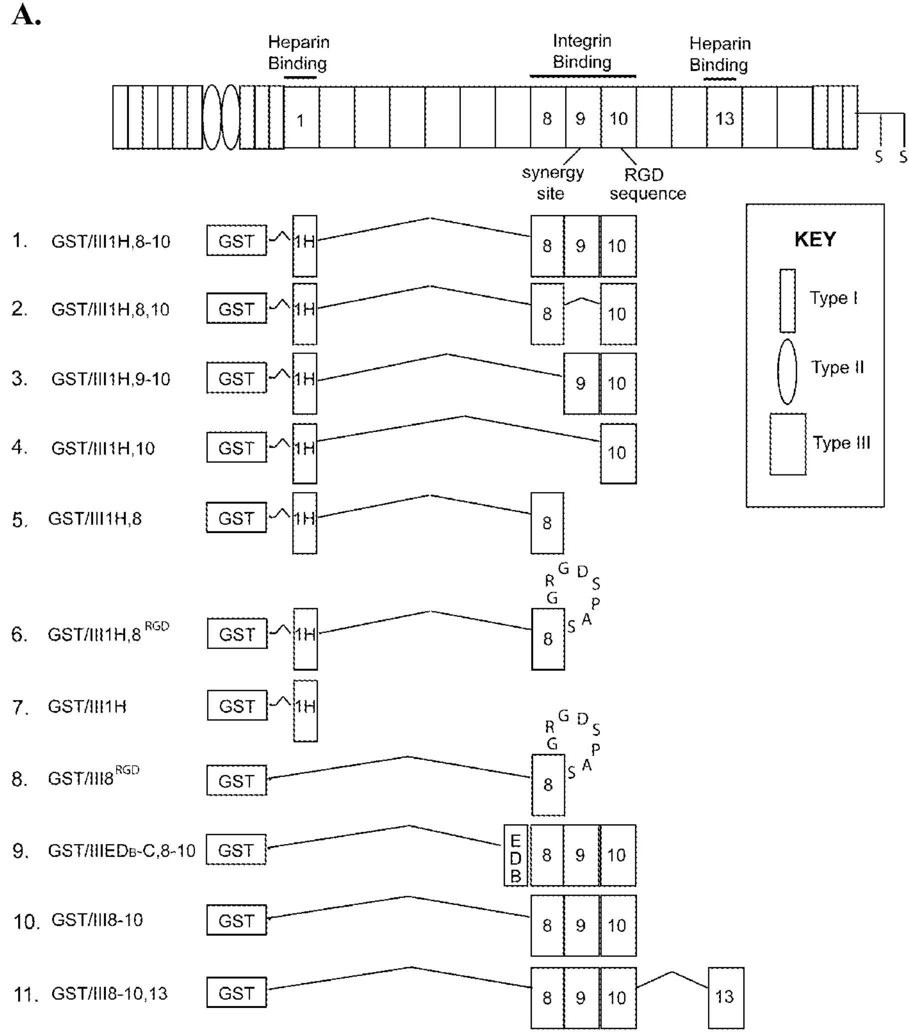
FIGS. 1A-1B show several illustrative fibronectin fusion proteins of the present invention.

Soluble fibronectin is composed of two nearly identical subunits that are joined by disulfide bonds. FIG. 1A shows a schematic representation of a fibronectin subunit. As shown, the primary structure of each subunit is organized into three types of repeating homologous units, termed types I, II, and III. The relevant type III modules (i.e., type III modules FNIII1, FNIII8, FNIII9, FNIII10, and FNIII13) in FIG. 1A are numbered. The composition of the various recombinant fibronectin peptide mimetics of the present invention are also shown below the schematic of the fibronectin subunit in FIG. 1A (numbered 1-11).

In describing the recombinant fibronectin peptide mimetics of the present invention, reference is made to the full-length human fibronectin amino acid sequence isoform 1 (UniProtKB/Swiss-Prot No. P02751, which is hereby incorporated by reference in its entirety) which is shown below as SEQ ID NO: 1. When describing the construction of the peptide mimetics of the present invention in the Examples, the amino acid residue positions referred to are in reference to the more mature fibronectin protein sequence that does not contain the 31-amino acid leader sequence. One of skill in the art readily appreciates, for example, that the FNIII1H domain comprises amino acid residues 628-704 of SEQ ID NO:1, but comprises amino acid residues 597-673 of the more mature fibronectin protein (i.e., the fibronectin protein without the 31-amino acid leader sequence).

```
                                                    SEQ ID NO: 1
Human Fibronectin
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380
```

-continued

```
Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815
```

-continued

```
Thr Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230
```

-continued

```
Phe Asp Asn Leu Ser Pro Gly Leu Glu Tyr Asn Val Ser Val Tyr
    1235                1240                1245

Thr Val Lys Asp Asp Lys Glu Ser Val Pro Ile Ser Asp Thr Ile
    1250                1255                1260

Ile Pro Ala Val Pro Pro Pro Thr Asp Leu Arg Phe Thr Asn Ile
    1265                1270                1275

Gly Pro Asp Thr Met Arg Val Thr Trp Ala Pro Pro Pro Ser Ile
    1280                1285                1290

Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635
```

-continued

```
Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
    1685                1690                1695

Thr Val Ser Val Val Ala Leu His Asp Asp Met Glu Ser Gln Pro
    1700                1705                1710

Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr
    1730                1735                1740

Pro Pro Asn Val Gln Leu Thr Gly Tyr Arg Val Arg Val Thr Pro
    1745                1750                1755

Lys Glu Lys Thr Gly Pro Met Lys Glu Ile Asn Leu Ala Pro Asp
    1760                1765                1770

Ser Ser Ser Val Val Val Ser Gly Leu Met Val Ala Thr Lys Tyr
    1775                1780                1785

Glu Val Ser Val Tyr Ala Leu Lys Asp Thr Leu Thr Ser Arg Pro
    1790                1795                1800

Ala Gln Gly Val Val Thr Thr Leu Glu Asn Val Ser Pro Pro Arg
    1805                1810                1815

Arg Ala Arg Val Thr Asp Ala Thr Glu Thr Thr Ile Thr Ile Ser
    1820                1825                1830

Trp Arg Thr Lys Thr Glu Thr Ile Thr Gly Phe Gln Val Asp Ala
    1835                1840                1845

Val Pro Ala Asn Gly Gln Thr Pro Ile Gln Arg Thr Ile Lys Pro
    1850                1855                1860

Asp Val Arg Ser Tyr Thr Ile Thr Gly Leu Gln Pro Gly Thr Asp
    1865                1870                1875

Tyr Lys Ile Tyr Leu Tyr Thr Leu Asn Asp Asn Ala Arg Ser Ser
    1880                1885                1890

Pro Val Val Ile Asp Ala Ser Thr Ala Ile Asp Ala Pro Ser Asn
    1895                1900                1905

Leu Arg Phe Leu Ala Thr Thr Pro Asn Ser Leu Leu Val Ser Trp
    1910                1915                1920

Gln Pro Pro Arg Ala Arg Ile Thr Gly Tyr Ile Ile Lys Tyr Glu
    1925                1930                1935

Lys Pro Gly Ser Pro Pro Arg Glu Val Val Pro Arg Pro Arg Pro
    1940                1945                1950

Gly Val Thr Glu Ala Thr Ile Thr Gly Leu Glu Pro Gly Thr Glu
    1955                1960                1965

Tyr Thr Ile Tyr Val Ile Ala Leu Lys Asn Asn Gln Lys Ser Glu
    1970                1975                1980

Pro Leu Ile Gly Arg Lys Lys Thr Asp Glu Leu Pro Gln Leu Val
    1985                1990                1995

Thr Leu Pro His Pro Asn Leu His Gly Pro Glu Ile Leu Asp Val
    2000                2005                2010

Pro Ser Thr Val Gln Lys Thr Pro Phe Val Thr His Pro Gly Tyr
    2015                2020                2025

Asp Thr Gly Asn Gly Ile Gln Leu Pro Gly Thr Ser Gly Gln Gln
    2030                2035                2040
```

-continued

```
Pro Ser Val Gly Gln Gln Met Ile Phe Glu Glu His Gly Phe Arg
    2045                2050                2055

Arg Thr Thr Pro Pro Thr Thr Ala Thr Pro Ile Arg His Arg Pro
    2060                2065                2070

Arg Pro Tyr Pro Pro Asn Val Gly Glu Glu Ile Gln Ile Gly His
    2075                2080                2085

Ile Pro Arg Glu Asp Val Asp Tyr His Leu Tyr Pro His Gly Pro
    2090                2095                2100

Gly Leu Asn Pro Asn Ala Ser Thr Gly Gln Glu Ala Leu Ser Gln
    2105                2110                2115

Thr Thr Ile Ser Trp Ala Pro Phe Gln Asp Thr Ser Glu Tyr Ile
    2120                2125                2130

Ile Ser Cys His Pro Val Gly Thr Asp Glu Glu Pro Leu Gln Phe
    2135                2140                2145

Arg Val Pro Gly Thr Ser Thr Ser Ala Thr Leu Thr Gly Leu Thr
    2150                2155                2160

Arg Gly Ala Thr Tyr Asn Val Ile Val Glu Ala Leu Lys Asp Gln
    2165                2170                2175

Gln Arg His Lys Val Arg Glu Glu Val Val Thr Val Gly Asn Ser
    2180                2185                2190

Val Asn Glu Gly Leu Asn Gln Pro Thr Asp Asp Ser Cys Phe Asp
    2195                2200                2205

Pro Tyr Thr Val Ser His Tyr Ala Val Gly Asp Glu Trp Glu Arg
    2210                2215                2220

Met Ser Glu Ser Gly Phe Lys Leu Leu Cys Gln Cys Leu Gly Phe
    2225                2230                2235

Gly Ser Gly His Phe Arg Cys Asp Ser Ser Arg Trp Cys His Asp
    2240                2245                2250

Asn Gly Val Asn Tyr Lys Ile Gly Glu Lys Trp Asp Arg Gln Gly
    2255                2260                2265

Glu Asn Gly Gln Met Met Ser Cys Thr Cys Leu Gly Asn Gly Lys
    2270                2275                2280

Gly Glu Phe Lys Cys Asp Pro His Glu Ala Thr Cys Tyr Asp Asp
    2285                2290                2295

Gly Lys Thr Tyr His Val Gly Glu Gln Trp Gln Lys Glu Tyr Leu
    2300                2305                2310

Gly Ala Ile Cys Ser Cys Thr Cys Phe Gly Gly Gln Arg Gly Trp
    2315                2320                2325

Arg Cys Asp Asn Cys Arg Arg Pro Gly Gly Glu Pro Ser Pro Glu
    2330                2335                2340

Gly Thr Thr Gly Gln Ser Tyr Asn Gln Tyr Ser Gln Arg Tyr His
    2345                2350                2355

Gln Arg Thr Asn Thr Asn Val Asn Cys Pro Ile Glu Cys Phe Met
    2360                2365                2370

Pro Leu Asp Val Gln Ala Asp Arg Glu Asp Ser Arg Glu
    2375                2380                2385
```

The corresponding nucleotide sequence encoding the full-length human fibronectin protein is provided as SEQ ID NO:2 below (NCBI Reference Sequence No. NM_212482.1, which is hereby incorporated by reference in its entirety).

SEQ ID NO: 2

```
Human Fibronectin
gcccgcgccg gctgtgctgc acagggggag gagagggaac cccaggcgcg agcgggaaga    60

ggggacctgc agccacaact tctctggtcc tctgcatccc ttctgtccct ccacccgtcc   120
```

-continued

```
ccttccccac cctctggccc ccaccttctt ggaggcgaca acccccggga ggcattagaa   180
gggatttttc ccgcaggttg cgaagggaag caaacttggt ggcaacttgc ctcccggtgc   240
gggcgtctct cccccaccgt ctcaacatgc ttaggggtcc ggggcccggg ctgctgctgc   300
tggccgtcca gtgcctgggg acagcggtgc cctccacggg agcctcgaag agcaagaggc   360
aggctcagca aatggttcag ccccagtccc cggtggctgt cagtcaaagc aagcccggtt   420
gttatgacaa tggaaaacac tatcagataa atcaacagtg ggagcggacc tacctaggca   480
atgcgttggt ttgtacttgt tatggaggaa gccgaggttt taactgcgag agtaaacctg   540
aagctgaaga gacttgcttt gacaagtaca ctgggaacac ttaccgagtg ggtgacactt   600
atgagcgtcc taaagactcc atgatctggg actgtacctg catcggggct gggcgaggga   660
gaataagctg taccatcgca aaccgctgcc atgaaggggg tcagtcctac aagattggtg   720
acacctggag gagaccacat gagactggtg gttacatgtt agagtgtgtg tgtcttggca   780
atggaaaagg agaatggacc tgcaagccca tagctgagaa gtgttttgat catgctgctg   840
ggacttccta tgtggtcgga gaaacgtggg agaagcccta ccaaggctgg atgatggtag   900
attgtacttg cctgggagaa ggcagcggac gcatcacttg cacttctaga aatagatgca   960
acgatcagga cacaaggaca tcctatagaa ttggagacac ctggagcaag aaggataacc  1020
gaggaaacct gctccagtgc atctgcacag gcaacggccg aggagagtgg aagtgtgaga  1080
ggcacacctc tgtgcagacc acatcgagcg gatctggccc cttcaccgat gttcgtgcag  1140
ctgtttacca accgcagcct cacccccagc ctcctcccta tggccactgt gtcacagaca  1200
gtggtgtggt ctactctgtg gggatgcagt ggctgaagac acaaggaaat aagcaaatgc  1260
tttgcacgtg cctgggcaac ggagtcagct gccaagagac agctgtaacc cagacttacg  1320
gtggcaactc aaatggagag ccatgtgtct taccattcac ctacaatggc aggacgttct  1380
actcctgcac cacagaaggg cgacaggacg gacatctttg gtgcagcaca acttcgaatt  1440
atgagcagga ccagaaatac tctttctgca cagaccacac tgctttggtt cagactcgag  1500
gaggaaattc caatggtgcc ttgtgccact tccccttcct atacaacaac cacaattaca  1560
ctgattgcac ttctgagggc agaagagaca acatgaagtg gtgtgggacc acacagaact  1620
atgatgccga ccagaagttt gggttctgcc ccatggctgc ccacgaggaa atctgcacaa  1680
ccaatgaagg ggtcatgtac cgcattggag atcagtggga taagcagcat gacatgggtc  1740
acatgatgag gtgcacgtgt gttgggaatg gtcgtgggga atggacatgc attgcctact  1800
cgcagcttcg agatcagtgc attgttgatg acatcactta caatgtgaac gacacattcc  1860
acaagcgtca tgaagagggg cacatgctga actgtacatg cttcggtcag ggtcggggca  1920
ggtggaagtg tgatcccgtc gaccaatgcc aggattcaga gactgggacg ttttatcaaa  1980
ttggagattc atgggagaag tatgtgcatg gtgtcagata ccagtgctac tgctatggcc  2040
gtggcattgg ggagtggcat tgccaacctt tacagaccta tccaagctca agtggtcctg  2100
tcgaagtatt tatcactgag actccgagtc agcccaactc ccaccccatc cagtggaatg  2160
caccacagcc atctcacatt tccaagtaca ttctcaggtg gagacctaaa aattctgtag  2220
gccgttggaa ggaagctacc ataccaggcc acttaaactc ctacaccatc aaaggcctga  2280
agcctggtgt ggtatacgag ggccagctca tcagcatcca gcagtacggc caccaagaag  2340
tgactcgctt tgacttcacc accaccagca ccagcacacc tgtgaccagc aacaccgtga  2400
caggagagac gactcccttt tctcctcttg tggccacttc tgaatctgtg accgaaatca  2460
cagccagtag ctttgtggtc tcctgggtct cagcttccga caccgtgtcg ggattccggg  2520
tggaatatga gctgagtgag gagggagatg agccacagta cctggatctt ccaagcacag  2580
```

-continued

```
ccacttctgt gaacatccct gacctgcttc ctggccgaaa atacattgta aatgtctatc  2640
agatatctga ggatggggag cagagtttga tcctgtctac ttcacaaaca acagcgcctg  2700
atgcccctcc tgacccgact gtggaccaag ttgatgacac ctcaattgtt gttcgctgga  2760
gcagacccca ggctcccatc acagggtaca gaatagtcta ttcgccatca gtagaaggta  2820
gcagcacaga actcaacctt cctgaaactg caaactccgt caccctcagt gacttgcaac  2880
ctggtgttca gtataacatc actatctatg ctgtggaaga aaatcaagaa agtacacctg  2940
ttgtcattca acaagaaacc actggcaccc cacgctcaga tacagtgccc tctcccaggg  3000
acctgcagtt tgtggaagtg acagacgtga aggtcaccat catgtggaca ccgcctgaga  3060
gtgcagtgac cggctaccgt gtggatgtga tccccgtcaa cctgcctggc gagcacgggc  3120
agaggctgcc catcagcagg aacacctttg cagaagtcac cgggctgtcc cctggggtca  3180
cctattactt caaagtcttt gcagtgagcc atgggaggga gagcaagcct ctgactgctc  3240
aacagacaac caaactggat gctcccacta acctccagtt tgtcaatgaa actgattcta  3300
ctgtcctggt gagatggact ccacctcggg cccagataac aggataccga ctgaccgtgg  3360
gccttacccg aagaggacag cccaggcagt acaatgtggg tccctctgtc tccaagtacc  3420
cactgaggaa tctgcagcct gcatctgagt acaccgtatc cctcgtggcc ataaagggca  3480
accaagagag ccccaaagcc actggagtct ttaccacact gcagcctggg agctctattc  3540
caccttacaa caccgaggtg actgagacca ccattgtgat cacatggacg cctgctccaa  3600
gaattggttt taagctgggt gtacgaccaa gccagggagg agaggcacca cgagaagtga  3660
cttcagactc aggaagcatc gttgtgtccg gcttgactcc aggagtagaa tacgtctaca  3720
ccatccaagt cctgagagat ggacaggaaa gagatgcgcc aattgtaaac aaagtggtga  3780
caccattgtc tccaccaaca aacttgcatc tggaggcaaa ccctgacact ggagtgctca  3840
cagtctcctg ggagaggagc accacccag acattactgg ttatagaatt accacaaccc  3900
ctacaaacgg ccagcaggga aattctttgg aagaagtggt ccatgctgat cagagctcct  3960
gcacttttga taacctgagt cccggcctgg agtacaatgt cagtgtttac actgtcaagg  4020
atgacaagga aagtgtccct atctctgata ccatcatccc agaggtgccc caactcactg  4080
acctaagctt tgttgatata accgattcaa gcatcggcct gaggtggacc ccgctaaact  4140
cttccaccat tattgggtac cgcatcacag tagttgcggc aggagaaggt atccctattt  4200
ttgaagattt tgtggactcc tcagtaggat actacacagt cacagggctg gagccgggca  4260
ttgactatga tatcagcgtt atcactctca ttaatggcgg cgagagtgcc cctactacac  4320
tgacacaaca aacggctgtt cctcctccca ctgacctgcg attcaccaac attggtccag  4380
acaccatgcg tgtcacctgg gctccacccc catccattga tttaaccaac ttcctggtgc  4440
gttactcacc tgtgaaaaat gaggaagatg ttgcagagtt gtcaatttct ccttcagaca  4500
atgcagtggt cttaacaaat ctcctgcctg gtacagaata tgtagtgagt gtctccagtg  4560
tctacgaaca acatgagagc acacctctta gaggaagaca gaaaacaggt cttgattccc  4620
caactggcat tgacttttct gatattactg ccaactcttt tactgtgcac tggattgctc  4680
ctcgagccac catcactggc tacaggatcc gccatcatcc cgagcacttc agtgggagac  4740
ctcgagaaga tcgggtgccc cactctcgga attccatcac cctcaccaac ctcactccag  4800
gcacagagta tgtggtcagc atcgttgctc ttaatggcag agaggaaagt cccttattga  4860
ttggccaaca atcaacagtt tctgatgttc cgagggacct ggaagttgtt gctgcgaccc  4920
ccaccagcct actgatcagc tgggatgctc ctgctgtcac agtgagatat tacaggatca  4980
cttacggaga gacaggagga aatagccctg tccaggagtt cactgtgcct gggagcaagt  5040
```

-continued

```
ctacagctac catcagcggc cttaaacctg gagttgatta taccatcact gtgtatgctg  5100
tcactggccg tggagacagc cccgcaagca gcaagccaat ttccattaat taccgaacag  5160
aaattgacaa accatcccag atgcaagtga ccgatgttca ggacaacagc attagtgtca  5220
agtggctgcc ttcaagttcc cctgttactg gttacagagt aaccaccact cccaaaaatg  5280
gaccaggacc aacaaaaact aaaactgcag gtccagatca aacagaaatg actattgaag  5340
gcttgcagcc cacagtggag tatgtggtta gtgtctatgc tcagaatcca agcggagaga  5400
gtcagcctct ggttcagact gcagtaacca acattgatcg ccctaaagga ctggcattca  5460
ctgatgtgga tgtcgattcc atcaaaattg cttgggaaag cccacagggg caagtttcca  5520
ggtacagggt gacctactcg agccctgagg atggaatcca tgagctattc cctgcacctg  5580
atggtgaaga agacactgca gagctgcaag gcctcagacc gggttctgag tacacagtca  5640
gtgtggttgc cttgcacgat gatatggaga gccagcccct gattggaacc cagtccacag  5700
ctattcctgc accaactgac ctgaagttca ctcaggtcac acccacaagc ctgagcgccc  5760
agtggacacc acccaatgtt cagctcactg gatatcgagt gcgggtgacc cccaaggaga  5820
agaccggacc aatgaaagaa atcaaccttg ctcctgacag ctcatccgtg gttgtatcag  5880
gacttatggt ggccaccaaa tatgaagtga gtgtctatgc tcttaaggac actttgacaa  5940
gcagaccagc tcagggagtt gtcaccactc tggagaatgt cagcccacca agaagggctc  6000
gtgtgacaga tgctactgag accaccatca ccattagctg gagaaccaag actgagacga  6060
tcactggctt ccaagttgat gccgttccag ccaatggcca gactccaatc cagagaacca  6120
tcaagccaga tgtcagaagc tacaccatca caggtttaca accaggcact gactacaaga  6180
tctacctgta caccttgaat gacaatgctc ggagctcccc tgtggtcatc gacgcctcca  6240
ctgccattga tgcaccatcc aacctgcgtt tcctggccac cacacccaat tccttgctgg  6300
tatcatggca gccgccacgt gccaggatta ccggctacat catcaagtat gagaagcctg  6360
ggtctcctcc cagagaagtg gtccctcggc cccgccctgg tgtcacagag gctactatta  6420
ctggcctgga accgggaacc gaatatacaa tttatgtcat tgccctgaag aataatcaga  6480
agagcgagcc cctgattgga aggaaaaaga cagacgagct tccccaactg gcaacccttc  6540
cacaccccaa tcttcatgga ccagagatct tggatgttcc ttccacagtt caaaagaccc  6600
ctttcgtcac ccaccctggg tatgacactg gaaatggtat tcagcttcct ggcacttctg  6660
gtcagcaacc cagtgttggg caacaaatga tctttgagga acatggtttt aggcggacca  6720
caccgcccac aacggccacc cccataaggc ataggccaag accataccccg ccgaatgtag  6780
gtgaggaaat ccaaattggt cacatcccca gggaagatgt agactatcac ctgtacccac  6840
acggtccggg actcaatcca aatgcctcca caggacaaga agctctctct cagacaacca  6900
tctcatgggc cccattccag gacacttctg agtacatcat ttcatgtcat cctgttggca  6960
ctgatgaaga acccttacag ttcagggttc ctggaacttc taccagtgcc actctgacag  7020
gcctcaccag aggtgccacc tacaacatca tagtggaggc actgaaagac cagcagaggc  7080
ataaggttcg ggaagaggtt gttaccgtgg gcaactctgt caacgaaggc ttgaaccaac  7140
ctacggatga ctcgtgcttt gaccccctaca cagtttccca ttatgccgtt ggagatgagt  7200
gggaacgaat gtctgaatca ggctttaaac tgttgtgcca gtgcttaggc tttggaagtg  7260
gtcatttcag atgtgattca tctagatggt gccatgacaa tggtgtgaac tacaagattg  7320
gagagaagtg ggaccgtcag ggagaaaatg gccagatgat gagctgcaca tgtcttggga  7380
acggaaaagg agaattcaag tgtgaccctc atgaggcaac gtgttatgat gatgggaaga  7440
cataccacgt aggagaacag tggcagaagg aatatctcgg tgccatttgc tcctgcacat  7500
```

-continued

```
gctttggagg ccagcggggc tggcgctgtg acaactgccg cagacctggg ggtgaaccca  7560

gtcccgaagg cactactggc cagtcctaca accagtattc tcagagatac catcagagaa  7620

caaacactaa tgttaattgc ccaattgagt gcttcatgcc tttagatgta caggctgaca  7680

gagaagattc ccgagagtaa atcatctttc caatccagag gaacaagcat gtctctctgc  7740

caagatccat ctaaactgga gtgatgttag cagacccagc ttagagttct tctttctttc  7800

ttaagccctt tgctctggag gaagttctcc agcttcagct caactcacag cttctccaag  7860

catcaccctg ggagtttcct gagggttttc tcataaatga gggctgcaca ttgcctgttc  7920

tgcttcgaag tattcaatac cgctcagtat tttaaatgaa gtgattctaa gatttggttt  7980

gggatcaata ggaaagcata tgcagccaac caagatgcaa atgttttgaa atgatatgac  8040

caaaatttta agtaggaaag tcacccaaac acttctgctt tcacttaagt gtctggcccg  8100

caatactgta ggaacaagca tgatcttgtt actgtgatat tttaaatatc cacagtactc  8160

actttttcca aatgatccta gtaattgcct agaaatatct ttctcttacc tgttatttat  8220

caatttttcc cagtattttt atacggaaaa aattgtattg aaaacactta gtatgcagtt  8280

gataagagga atttggtata attatggtgg gtgattattt tttatactgt atgtgccaaa  8340

gctttactac tgtggaaaga caactgtttt aataaaagat ttacattcca caacttgaag  8400

ttcatctatt tgatataaga caccttcggg ggaaataatt cctgtgaata ttctttttca  8460

attcagcaaa catttgaaaa tctatgatgt gcaagtctaa ttgttgattt cagtacaaga  8520

ttttctaaat cagttgctac aaaaactgat tggtttttgt cacttcatct cttcactaat  8580

ggagatagct ttacactttc tgctttaata gatttaagtg gaccccaata tttattaaaa  8640

ttgctagttt accgttcaga agtataatag aaataatctt tagttgctct tttctaacca  8700

ttgtaattct tcccttcttc cctccacctt tccttcattg aataaacctc tgttcaaaga  8760

gattgcctgc aagggaaata aaaatgacta agatattaaa aaaaaaaaaa aaaaa       8815
```

In accordance with this aspect of the invention, the recombinant fibronectin peptide mimetic comprises at least a portion of the type III heparin binding domain FNIII1H. FNIII1H is the C-terminal fragment of FNIII1 that extends from amino acid residues 628-704 of SEQ ID NO:1.

The at least a portion of the FNIII1H domain comprises, at a minimum, a heparin binding sequence having an amino acid sequence of Xaa-Trp-Xaa-Pro-Xaa (SEQ ID NO: 12), where Xaa is any charged amino acid. In one embodiment of the present invention, this portion of the recombinant fibronectin peptide mimetic contains more than one heparin binding sequences. In accordance with this embodiment, multiple heparin binding sequences may be the same (i.e., repeating sequence), or comprise different heparin binding sequences.

In one embodiment of the present invention, the heparin binding sequence has an amino acid sequence of Arg-Trp-Arg-Pro-Lys (SEQ ID NO:13), corresponding to amino acids 644-648 of the full-length human fibronectin amino acid sequence (SEQ ID NO: 1) (or amino acid residues 613-617 of the mature fibronectin protein lacking the 31-amino acid leader sequence). Other embodiments include a heparin binding sequence of SEQ ID NO:12 having one or more additional amino acid residues at either its N-terminal side or its C-terminal side, or both.

In another embodiment of the present invention, the at least a portion of the FNIII1H comprises an amino acid sequence corresponding to amino acids 628-704 of SEQ ID NO: 1.

The at least a portion of the type III integrin binding domain of the recombinant fibronectin peptide mimetic of the present invention comprises, at a minimum, an integrin binding sequence. In one embodiment of the present invention, this portion of the recombinant fibronectin peptide mimetic comprises more than one integrin binding sequence. In accordance with this embodiment, the multiple integrin binding sequences may be the same (i.e., repeating sequences) or different sequences. This portion can be linked directly to the type III heparin binding domain portion. Alternatively, one or more linker amino acid residues can be incorporated at the junction of these portions. Suitable linker amino acids include, with out limitation, one or more serine or glycine residues.

The at least a portion of the type III integrin binding domain can be derived from the FNIII8 (amino acid residues 1266-1356 of SEQ ID NO:1), FNIII9 (amino acid residues 1357-1446 of SEQ ID NO:1), or FNIII10 (amino acids 1447-1536 of SEQ ID NO: 1) modules alone or in any combination. In one embodiment of the present invention, this portion does not include the FNIII9 module in its entirety when the FNIII8 and FNIII10 modules are incorporated in their entirety. In accordance with this embodiment of the present invention, this portion may comprise less than 85 amino acid residues of the FNIII9 module, less than 75 amino acid residues of the FNIII9 module, less than 65 amino acid residues of the FNIII9 module, less than 55 amino acid residues of the FNIII9 module, less than 45 amino acid residues of the FNIII9 module, less than 35 amino acid residues of the FNIII9 module, less than 25 amino acid residues of the FNIII9 module, less than 15 amino acid residues of the FNIII9 module, less than 5 amino acid residues of the FNIII9 module, or no amino acid residue of the FNIII9 module.

In one embodiment of the present invention, the portion of the type III integrin binding domain comprises the FNIII8 module, or a portion thereof, linked to the FNIII10 module, or a portion thereof. Consistent with this embodiment of the present invention, the portion of the type III integrin binding domain has an amino acid sequence corresponding to amino acids 1266-1356 of SEQ ID NO:1 (FNIII8) linked to amino acids 1447-1536 of SEQ ID NO: 1 (FNIII10). As described infra, the amino acid residues of the FNIII8 module can be linked directly to the FNIII10 module (i.e., via an inframe gene fusion). Alternatively, linker amino acid residues can be incorporated into the junction. Suitable linker amino acid residues include one or more serine and/or glycine amino acid residues.

The three-dimensional structure of FnIII has been determined by NMR (Main et al., "The Three-Dimensional Structure of the Tenth Type III Module of Fibronectin: An Insight into RGD-Mediated Interactions," *Cell* 71:671-678 (1992), which is hereby incorporated by reference in its entirety) and by X-ray crystallography (Leahy et al, "Structure of a Fibronectin Type III Domain From Tenascin Phased by MAD Analysis of the Selenomethionlyl Protein," *Science* 258:987-991 (1992); Dickinson et al, "Crystal Structure of the Tenth Type III Cell Adhesion Module of Human Fibronectin," *J. Mol. Biol.* 236: 1079-1092 (1994), which are hereby incorporated by reference in their entirety).

Both the eighth and tenth type III modules of fibronectin have a fold similar to that of immunoglobulin domains, with seven β strands forming two antiparallel β sheets, which pack against each other (Main et al, "The Three-Dimensional Structure of the Tenth Type III Module of Fibronectin: An Insight into RGD-Mediated Interactions," *Cell* 71:671-678 (1992); Craig et al., "Comparison of the Early Stages of Forced Unfolding for Fibronectin Type III Modules," *Proc. Nat'l Acad. Sci. U.S.A.* 98(10):5590-5595 (2001), each of which is hereby incorporated by reference in its entirety). One β sheet contains the residues of the A, B, and E strands, and the other β sheet contains the residues of the C, D, F, and G strands. The majority of the conserved residues contribute to the hydrophobic core, with the invariant hydrophobic residues Trp-22 and Tyr-68 lying toward the N-terminal and C-terminal ends of the core, respectively. The β strands are much less flexible and appear to provide a rigid framework upon which functional, flexible loops can be built. The topology is similar to that of immunoglobulin C domains. As a result, this molecule has been proven to be a powerful and versatile molecular scaffold for the generation of binding proteins, termed "monobodies," with affinities in the nanomolar range (Koide et al, "Monobodies: Antibody Mimics Based on the Scaffold of the Fibronectin Type III Domain," *Methods Mol Biol.* 352:95-109 (2007); Richards et al, "Engineered Fibronectin Type III Domain with a RGDWXE Sequence Binds with Enhanced Affinity and Specificity to Human $\alpha_v\beta_3$ Integrin," *J Mol Biol.* 326(5): 1475-88 (2003), which are hereby incorporated by reference in their entirety). The β-strand domain sequences A, B, C, D, E, F, and G of the type III modules of fibronectin is conserved among mammals generally.

The FNIII scaffolds are very stable and easy to produce in large quantities suitable for recombinant expression and purification. Thus, the fibronectin peptide mimetic of the present invention can include FNIII8 or FNIII10-derived polypeptides that include at least two β-strand domain sequences with a loop region sequence linked between adjacent β-strand domain sequences and optionally, an N-terminal tail of at least about 2 amino acids, a C-terminal tail of at least about 2 amino acids, or both. The fibronectin peptide mimetic of the present invention can include the β-strand domain sequences A, B, C, D, E, F, and G of a wild-type mammalian fibronectin Fn3 domain with loop region sequences AB, BC, CD, DE, EF, and FG linked between adjacent β-strand domain sequences. The fibronectin peptide mimetic also optionally includes an N-terminal tail of at least about 2 amino acids, a C-terminal tail of at least about 2 amino acids, or both.

In certain embodiments, at least one loop region sequence, the N-terminal tail, or the C-terminal tail, or combinations thereof, comprises a modified amino acid sequence which varies by deletion, insertion, or replacement of at least two amino acids from a corresponding loop region in the wild-type mammalian FNIII domain of fibronectin, and affords a functional amino acid sequence that enhances the wound healing capability of the larger peptide molecule.

One example of this is the modification of a loop region of the FNIII8 domain to include an integrin-binding sequence (e.g., RGD) derived from the FNIII10 domain as described in the accompanying examples.

In certain embodiments, it may be desirable to insert multiple heparin-binding domains or integrin-binding sequences into multiple (i.e., different) loops of the FNIII domains present in the fibronectin peptide mimetic of the present invention.

An exemplary fibronectin peptide mimetic of the present invention comprising the FNIII8 and FNIII10 modules is FNIII1H,8,10, having an amino acid sequence of SEQ ID NO: 3 as shown below (also shown schematically as peptide mimetic #2 in FIG. 1A). This sequence corresponds to amino acid residues 628-704, 1266-1356, and 1447-1536 of the full-length human fibronectin (SEQ ID NO:1).

```
                                                SEQ ID NO: 3
FNIII1H, 8, 10
Ile Gln Trp Asn Ala Pro Gln Pro Ser His Ile Ser Lys Tyr Ile Leu
1               5                   10                  15

Arg Trp Arg Pro Lys Asn Ser Val Gly Arg Trp Lys Glu Ala Thr Ile
            20                  25                  30

Pro Gly His Leu Asn Ser Tyr Thr Ile Lys Gly Leu Lys Pro Gly Val
        35                  40                  45

Val Tyr Glu Gly Gln Leu Ile Ser Ile Gln Gln Tyr Gly His Gln Glu
    50                  55                  60

Val Thr Arg Phe Asp Phe Thr Thr Thr Ser Thr Ser Thr Ala Val Pro
65                  70                  75                  80

Pro Pro Thr Asp Leu Arg Phe Thr Asn Ile Gly Pro Asp Thr Met Arg
                85                  90                  95
```

-continued

```
Val Thr Trp Ala Pro Pro Pro Ser Ile Asp Leu Thr Asn Phe Leu Val
            100                 105                 110

Arg Tyr Ser Pro Val Lys Asn Glu Glu Asp Val Ala Glu Leu Ser Ile
        115                 120                 125

Ser Pro Ser Asp Asn Ala Val Val Leu Thr Asn Leu Leu Pro Gly Thr
    130                 135                 140

Glu Tyr Val Val Ser Val Ser Ser Val Tyr Glu Gln His Glu Ser Thr
145                 150                 155                 160

Pro Leu Arg Gly Arg Gln Lys Thr Val Ser Asp Val Pro Arg Asp Leu
                165                 170                 175

Glu Val Val Ala Ala Thr Pro Thr Ser Leu Leu Ile Ser Trp Asp Ala
            180                 185                 190

Pro Ala Val Thr Val Arg Tyr Tyr Arg Ile Thr Tyr Gly Glu Thr Gly
        195                 200                 205

Gly Asn Ser Pro Val Gln Glu Phe Thr Val Pro Gly Ser Lys Ser Thr
    210                 215                 220

Ala Thr Ile Ser Gly Leu Lys Pro Gly Val Asp Tyr Thr Ile Thr Val
225                 230                 235                 240

Tyr Ala Val Thr Gly Arg Gly Asp Ser Pro Ala Ser Ser Lys Pro Ile
                245                 250                 255

Ser Ile
```

Nucleic acid molecules encoding FNIII1H,8,10 comprise a nucleotide sequence of SEQ ID NO: 4 or SEQ ID NO: 5 as shown below. The nucleotide sequence of SEQ ID NO:4 encodes glycine and serine amino acid residues linking the FNII1H and FNIII8 modules, i.e., it encodes a sequence that differs from SEQ ID NO: 3 by the addition of two glycine/serine residues between the threonine and alanine residues at positions 77 and 78. The linker codons are shown in bold in SEQ ID NO:4. No amino acid linkers were incorporated at the FNIII8 and FNIII10 junction. The nucleotide sequence of SEQ ID NO:5 does not encode any linking amino acid residues.

SEQ ID NO: 4

FNIII1H, 8, 10

```
atccagtgga atgcaccaca gccatctcac atttccaagt acattctcag gtggagacct   60

aaaaattctg taggccgttg gaaggaagct accataccag gccacttaaa ctcctacacc  120

atcaaaggcc tgaagcctgg tgtggtatac gagggccagc tcatcagcat ccagcagtac  180

ggccaccaag aagtgactcg ctttgacttc accaccacca gcaccagcac aggatctgct  240

gttcctcctc ccactgacct gcgattcacc aacattggtc cagacaccat gcgtgtcacc  300

tgggctccac ccccatccat tgatttaacc aacttcctgg tgcgttactc acctgtgaaa  360

aatgaggaag atgttgcaga gttgtcaatt tctccttcag acaatgcagt ggtcttaaca  420

aatctcctgc ctggtacaga atatgtagtg agtgtctcca gtgtctacga acaacatgag  480

agcacacctc ttagaggaag acagaaaaca gtttctgatg ttccgaggga cctggaagtt  540

gttgctgcga cccccaccag cctactgatc agctgggatg ctcctgctgt cacagtgaga  600

tattacagga tcacttacgg agaaacagga ggaaatagcc ctgtccagga gttcactgtg  660

cctgggagca agtctacagc taccatcagc ggccttaaac ctggagttga ttataccatc  720

actgtgtatg ctgtcactgg ccgtggagac agccccgcaa gcagcaagcc aatttccatt  780

aattaccgaa ca                                                     792
```

SEQ ID NO: 5

FNIII1H, 8, 10

```
atccagtgga atgcaccaca gccatctcac atttccaagt acattctcag gtggagacct   60

aaaaattctg taggccgttg gaaggaagct accataccag gccacttaaa ctcctacacc  120

atcaaaggcc tgaagcctgg tgtggtatac gagggccagc tcatcagcat ccagcagtac  180
```

-continued

```
ggccaccaag aagtgactcg ctttgacttc accaccacca gcaccagcac agctgttcct  240

cctcccactg acctgcgatt caccaacatt ggtccagaca ccatgcgtgt cacctgggct  300

ccaccccat ccattgattt aaccaacttc ctggtgcgtt actcacctgt gaaaaatgag  360

gaagatgttg cagagttgtc aatttctcct tcagacaatg cagtggtctt aacaaatctc  420

ctgcctggta cagaatatgt agtgagtgtc tccagtgtct acgaacaaca tgagagcaca  480

cctcttagag gaagacagaa aacagtttct gatgttccga gggacctgga agttgttgct  540

gcgaccccca ccagcctact gatcagctgg gatgctcctg ctgtcacagt gagatattac  600

aggatcactt acggagaaac aggaggaaat agccctgtcc aggagttcac tgtgcctggg  660

agcaagtcta cagctaccat cagcggcctt aaacctggag ttgattatac catcactgtg  720

tatgctgtca ctggccgtgg agacagcccc gcaagcagca agccaatttc cattaattac  780

cgaaca                                                             786
```

In another embodiment of the present invention, the at least a portion of the type III integrin binding domain comprises the minimal RGD integrin binding sequence. An exemplary RGD integrin binding sequence is the RGD sequence of RGDSPAS (SEQ ID NO: 14) present in the FNIII10 module. Alternatively, the RGD integrin binding sequence can be heterologous to the type III integrin-binding domain of fibronectin (i.e., an RGD integrin binding sequence that is not present in SEQ ID NO:1). Exemplary RGD integrin binding sequences include, without limitation, GRGD (SEQ ID NO: 15); GRGDS (SEQ ID NO: 16); GRGDSPK (SEQ ID NO: 17); GRGDTP (SEQ ID NO: 18); SDGRGRGDS (SEQ ID NO: 19); RGDS (SEQ ID NO: 20); RGDSPASSKP (SEQ ID NO: 21); RRRRRRGDSPK (SEQ ID NO: 22); and G(dR) GDSPASSK (dR is D-arginine) (SEQ ID NO: 23), or functional variants thereof. An exemplary fibronectin peptide mimetic of the present invention where the type III integrin binding domain comprises an RGD sequence is FNIII1H$^{RGD}$, having an amino acid sequence of SEQ ID NO: 6 as shown below. This amino acid sequence corresponds to amino acid residues 628-685, 1523-1530, and 690-704 of the full-length human fibronectin (SEQ ID NO:1).

```
                                                   SEQ ID NO: 6
FNIII1H^RGD
Ile Gln Trp Asn Ala Pro Gln Pro Ser His Ile Ser Lys Tyr Ile Leu
1               5                   10                  15

Arg Trp Arg Pro Lys Asn Ser Val Gly Arg Trp Lys Glu Ala Thr Ile
            20                  25                  30

Pro Gly His Leu Asn Ser Tyr Thr Ile Lys Gly Leu Lys Pro Gly Val
        35                  40                  45

Val Tyr Glu Gly Gln Leu Ile Ser Ile Gln Gly Arg Gly Asp Ser Pro
    50                  55                  60

Ala Ser Gln Glu Val Thr Arg Phe Asp Phe Thr Thr Thr Ser Thr Ser
65                  70                  75                  80

Thr
```

Nucleic acid molecules encoding FNIII1H,$^{RGD}$ comprise the nucleotide sequence of SEQ ID NO:7 or SEQ ID NO: 8 shown below. The nucleotide sequence of SEQ ID NO:7 contains a three codon sequence (underlined) containing five silent base changes (bold). The first four base changes introduce a ClaI site (ATCGAT) to facilitate cloning of the downstream sequence; the final base change renders the ClaI site methylation insensitive. The nucleotide sequence of SEQ ID NO:8 does not contain these five base changes.

```
                                                   SEQ ID NO: 7
FNIII1H,^RGD
atccagtgga atgcaccaca gccatctcac atttccaagt acattctcag gtggagacct   60

aaaaattctg taggccgttg gaaggaagct accataccag gccacttaaa ctcctacacc  120

atcaaaggcc tgaagcctgg tgtggtatac gagggccagc tcatatcgat tcagggccgt  180

ggagactcgc cggcaagcca agaagtgact cgctttgact tcaccaccac cagcaccagc  240

aca                                                                243
```

-continued

SEQ ID NO: 8

FNIII1H,$^{RGD}$ atccagtgga atgcaccaca gccatctcac atttccaagt acattctcag gtggagacct 60
aaaaattctg taggccgttg gaaggaagct accataccag gccacttaaa ctcctacacc 120
atcaaaggcc tgaagcctgg tgtggtatac gagggccagc tcatcagcat ccagggccgt 180
ggagactcgc cggcaagcca agaagtgact cgctttgact tcaccaccac cagcaccagc 240
aca 243

In yet another embodiment of the present invention, the at least a portion of the type III integrin binding domain comprises the FNIII8 module containing an RGD sequence. The RGD sequence can be derived from the FNIII10 module or it can be heterologous to the type III integrin binding domain. An exemplary fibronectin peptide mimetic comprising an FNIII8 module containing an RGD sequence is FNIII1H, 8$^{RGD}$, having an amino acid sequence of SEQ ID NO: 9 below (also shown schematically in FIG. 1 as mimetic peptide #6). This amino acid sequence corresponds to amino acids residues 628-704; 1266-1342; 1523-1530; 1347-1356 of the full-length human fibronectin (SEQ ID NO:1).

SEQ ID NO: 9

FNIII1H,$^{RGD}$

Ile Gln Trp Asn Ala Pro Gln Pro Ser His Ile Ser Lys Tyr Ile Leu
1 5 10 15

Arg Trp Arg Pro Lys Asn Ser Val Gly Arg Trp Lys Glu Ala Thr Ile
20 25 30

Pro Gly His Leu Asn Ser Tyr Thr Ile Lys Gly Leu Lys Pro Gly Val
35 40 45

Val Tyr Glu Gly Gln Leu Ile Ser Ile Gln Gln Tyr Gly His Gln Glu
50 55 60

Val Thr Arg Phe Asp Phe Thr Thr Thr Ser Thr Ser Thr Ala Val Pro
65 70 75 80

Pro Pro Thr Asp Leu Arg Phe Thr Asn Ile Gly Pro Asp Thr Met Arg
85 90 95

Val Thr Trp Ala Pro Pro Pro Ser Ile Asp Leu Thr Asn Phe Leu Val
100 105 110

Arg Tyr Ser Pro Val Lys Asn Glu Glu Asp Val Ala Glu Leu Ser Ile
115 120 125

Ser Pro Ser Asp Asn Ala Val Val Leu Thr Asn Leu Leu Pro Gly Thr
130 135 140

Glu Tyr Val Val Ser Val Ser Ser Val Tyr Gly Arg Gly Asp Ser Pro
145 150 155 160

Ala Ser Ser Thr Pro Leu Arg Gly Arg Gln Lys Thr
165 170

Nucleic acid molecules encoding FNIII1H,8$^{RGD}$ comprise the nucleotide sequence of SEQ ID NO:10 or SEQ ID NO:11 shown below. The nucleotide sequence of SEQ ID NO:10 contains the three codon sequence (underlined) containing five silent base changes (bold) described above to introduce a ClaI site, and encodes two glycine and serine residues (underlined) linking the FNIII1H and FNIII8 modules (i.e., the glycine and serine residues are inserted between the threonine and alanine residues at positions 77 and 78 of SEQ ID NO:9). The nucleotide sequence of SEQ ID NO:11 does not encode the ClaI site or linking amino acid residues.

SEQ ID NO: 10

FNIII1H, 8$^{RGD}$ atccagtgga atgcaccaca gccatctcac atttccaagt acattctcag gtggagacct 60
aaaaattctg taggccgttg gaaggaagct accataccag gccacttaaactcctacacc 120 atcaaaggcc tgaagcctgg tgtggtatac gagggccagc tcatatcgat tcagcagtac 180

-continued

```
ggccaccaag aagtgactcg ctttgacttc accaccacca gcaccagcac aggatctgct  240

gttcctcctc ccactgacct gcgattcacc aacattggtc cagacaccat gcgtgtcacc  300

tgggctccac ccccatccat tgatttaacc aacttcctgg tgcgttactc acctgtgaaa  360

aatgaggaag atgttgcaga gttgtcaatt tctccttcag acaatgcagt ggtcttaaca  420

aatctcctgc ctggtacaga atatgtagtg agtgtctcca gtgtctacgg ccgtggagac  480

tcgccggcaa gcagcacacc tcttagagga agacagaaaa ca                     522
```

SEQ ID NO: 11

FNIII1H, $8^{RGD}$

```
atccagtgga atgcaccaca gccatctcac atttccaagt acattctcag gtggagacct   60

aaaaattctg taggccgttg gaaggaagct accataccag gccacttaaa ctcctacacc  120

atcaaaggcc tgaagcctgg tgtggtatac gagggccagc tcatcagcat ccagcagtac  180

ggccaccaag aagtgactcg ctttgacttc accaccacca gcaccagcac agctgttcct  240

cctcccactg acctgcgatt caccaacatt ggtccagaca ccatgcgtgt cacctgggct  300

ccacccccat ccattgattt aaccaacttc ctggtgcgtt actcacctgt gaaaaatgag  360

gaagatgttg cagagttgtc aatttctcct tcagacaatg cagtggtctt aacaaatctc  420

ctgcctggta cagaatatgt agtgagtgtc tccagtgtct acggccgtgg agactcgccg  480

gcaagcagca cacctcttag aggaagacag aaaaca                            516
```

The recombinant fibronectin peptide mimetic of the present invention may further comprise a targeting moiety. A targeting moiety according to the present invention functions to target the peptide mimetic to a particular cell or tissue type (e.g., signaling peptide sequence). The signaling peptide can include at least a portion of a ligand binding protein. Suitable ligand binding proteins include high-affinity antibody fragments (e.g., Fab, Fab' and $F(ab')_2$), single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor.

The recombinant fibronectin peptide mimetic of the present invention may further comprise a tag. A "tag" as used herein includes any labeling moiety that facilitates the detection/imaging, quantitation, separation, and/or purification of the recombinant peptide of the present invention. Suitable tags include purification tags, ultrasound contrast agents, radioactive or fluorescent labels, and enzymatic tags.

Purification tags, such as poly-histidine ($His_{6-}$), glutathione-S-transferase (GST), or maltose-binding protein (MBP-), can assist in peptide purification or separation but can later be removed, i.e., cleaved from the peptide following recovery. Protease-specific cleavage sites can be used to facilitate the removal of the purification tag. The desired peptide mimetic product can be purified further to remove the cleaved purification tags.

Other suitable tags include ultrasound contrast agents, such as gas-filled microbubbles, that can be used for imaging and to facilitate the spatial patterning of proteins. Ultrasound contrast agents are detected using contrast-enhanced ultrasonography. Other suitable tags include radioactive labels, such as, $^{125}I$, $^{131}I$, $^{111}In$, or $^{99}TC$. Methods of radiolabeling compounds, are known in the art and described in U.S. Pat. No. 5,830,431 to Srinivasan et al., which is hereby incorporated by reference in its entirety. Radioactivity is detected and quantified using a scintillation counter or autoradiography. Alternatively, the peptide can be conjugated to a fluorescent tag. Suitable fluorescent tags include, without limitation, chelates (europium chelates), fluorescein and its derivatives, rhodamine and its derivatives, dansyl, Lissamine, phycoerythrin and Texas Red. The fluorescent labels can be conjugated to the peptide using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Other suitable tags include enzyme tags. Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., *Methods for the Preparation of Enzyme—Antibody Conjugates for Use in Enzyme Immunoassay*, in METHODS IN ENZYMOLOGY 147-66 (Langone et al. eds., 1981), which is hereby incorporated by reference in its entirety.

The recombinant fibronectin mimetics of the present invention may be prepared using standard methods of synthesis known in the art, including solid phase peptide synthesis (Fmoc or Boc strategies) or solution phase peptide synthesis.

Alternatively, peptides of the present invention may be prepared using recombinant expression systems.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide mimetic of the invention may be inserted into the vector. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize peptide mimetic production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted nucleotide sequence. Common promoters suitable for directing expression in mammalian cells include, without limitation, SV40, MMTV, metallothionein-1, adenovirus E1a, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated peptide of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety.

Once the nucleic acid molecule encoding the peptide mimetic has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant peptide mimetic. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified peptides may be obtained by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

A second aspect of the present invention relates to a wound healing composition that comprises one or more of the recombinant fibronectin peptide mimetics of the present invention and a synthetic material. Preferably, the recombinant fibronectin peptide mimetic is dispersed throughout the synthetic material. In one embodiment of the present invention, the recombinant fibronectin peptide mimetic is dispersed throughout the synthetic material in a homogenous manner. In another embodiment of the present invention, the recombinant fibronectin peptide mimetic is spatially patterned throughout the synthetic material. In accordance with this aspect of the invention, the synthetic material can be a biocompatible polymer, a biological dermal substitute, or a tissue scaffold.

When used in these wound healing compositions of the present invention, the recombinant fibronectin peptide mimetic can be present in any amount suitable to induce wound healing. In certain embodiments, the peptide can be delivered in a range of 25 nM to 25 mM, more preferably, in a range of 1 μM to 1 mM. The optimal peptide mimetic concentration for treatment will vary depending on the application (e.g., type of wound or tissue regeneration); however, determining the optimal peptide mimetic concentration can be carried out using techniques known to one of skill in the art. Ideally, the lowest effective dose of peptide mimetic that can achieve the desired wound healing or tissue regeneration is administered.

As used herein, a biocompatible polymer refers to a compound that is biostable, bioerodable, and/or bioresorbable. A biocompatible polymer may be a homopolymer or a copolymer and may contain a reactive chemical functionality that allows for grafting. A biocompatible copolymer may contain both hydrophobic and hydrophilic portions and may be a synthetic polymer, derived from naturally occurring polymers, e.g., cellulose, collagen, gelatin, fibrin, chitosan, etc.

In one embodiment of the present invention, the biocompatible polymer comprises a biostable polymer selected from the group consisting of polyurethanes, isobutylene, polystyrene-isobutylene-polystyrene, silicone, a thermoplastic elastomer, an ethylene vinyl acetate copolymer, a polyolefin elastomer, EPDM ethylene-propylene terpolymer rubber, polyamide elastomer, hydrogel, and combinations thereof. Alternatively, the biocompatible polymer comprises a bioerodable or bioresorbable polymer selected from the group consisting of polyglycolide, polylactide, poly(lactide-co-glycolide), polycaprolactone, polybutylene succinate, poly(p-dioxanone), polytrimethylene carbonate, polyphosphazenes, specific polyester polyurethanes, polyether polyurethanes, polyamides, polyorthoesters, polyester amides, maleic anhydride copolymers, poly(sebacic anhydride), polyvinyl alcohol, biopolymers, gelatin, glutens, cellulose, starches, chitin, chitosan, alginates, bacterial polymers, poly(hydroxybutyrate), poly(hydroxybutyrate-co-valerate), functionalized polymers, copolymers, and combinations or blends thereof. Other suitable biocompatible polymers include those disclosed in U.S. Pat. No. 7,709,439 to Helmus et al., which is hereby incorporated by reference in its entirety.

As used herein, biological dermal substitute refers to a skin substitute or artificial dermal replacement. The dermal substitute comprises a scaffold into which cells can migrate and repair a wound. Several biological dermal substitutes are known in the art, including, without limitation, acellular dermal substitute (ADM), a dermal collagen matrix derived from banked human skin that has been treated to remove all cellular component (see Takami et al., "Dispase/Detergent Treated Dermal Matrix as a Dermal Substitute," *Burns* 22:182-90 (1996), which is hereby incorporated by reference in its entirety; Alloderm® (LifeCell Corporation, Branchburg, N.J.), also a dermal collagen matrix derived from banked human skin that is treated to remove most cellular components; Dermagraft TC® (Advanced Tissue Sciences, La Jolla, Calif.), a woven bioabsorbable polymer membrane within which human dermal fibroblasts are grown and devitalized; Dermalogen® (Collagenesis, Beverely, Mass.), a powdered human dermal collagen matrix that is treated to remove some cellular components; Integra® (Integra Life Sciences Corp., Plainsboro, N.J.), a bilayer artificial skin replacement with a dermal layer composed of bovine collagen gel cross-linked with shark chondroitin-6-sulfate. Other biological dermal substitutes known in the art are suitable for use in the present invention.

As used herein, a tissue-scaffold refers to an engineered biomaterial, typically a degradable biomaterial, comprising cells or tissue. Preferred tissue-scaffolds include three-dimensional engineered tissue constructs or organs as described in WO10/135,044 to Dalecki et al., which is hereby incorporated by reference in its entirety. These constructs comprise a mass of living tissue produced primarily by growth in vitro and share critical structural and functional characteristics with intact tissue, such as distinctive multicellular organization and oriented contractile function. Suitable engineered tissue constructs include muscular constructs, vascular constructs, cartilaginous constructs, skeletal constructs, filamentous/ligament constructs, bone constructs, and skin constructs.

The wound healing composition of the present invention may further comprise one or more additional recombinant proteins or peptides involved in wound healing. The one or more additional recombinant proteins or peptides can be extracellular matrix proteins, growth factors, cytokines, and chemokines, or any combination thereof. The additional agents can be administered in any suitable dosage that is effective to induce or to enhance the desired wound healing. Preferably, the lowest effective dose that can contribute to the desired wound healing is utilized. Suitable extracellular matrix proteins include, without limitation, glycosaminoglycan, a proteoglycan, collage, elastin, laminin, alginate, a chitin derivative, fibrin, fibrinogen, and any combination thereof. Suitable growth factors include, without limitation, platelet derived growth factor (PDGF), tumor necrosis factor-alpha (TNF-$\alpha$), TNF-$\beta$, epidermal growth factor (EGF), keratinocyte growth factor, vascular endothelial growth factors (VEGFs), fibroblast growth factors (FGFs), tumor necrosis factor, insulin growth factor (IGF), and any combination thereof.

In a preferred embodiment of the present invention, the one or more additional recombinant proteins or peptides are spatially patterned throughout the synthetic material to facilitate the wound healing process. For example, pro-migratory proteins are patterned to contact the outside edge of the wound while pro-growth proteins are patterned to contact the center of the wound.

The wound healing composition of the present invention may also include other wound healing agents, such as anti-inflammatory agents, antimicrobial agents, healing promoters, and combinations thereof.

Anti-inflammatory agents useful for dispersion in the wound healing composition of the present invention include, without limitation, analgesics (e.g., NSAIDS and salicyclates), hormones (glucocorticoids), and skin and mucous membrane agents. Specifically, the anti-inflammatory agent can include dexamethasone. Alternatively, the anti-inflammatory agent can include sirolimus (rapamycin), which is a triene macrolide antibiotic isolated from *Steptomyces hygroscopicus*. The anti-inflammatory agents can be administered in any suitable dosage that is effective to induce or to enhance the desired wound healing. Preferably, the lowest effective dose that can contribute to the desired wound healing is utilized.

A variety of antibiotics and antimicrobials can also be dispersed in the wound healing compositions to indirectly promote natural healing processes by preventing or controlling infection. Suitable antibiotics include aminoglycoside antibiotics (e.g., gentamycin, tobramycin), quinolones, beta-lactams (e.g., ampicillin, cefalosporines), ciprofloxacin, erythromycin, vancomycin, oxacillin, cloxacillin, methicillin, lincomycin, and colistin. Suitable antimicrobials include, for example, Adriamycin PFS/RDF® (Pharmacia and Upjohn), Blenoxane® (Bristol-Myers Squibb Oncology/Immunology), Cerubidine®. (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Miamycin®. (Bristol-Myers Squibb Oncology/Immunology), Nipen® (SuperGen), Novantrone® (Immunex) and Rubex® (Bristol-Myers Squibb Oncology/Immunology). The antibiotics and antimicrobial agents can be administered in any suitable dosage that is effective to induce or to enhance the desired wound healing.

Preferably, the lowest effective dose that can contribute to the desired wound healing is utilized.

Suitable wound healing promoters include, without limitation, vitamin A and synthetic inhibitors of lipid peroxidation. Other suitable wound healing promoters include agents that promote natural wound healing processes by endothelial cells. These wound healing agents include any bioactive agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such wound-healing agents include, for example, aminoxyls, furoxans, nitrosothiols, nitrates and anthocyanins; nucleosides, such as adenosine; nucleotides, such as adenosine diphosphate (ADP) and adenosine triphosphate (ATP); histamine and catecholamines; lipid molecules, such as sphingosine-1-phosphate and lysophosphatidic acid; amino acids, such as arginine and lysine; peptides such as the bradykinins, substance P and calcium gene-related peptide (CGRP), and proteins, such as insulin, vascular endothelial growth factor (VEGF), and thrombin. The wound healing promoting agents can be administered in any suitable dosage that is effective to induce or to enhance the desired wound healing. Preferably, the lowest effective dose that can contribute to the desired wound healing is utilized.

These wound healing compositions of the present invention are suitable for administration to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Formulations for wound healing usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared.

The wound healing compositions of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, gels, ointments, and, in some cases, suppositories. For salves and creams, traditional binders, carriers and excipients may include, for example, polyalkylene glycols or triglycerides.

Another aspect of the present invention relates to a wound dressing that comprises the wound healing composition or recombinant peptide of the present invention, described supra, and a wound dressing material.

The wound dressing material can be any material applied to a wound for protection, absorbance, drainage, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), cellophane (cellulose with a plasticizer), gauze, alginate, polysaccharide paste, granules, and beads.

Another aspect of the present invention relates to a method of treating a wound. This method involves providing the wound healing composition of the present invention and applying the wound healing composition to the wound under conditions suitable to promote healing of the wound. In a preferred embodiment of the present invention, the wound healing composition enhances or increases the rate of healing of the wound being treated.

In accordance with this aspect of the present invention, the wound healing composition of the present invention is administered in a suitable dosage that is effective to induce or to enhance the desired wound healing. Preferably, the lowest effective dose that can contribute to the desired wound healing is utilized. The wound healing composition of the present invention is preferably reapplied periodically until the wound heals. For example, the wound healing composition may be applied twice daily, daily, every other day, of every two days, until the desired healing is achieved (e.g., 50-70% wound closure). The optimal dosage and frequency of application will vary depending on the wound and can be determined using techniques readily known to one of skill in the art.

In one embodiment of the present invention, the wound healing composition comprises a biocompatible polymer. Once the polymer based composition is contacted with the wound it is allowed to polymerize, thereby increasing the rate of healing.

The wound healing composition of the present invention is suitable for treatment of internal and external wounds. The wound healing composition of the present invention is particularly suitable for treatment of chronic non-healing wounds, such as diabetic ulcers, pressure ulcers, leg ulcers, dermal ulcers, burns, corneal wounds, and incisions which involve body tissues being cut, abraded, or otherwise damages.

In another embodiment of the invention, the wound healing composition of the present invention is used for inducing or enhancing the regeneration of healthy tissue (e.g., cartilage, bone, nervous tissue, muscle tissue, soft tissue, vasculature, etc.). Treatment with the wound healing composition of the present invention is particularly suitable for conditions that cause organ damage, such as, e.g., liver disease (cirrhosis), pancreatic disease, and lung disease (emphysema). Alternatively, the wound healing composition of the present invention is useful for regenerating healthy tissue after reconstructive or elective plastic surgery.

EXAMPLES

The following examples are provided to illustrate embodiments of the present invention but they are by no means intended to limit its scope.

Materials and Methods for Examples 1-6

Reagents, antibodies, and cells. Human plasma fibronectin was isolated from Cohn's fraction I and II (Miekka et al., "Rapid Methods for Isolation of Human Plasma Fibronectin," *Thromb. Res.* 27:1-14 (1982), which is hereby incorporated by reference in its entirety). Type I collagen was extracted from rat tail tendons using acetic acid and precipitated with NaCl (Windsor et al., MATRIX METALLOPROTEINASES 10.8.6-

10.8.7 (Wiley & Sons, Inc. 2002), which is hereby incorporated by reference in its entirety). Human fibrinogen was a gift from Dr. Patricia Simpson-Haidaris (University of Rochester, Rochester, N.Y.). Recombinant vitronectin was expressed and purified as previously described (Wojciechowski et al., "Expression, Production, and Characterization of Full-Length Vitronectin in *Escherichia coli," Prot. Expr. Purif.* 36(1):131-138 (2004), which is hereby incorporated by reference in its entirety). GRGDSP (SEQ ID NO: 24) peptides were obtained from Sigma (St. Louis, Mo.). FN12-8 monoclonal antibody was obtained from Takara (Madison, Wis.); horseradish peroxidase-conjugated goat anti-mouse antibody was from Bio-Rad (Hercules, Calif.). Tissue culture supplies were from Corning/Costar (Cambridge, Mass.). Unless otherwise indicated, chemical reagents were from J. T. Baker (Phillipsburg, N.J.) or Sigma.

Mouse embryonic fibronectin-null fibroblasts (FN-null MEFs; provided by Dr. Jane Sottile, University of Rochester, Rochester, N.Y.) were cultured on collagen I-coated dishes under fibronectin- and serum-free conditions using a 1:1 mixture of CELLGRO® (Mediatech, Herndon, Va.) and Aim V (Invitrogen) (Sottile et al., "Fibronectin Matrix Assembly Enhances Adhesion-Dependent Cell Growth," *J. Cell Sci.* 111:2933-2943 (1998), which is hereby incorporated by reference in its entirety).

Recombinant protein production and purification. A schematic of the recombinant proteins used in this study is shown in FIG. 1A. As noted above, reference to amino acid residues of the fibronectin peptides and domains in the Examples reflects the mature fibronectin protein that does not contain the 31 amino acid leader sequence.

Recombinant GST/III1H,8-10 (Peptide #1 of FIG. 1A), GST/III1H (Peptide #7 of FIG. 1A), GST/III8-10 (Peptide #10 of FIG. 1A), and GST/III8-10,13 (Peptide #11) were produced in *E. coli* and purified as described (Gui et al., "Identification of the Heparin-Binding Determinants Within Fibronectin Repeat III1: Role in Cell Spreading and Growth," *J. Biol. Chem.* 281(46):34816-34825 (2006) and Hocking et al., "A Cryptic Fragment From Fibronectin's III-1 Module Localizes To Lipid Rafts And Stimulates Cell Growth And Contractility," *J. Cell Biol.* 158:175-184 (2002), which are hereby incorporated by reference in their entirety). A fibronectin fragment in which a C-terminal fragment of Extra domain-B ($ED_B$-C) was coupled to the integrin-binding modules, 1118-10 (GST/IIIE$D_B$-C,8-10) (Peptide #9 of FIG. 1A), was produced using the sense primer: 5'-CCCAGATCTCTGAGGTGGACCCCGCTAAAC-3' (SEQ ID NO:25) and antisense primer: 5'-CCCCCCGGGCTATGTTCGGTAATTAATGGAAATTG-3' (SmaI site in bold; SEQ ID NO:26). The human fibronectin cDNA construct pCEF103 was used as a template (Dufour et al., "Generation of Full-Length cDNA Recombinant Vectors for the Transient Expression of Human Fibronectin in Mammalian Cell Lines," *Exp. Cell Res.* 193(2):331-338 (1991), which is hereby incorporated by reference in its entirety). GST/III1H,8-10ΔRRK ($R^{613}$T, $R^{615}$T, $K^{617}$A) was produced with the forward primer 5'-CCCGGTACCATCCAGTGGAATGCACCACAGCCATCTCACATTTCCAAGTACATTC TCACGTGG ACACCTGCAAATTCTGTAGGC-3' (SEQ ID NO:27). The Kpn1 site is shown in bold and the mutant codons are underlined. The reverse primer was 5'-CCCGAATTCCTATGTGCTGGTGCTGGTGGTG-3' (SEQ ID NO:28) with the EcoR1 site in bold. GST/III1H,8-10ΔEGQ ($E^{647}$D,$Q^{649}$N) was produced using the following mutant sense primer: 5'-GGTATACGACGGC AACCTGATCAGCATCCAGCACTACG-3' (SEQ ID NO:29). Mutations are underlined; a BstZ17I site is shown in bold. The antisense primer for GST/III1H,8-10ΔEGQ was the same as that used for GST/III1H,8-10 (5'-CCCCCCGGGCTATGTTCGGTAATTAATGGAAATTG-3'(SEQ ID NO:30)), which contains a Sma1 site (bold). Human full-length fibronectin cDNA pFH100 was used as a template.

Recombinant fibronectins that contained deletions to type III modules within the cell binding domain were made using GST/III1H,8-10 plasmid DNA as the template. The sense primer, beginning in FNIII1, for these constructs was: 5'-CCCGGATCCATCCAGTGGAATGCACCACAG-3' (SEQ ID NO:31). The BamH1 site is shown in bold. GST/III1H,8 (Peptide #5 of FIG. 1A) was made with the antisense primer: 5'-GTCACGATCAATTCCCGGGCTATGTTTTCTGTCTTCCTCTA-3' (SEQ ID NO:32), which contains a Sma1 site shown in bold. GST/III1H,8,10 (Peptide #2 of FIG. 1A) was made with the following antisense primer that includes the 5' end of FNIII10 and the 3' end of FNIII8: 5'-GGTCCCTCGGAACATCAGAAACTGTTTTCTGTCTTCCTCTAAGAGG-3' (SEQ ID NO:33). An AlwNI site is shown in bold. GST/III1H,10 (Peptide #4 of FIG. 1A) was made using the antisense primer: 5'-CCAGGTCCCTCGGAACATCAGAAACTGTGCTGGTGCTGGTGG-3' (SEQ ID NO:34), which runs from the PpuMI site in FNIII10 (bold) into the 3' end of FNIII1-H. GST/III1H,9-10 (Peptide #3) was made by first engineering a ClaI site (bold) into FNIII1H of pGEX-2T/III1H,8-10 with the sense primer: 5'-GGTATACGAGGGCCAGCTCATATCGATCCAGCAGTACGG-3' (SEQ ID NO:35). The BstZ17I site in FNIII1 is underlined. FNIII1H was then coupled directly to FNIII9 by deleting FNIII8 from pGEX2T/III1H,8-10 with the sense primer: 5'-CATATCGATCCAGCAGTACGGCCACCAAGAAGTGACTCGCTTTGACTTCACCAC CACCAGCACCAGCACAGGTCTTGATTCCCCAACTGG-3' (SEQ ID NO:36). The Cla1 site, shown in bold, was used to move this fragment into pGEX-2T/III1H,8-10.

Figure 1B:
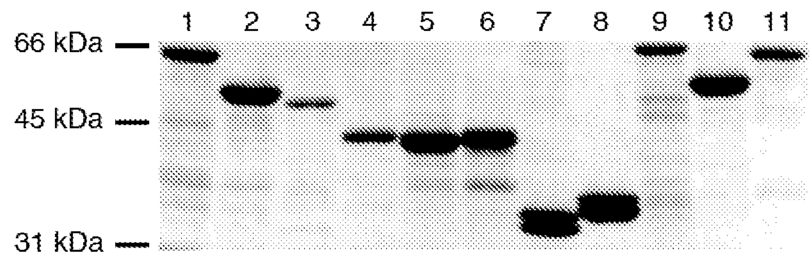

The RGD chimera, GST/III1H,$8^{RGD}$ (Peptide #6 of FIG. 1A), was produced using the following mutant sense primer: 5'-GTGAGTGTCTCCAGTGTCTAC GGCCGTGGAGACTCGCCGGCAAGCAGCACACCTC TTAGAGGAAGACAGAAAACATAGGAATTCA-3' (SEQ ID NO:37). The insert from FNIII10 (bases 4487-4510 in pFH100; underlined), which encodes for the GRGDSPAS sequence (SEQ ID NO: 38), was inserted between base 3946 and base 3959 ($Y^{1402}$ and $S^{1407}$) of FNIII8 (pFH100), leading to the addition of four amino acids (RGDS) to FNIII8. The EcoR1 site is shown in bold. The FNIII10 insert contains an engineered NgoMIV site as a marker. The antisense primer for GST/III1H,$8^{RGD}$ (5'-GGTATACGAGGGCCAGCTCATATCGATTCAGCAGTACGGCC-3' (SEQ ID NO:39)) contains a BstZ17I site shown in bold. GST/III$8^{RGD}$ (Peptide #8 of FIG. 1A) was engineered using pGEX-2T/III1H,$8^{RGD}$ as a template. The sense primer used was: 5'-CGGATCCGCTGTTCCTCCTCCCACTGACCTGCG-3'(SEQ ID NO:40), with the BamHI site shown in bold. The antisense primer for GST/III$8^{RGD}$ (5'-CGAATTCCTATGTTTTCTGTCTTCC-3' (SEQ ID NO:41)) contains an EcoRI site shown in bold. For all protein constructs, PCR-amplified DNA was cloned into pGEX-2T (Amersham Biosciences) and transfected into DH5a bacteria (Hocking et al., "A Cryptic Fragment From Fibronectin's III-1 Module Localizes To Lipid Rafts And Stimulates Cell Growth And Contractility," *J. Cell Biol.* 158:175-184 (2002), which is hereby incorporated by reference in its entirety). DNA was sequenced to confirm the presence of the mutations. GST-tagged fibronectin constructs were isolated on glutathione-Sepharose (Amersham Biosciences) and dialyzed extensively against PBS (Hocking et al., "Fibronectin's III-1 Module Contains a Conformation-Dependent Binding Site for the Amino-Terminal Region of Fibronectin," *J. Biol. Chem.* 269:19183-19191 (1994), which is hereby incorporated by reference in its entirety). Proteins were filter-sterilized and purity was assessed by SDS-polyacrylamide gel electrophoresis (Hocking et al., "A Cryptic Fragment From Fibronectin's III-1 Module Localizes To Lipid Rafts And Stimulates Cell Growth And Contractility,"*J. Cell Biol.* 158:175-184 (2002), which is hereby incorporated by reference in its entirety) (FIG. 1B). Purified proteins were stored in aliquots at −80° C.

Cell adhesion and proliferation assays. Tissue culture plates (48- or 96-well) were coated with recombinant fibronectin proteins or full-length ECM proteins diluted in PBS at the indicated concentrations for 90 min at 37° C. Unbound protein was removed and wells were washed with PBS. For cell proliferation assays, FN-null MEFs were seeded at $2.5\times10^3$ cells/cm$^2$ in Aim V/Cellgro and incubated for 4 days at 37° C., 8% $CO_2$. For cell adhesion assays, FN-null MEFs were seeded at $1.5\times10^5$ cells/cm$^2$ in Aim V/Cellgro and cells were allowed to adhere for 30 min at 37° C., 8% $CO_2$. After incubation, cells were washed with PBS and fixed with 1% paraformaldehyde. Cells were stained with 0.5% crystal violet, solubilized in 1% sodium dodecyl sulfate (SDS), and the absorbance at 590 nm was measured with a microplate spectrophotometer (Bio-Rad) (Hocking et al., "Activation of Distinct $\alpha_5\beta_1$-Mediated Signaling Pathways by Fibronectin's Cell Adhesion and Matrix Assembly Domains," *J. Cell Biol.* 141:241-253 (1998)).

Solid-phase enzyme linked immunosorbent assay. Tissue culture plates (96-well) were incubated with recombinant fibronectin proteins or plasma fibronectin diluted in PBS at the indicated concentrations for 90 min at 37° C. Wells were washed with PBS to remove unbound protein, then blocked with 1% BSA in PBS. Bound proteins were detected using an anti-FNIII10 monoclonal antibody (FN12-8, 1 μg/ml) followed by horseradish peroxidase-conjugated goat anti-mouse secondary antibodies. Wells were washed with PBS and the assay was developed using 2,2-azino-bis(3-ethylbenzthiazolinesulfonic acid) and the absorbance at 405 nm was measured.

Cell migration assay. An in vitro wound repair assay was used to measure cell migration (Hocking et al., "Fibronectin Polymerization Regulates Small Airway Epithelial Cell Migration," *Am. J. Physiol. Lung Cell Mol. Physiol.* 285: L169-L179 (2003), which is hereby incorporated by reference in its entirety). Tissue culture plates (35-mm) were coated with recombinant fibronectin constructs or full-length fibronectin at 200 nM in PBS for 90 min at 37° C. FN-null MEFs were seeded at $7.4\times10^4$ cells/cm$^2$ in Aim V/Cellgro. Cells were allowed to adhere and spread for either 4 or 16 h to establish a confluent monolayer. A thin section of the monolayer was carefully removed with a sterile, plastic microspatula. Cells were washed twice with Aim V/Cellgro. Five non-overlapping regions of the wound were viewed immediately after wounding with an Olympus inverted microscope using a 4× objective (time=0 h). Phase contrast images of each region were obtained using a Spot digital camera (Diagnostic Instruments, Sterling Heights, Mich.). Images were obtained of the five non-overlapping regions at various times after wounding. A numbered grid was marked on the bottom of the tissue culture plates prior to cell seeding to ensure that the same regions were being photographed at each time point. The average width of the initial wound was ~500 μm. Wound area measurements were obtained using ImagePro-Plus software (Media Cybernetics, Silver Spring, Md.). Cell migration was calculated as original cleared area (time=0 h)−cleared area (time=2, 4, 6, or 8 h).

Collagen gel contraction assay. Collagen gel contraction assays were performed as described previously (Hocking et al., "Stimulation of Integrin-Mediated Cell Contractility by Fibronectin Polymerization," *J. Biol. Chem.* 275:10673-10682 (2000), which is hereby incorporated by reference in its entirety). Neutralized collagen gels were prepared by mixing collagen type I with 1× Dulbecco's modified Eagle's medium (DMEM; Life Technologies), 2× concentrated DMEM, and 0.1 NaOH on ice for final concentrations of 0.8 mg/ml collagen and 1×DMEM, pH 7.2. FN-null MEFs were added to the collagen mixture to a final concentration of $2\times10^5$ cells/ml. An equal volume of Aim V/Cellgro was added to aliquots of the collagen mixture for 'no cell' controls. Recombinant fibronectin proteins or plasma fibronectin were added to the collagen/cell mixtures at various concentrations. Aliquots (0.1 ml) of the collagen/cell mixture were added to wells of tissue culture plates (96-well) precoated with 2% BSA in PBS. Gels were allowed to polymerize for 1 h at 37° C., 8% $CO_2$. To form floating gels, DMEM (0.1 ml/well) was added and wells were scored with a pipette tip. Following a 20 h incubation at 37° C., 8% $CO_2$, gels were removed from their wells and weighed (Model AE260, Mettler, Toledo, Ohio). Volumetric collagen gel contraction was calculated as the decrease in gel weight relative to the control, no-cell gel weight.

Statistical analysis. Data are presented as mean±standard error of the mean (SEM) and represent one of at least three experiments performed in either triplicate or quadruplicate. Statistical comparisons were performed using one-way analysis of variance (ANOVA) followed by Tukey's post-test, with GraphPad Prism Version 4 software (LaJolla, Calif.). Differences were considered significant for p values less than 0.05.

Example 1

Figure 2A:
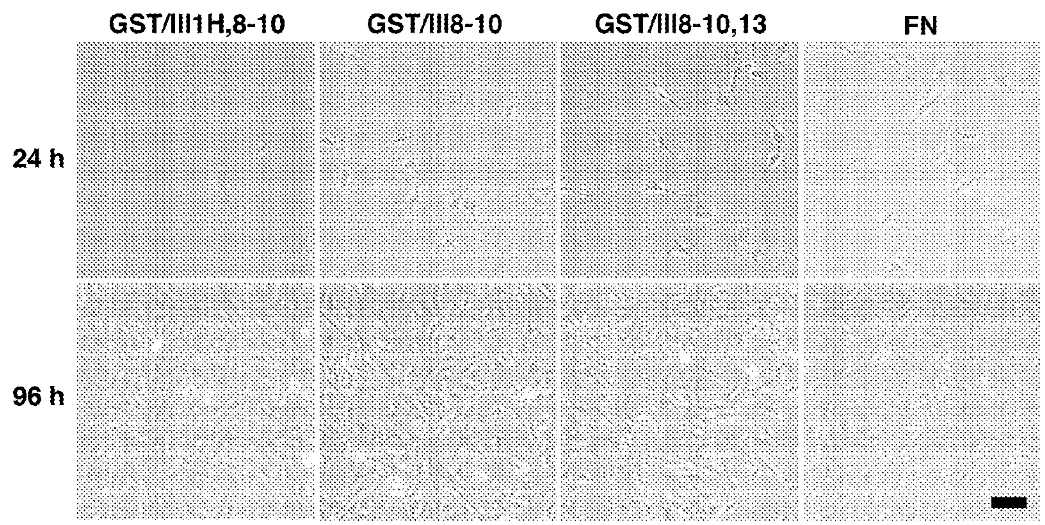
FIGS. 2A-2B show that GST/III1H,8-10 exhibits greater growth-promoting activity than fibronectin. FN-null MEFs were seeded on tissue culture plates ($2.5\times10^3$ cells/$cm^2$) pre-coated with either 200 nM (FIG. 2A) or increasing concentrations of the various proteins (FIG. 2B) and incubated for 4 days (96 h).
Figure 2B:
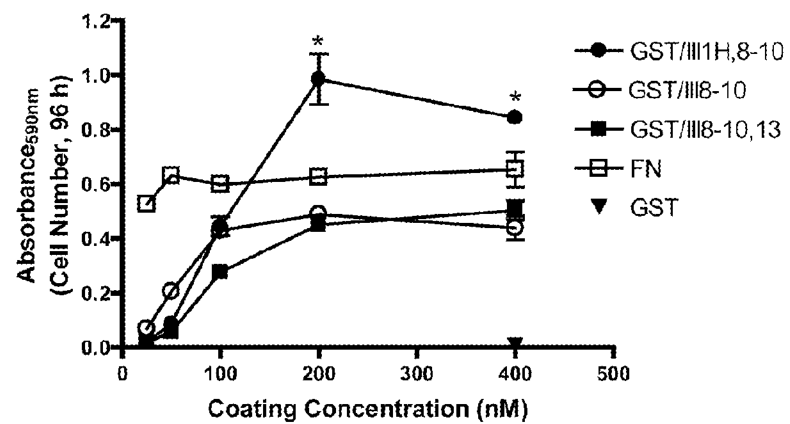

GST/III1H,8-10 Supports Cell Adhesion and Spreading, and Enhances Cell Proliferation A recombinant fibronectin construct (GST/III1H,8-10) was previously developed that mimics many of the cellular effects of ECM fibronectin, by directly coupling the cryptic, heparin-binding fragment of the first type III repeat of fibronectin to the integrin-binding domain (Hocking et al., "A Cryptic Fragment From Fibronectin's III-1 Module Localizes To Lipid Rafts And Stimulates Cell Growth And Contractility," *J. Cell Biol.* 158:175-184 (2002), which is hereby incorporated by reference in its entirety). Addition of soluble GST/III1H,8-10 to the culture media of adherent FN-null MEFs enhances cell spreading, growth, and contractility (Hocking et al., "A Cryptic Fragment From Fibronectin's III-1 Module Localizes To Lipid Rafts And Stimulates Cell Growth And Contractility," *J. Cell Biol.* 158:175-184 (2002), which is hereby incorporated by reference in its entirety), increases the migration rate of small airway epithelial cells (Hocking et al., "Fibronectin Polymerization Regulates Small Airway Epithelial Cell Migration," *Am. J. Physiol. Lung Cell Mol. Physiol.* 285:L169-L179 (2003), which is hereby incorporated by reference in its entirety), and induces local arteriolar vasodilation in vivo (Hocking et al., "Extracellular Matrix Fibronectin Mechanically Couples Skeletal Muscle Contraction with Local Vasodilation," *Circ. Res.* 102:372-379 (2008), which is hereby incorporated by reference in its entirety). To develop fibronectin matrix mimetics as functional ligands for adhesive biomaterials, studies were conducted to characterize the proliferative response of FN-null MEFs cells to immobilized GST/III1H,8-10. The use of FN-null MEFs allows the characterization of cell behavior in response to the recombinant fibronectin proteins in the absence of endogenous full-length fibronectin and the identification of specific effects of individual domains and amino acid sequences of fibronectin on cell function. Cells were seeded at low density onto tissue culture plates coated with various recombinant fibronectin fragments and cell number was determined after 4 days. The extent of cell proliferation on GST/III1H,8-10-coated substrates was compared to that observed in response to substrates coated with the following ligands: (i) an integrin-binding fragment lacking FNIII1H (GST/III8-10) (Peptide #10, FIG. 1A), (ii) a construct in which the carboxyl-terminal heparin-binding domain of fibronectin was coupled to FNIII8-10 (GST/III8-10,13) (Peptide #11, FIG. 1A), and (iii) plasma fibronectin. At 24 hours after seeding, cells adherent to the fusion protein substrates were well-spread and displayed morphologies similar to that observed with cells adherent to plasma fibronectin (FIG. 2A, top row). Cells proliferated over the 4 day period on all substrates tested and formed a near-confluent monolayer on substrates coated with GST/III1H,8-10 (FIG. 2A, bottom row, first panel). Relative cell number on Day 4 was quantified as a function of protein coating concentration. Cell number on surfaces pre-coated with either 200 nM or 400 nM GST/III1H,8-10 was significantly greater than that observed on surfaces pre-coated with either plasma fibronectin or the integrin-binding fragment, GST/III8-10 (FIG. 2B). Average cell numbers obtained from surfaces pre-coated with GST/III1H,8-10 at 200 nM were 1.32±0.08 (n=5) and 1.49±0.05 (n=15)-fold greater than those obtained on surfaces coated with the same molar concentration of plasma fibronectin or GST/III8-10, respectively. The increase in cell number observed on GST/III1H,8-10-coated surfaces required FNIII1H, as cell number on GST/III8-10,13-coated surfaces was similar to GST/III8-10-coated surfaces (FIG. 2B).

Figure 3A:
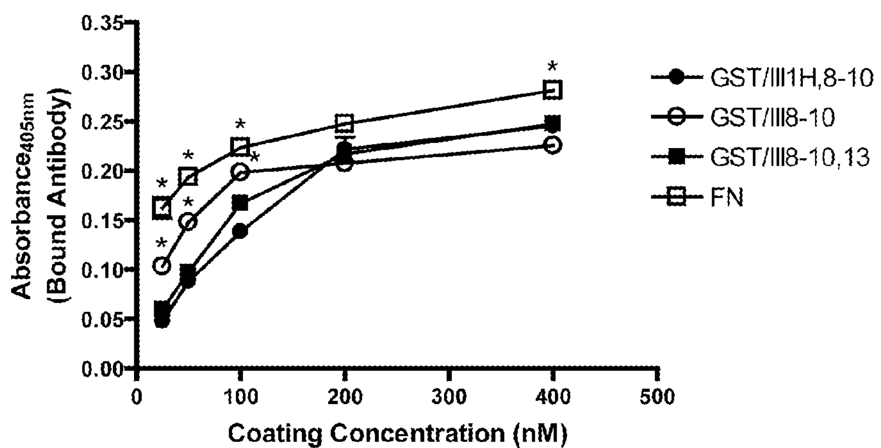
FIGS. 3A-3B depict the analyses of protein surface adsorption and cell adhesion. Tissue culture plates were coated with increasing concentrations of the indicated fibronectin peptide mimetics. The relative amount of peptide bound to wells was determined by ELISA and shown in the graph of FIG. 3A.

To compare ligand densities of the substrates, ELISAs were performed on tissue culture plates coated with increasing concentrations of protein. At protein coating concentrations less than 200 nM, differences in the relative amount of protein bound to the tissue culture plastic were observed, with GST/III8-10 and plasma fibronectin binding more efficiently than either GST/III1H,8-10 or GST/III8-10,13 (FIG. 3A). For all fusion proteins tested, ligand surface density reached saturation at a concentration of 200 nM. No differences in ligand density were observed among the various recombinant fusion proteins at coating concentrations of 200 nM and 400 nM (FIG. 3A). The ligand density of plates coated with plasma fibronectin at 400 nM was slightly greater than that observed with the recombinant proteins (FIG. 3A). Together, these data indicate that the increase in cell number observed on substrates coated with GST/III1H,8-10 (FIG. 2B) was not due to differences in the coating density of the proteins.

Figure 3B:
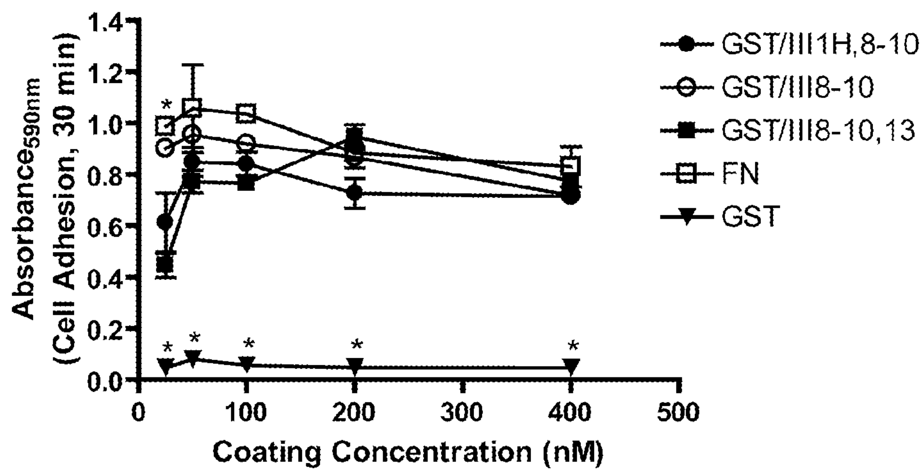

To quantify cell attachment to the various proteins, adhesion assays were performed 30 min after seeding cells at high density onto tissue culture plates pre-coated with increasing concentrations of protein. No differences in cell number were detected among the various groups at coating concentrations greater than 50 nM (FIG. 3B), indicating that the differences in cell number observed after 96 h were not due to differences in initial cell adhesion. As expected, cells did not adhere to wells coated with GST alone (FIG. 3B). Taken together, these data indicate that surfaces coated with GST/III1H,8-10 support cell adhesion and spreading and promote cell proliferation to a greater extent than surfaces coated with either plasma fibronectin or fragments with only integrin-binding activity.

Example 2

Figure 4A:
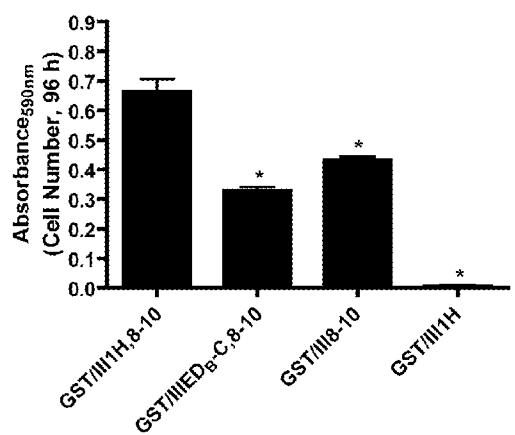
FIGS. 4A-4D demonstrate that FNIII1H is essential for the enhanced growth response. FN-null MEFs were seeded at a density of $2.5\times10^3$ cells/cm$^2$ (FIGS. 4A and 4C) or $1.5\times10^5$ cells/cm$^2$ (FIGS. 4B and 4D) on tissue culture plates coated with 200 nM recombinant fibronectin constructs.
Figure 4B:
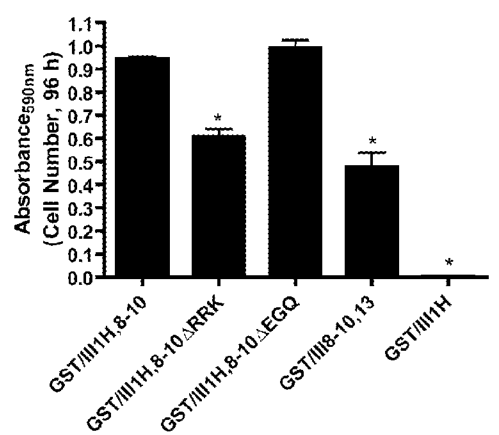

The Heparin-Binding Site in FNIII1H is Essential but not Sufficient for Increased Cell Growth To further evaluate the role of FNIII1H in the proliferative response to GST/III1H,8-10, a fusion protein was produced in which the analogous C-terminal region of the ED-B module of fibronectin was substituted for FNIII1H (GST/IIIED$_B$-C,8-10) (Peptide #9, FIG. 1A). FN-null MEFs were seeded onto surfaces coated with 200 nM GST/III1H,8-10, GST/IIIED$_B$-C,8-10, GST/III8-10, or GST/III1H and cell number was determined after 96 h. Similar to results shown in FIG. 2B, surfaces coated with GST/III1H,8-10 produced a significant increase in cell number versus surfaces coated with either GST/III8-10 or GST/IIIED$_B$-C,8-10 (FIG. 4A). No difference in initial cell adhesion to surfaces coated with GST/III1H,8-10, GST/III8-10, or GST/IIIED$_B$-C,8-10 were observed (FIG. 4B). Surfaces coated with GST/III1H alone did not support either cell adhesion (FIG. 4B) or proliferation (FIG. 4A).

Figure 4C:
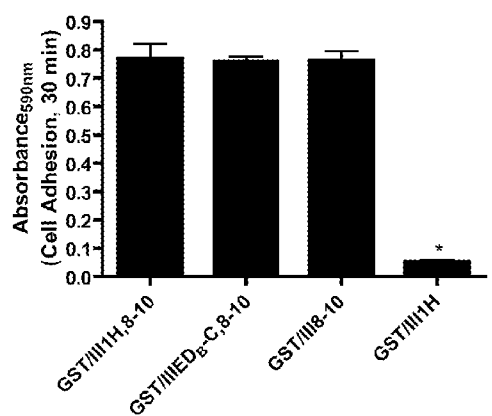
Figure 4D:
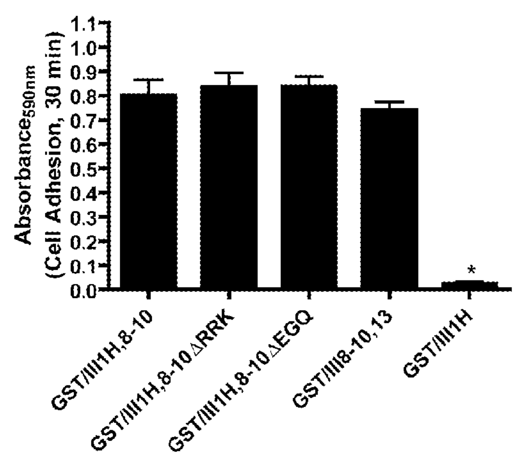

The growth-promoting site in soluble GST/III1H,8-10 was recently localized to the heparin-binding sequence, Arg$^{613}$-Trp$^{614}$-Arg$^{615}$-Pro$^{616}$-Lys$^{617}$, in FNIII1 (corresponding to amino acid residues 644-648 of SEQ ID NO:1). To further localize the growth-stimulating site in FNIII1H, a construct was produced in which only the charged amino acid sequences within the R$^{613}$WRPK sequence were mutated to non-charged amino acids (R$^{613}$T, R$^{615}$T, K$^{617}$A; GST/III1H,8-10ΔRRK). An additional control fusion protein was produced in which a separate, highly conserved sequence in FNIII1H, E$^{647}$G$^{648}$Q$^{649}$, was mutated (E$^{647}$D, Q$^{649}$N; GST/III1H,8-10ΔEGQ). FN-null MEFs were seeded onto surfaces coated with 200 nM of the various fusion proteins and cell number was determined after 96 h. Cell number on surfaces coated with GST/III1H,8-10ΔRRK was less than that observed on surfaces coated with GST/III1H,8-10, and was similar to that observed on GST/III8-10,13-coated surfaces (FIG. 4C). Cell number on GST/III1H,8-10ΔEGQ was not different than that observed on GST/III1H,8-10 (FIG. 4C), providing additional evidence that the growth-promoting activity of FNIII1 is specific to Arg$^{613}$, Arg$^{615}$, Lys$^{617}$ and that differences in cell number were not due to non-specific structural changes in the mutated protein. No differences in initial cell adhesion were observed among the groups (FIG. 4D). Taken together, these results indicate that the Arg$^{613}$_Arg$^{615}$_Lys$^{617}$ sequence in FNIII1H mediates the enhanced growth response to GST/III1H,8-10, but that in the absence of FNIII8-10, FNIII1H is unable to support cell adhesion.

Example 3

FNIII8 and FNIII10 are Required for the Cell Growth Response

Figure 5A:
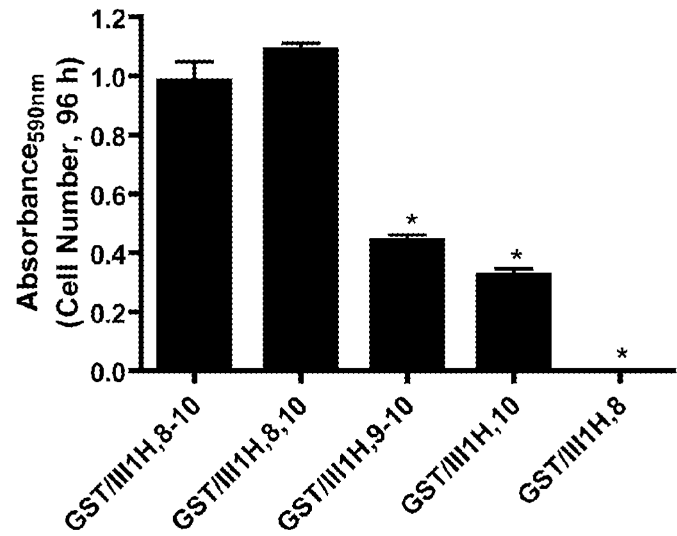
FIGS. 5A-5B show that FNIII8 and FNIII10 are required for cell growth responses. FN-null MEFs were seeded at a density of $2.5\times10^3$ cells/cm$^2$ (FIG. 5A) or $1.5\times10^5$ cells/cm$^2$ (FIG. 5B) onto tissue culture plates precoated with 200 nM of the recombinant fibronectin constructs.
Figure 5B:
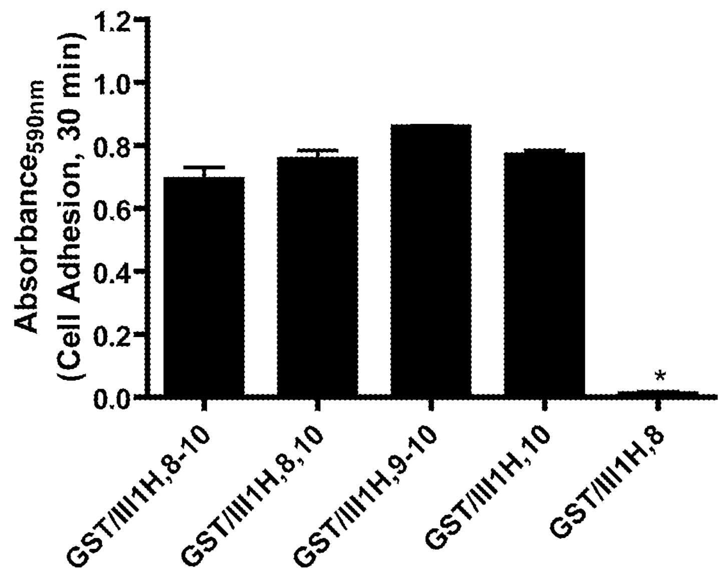

FNIII8, FNIII9, and FNIII10 form the primary integrin-binding region of fibronectin, regulating cell adhesion and cell surface receptor specificity (Magnusson et al., "Fibronectin: Structure, Assembly, and Cardiovascular Implications," *Arterio. Thromb. Vasc. Biol.* 18:1363-1370 (1998), which is hereby incorporated by reference in its entirety). FNIII10 contains the integrin-binding, RGD sequence (Pierschbacher et al., "Variants of the Cell Recognition Site of Fibronectin that Retain Attachment-Promoting Activity," *Proc. Natl. Acad. Sci. U.S.A.* 81:5985-5988 (1984), which is hereby incorporated by reference in its entirety), whereas FNIII9 contains a sequence, termed the synergy site, which promotes binding to $\alpha5\beta1$ integrins (Aota et al., "The Short Amino Acid Sequence Pro-His-Ser-Arg-Asn in Human Fibronectin Enhances Cell-Adhesive Function," *J. Biol. Chem.* 269(40): 24756-24761 (1994), which is hereby incorporated by reference in its entirety). Thus far, the data indicate that the integrin-binding domain, FNIII8-10, is necessary for adhesion and growth in response to GST/III1H,8-10 (FIG. 4). To determine whether all three integrin-binding modules are necessary for the proliferative response to GST/III1H,8-10, a series of fusion proteins were produced in which one or two modules within the integrin-binding region were deleted. The modules deleted and the constructs produced were: (i) FNIII9 (GST/III1H,8,10) (Peptide #2, FIG. 1A), (ii) FNIII8 (GST/III1H,9-10) (Peptide #3, FIG. 1A), (iii) FNIII8 and FNIII9 (GST/III1H,10) (Peptide #4, FIG. 1A), and (iv) FNIII9 and FNIII10 (GST/III1H,8) (Peptide #5, FIG. 1A). FN-null MEFs were seeded onto surfaces coated with the various fusion proteins and cell number was determined on Day 4. Deleting FNIII9 from GST/III1H,8-10 did not lead to a difference in cell number compared to the original matrix mimetic (GST/III1H,8,10 versus GST/III1H,8-10; FIG. 5A). In contrast, deleting FNIII8 from GST/III1H,8-10 resulted in a reduction in cell number on Day 4 (GST/III1H,9-10 and GST/III1H,10 versus GST/III1H,8-10; FIG. 5A). Cell adhesion to surfaces coated with GST/III1H,8,10, GST/III1H,9-10 or GST/III1H,10 was similar to that observed on GST/III1H,8-10-coated surfaces (FIG. 5B), indicating that the differences in cell number observed on Day 4 were not due to differences in initial cell attachment. Cells did not adhere to the construct lacking FNIII10 (GST/III1H,8; FIG. 5B), indicating that FNIII8 cannot support cell adhesion in the absence of FNIII10. Taken together, these data indicate that GST/III1H,8,10 supports cell adhesion and promotes cell growth to a similar extent as the original construct, GST/III1H,8-10. In addition, FNIII8 and FNIII10, but not FNIII9, are required for the full proliferative response to the fibronectin matrix mimetics.

Example 4

RGD-Chimeras Support Cell Adhesion and Promote Cell Growth

Figure 6A:
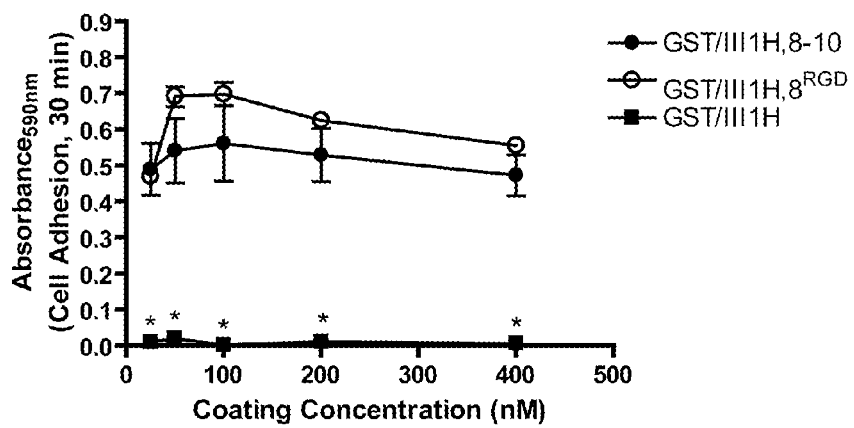
FIGS. 6A-6B show that the chimeric matrix mimetics of the present invention support cell adhesion and growth. FN-null MEFs were seeded at $1.5\times10^5$ cells/cm$^2$ (FIG. 6A) or $2.5\times10^3$ cells/cm$^2$ (FIG. 6B) on tissue culture plates coated with protein at increasing concentrations (FIG. 6A) or at 200 nM (FIG. 6B). GRGDSP (SEQ ID NO: 24) peptides were coated at 20 μg/ml (34 mM).

The cell attachment activity of fibronectin can be duplicated by peptides containing the highly conserved, integrin-binding Arg-Gly-Asp (RGD) sequence (Pierschbacher et al., "Variants of the Cell Recognition Site of Fibronectin that Retain Attachment-Promoting Activity," *Proc. Natl. Acad. Sci. U.S.A.* 81:5985-5988 (1984), which is hereby incorporated by reference in its entirety). To further refine GST/III1H,8,10 as a fibronectin matrix mimetic, fusion proteins were engineered in which FNIII10 was deleted and instead, the adhesive RGDS sequence was inserted into FNIII8. The RGDS sequence in FNIII10 is located in a unique loop connecting β-strands F and G (Main et al., "The Three-Dimensional Structure of the Tenth Type III Module of Fibronectin: An Insight Into RGD-Mediated Interactions," *Cell* 71:671-678 (1992), which is hereby incorporated by reference in its entirety). Therefore, the FNIII10 sequence, Arg-Gly-Asp-Ser-Pro-Ala-Ser (GRGDSPAS) was inserted into the analogous site in FNIII8. Two fusion proteins were produced: (i) GST/III1H,$8^{RGD}$ (Peptide #6, FIG. 1A) and (ii) GST/III$8^{RGD}$ (Peptide #7, FIG. 1A). Cell adhesion assays were conducted to compare cell attachment activities of the RGD chimeras to the original construct, GST/III1H,8-10. Cell adhesion to surfaces coated with GST/III1H,$8^{RGD}$ was similar to that observed on GST/III1H,8-10-coated surfaces at all protein coating concentrations (FIG. 6A). Cells did not adhere to GST/III1H lacking the $8^{RGD}$ sequence (FIG. 6A). These data indicate that the adhesive activity of FNIII10 can be duplicated by inserting the RGDS-loop into FNIII8.

Figure 6B:
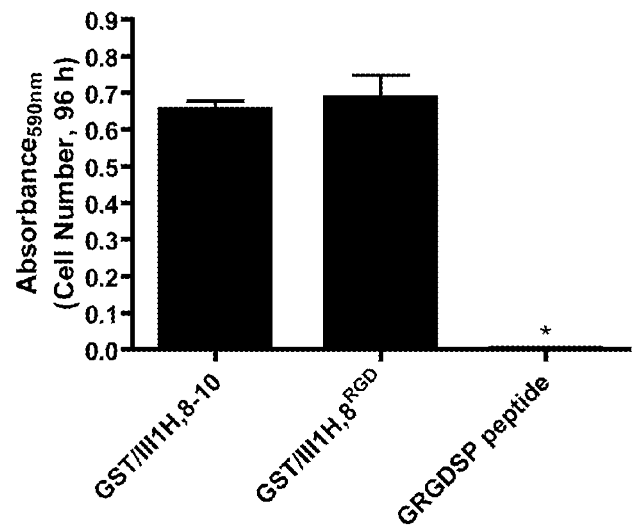

To assess the RGD-containing chimeras as growth-promoting adhesive substrates, FN-null MEFs were seeded onto wells coated with 200 nM of the various fusion proteins and cell number was determined after 96 h. Surfaces coated with GST/III1H,$8^{RGD}$ supported a similar level of cell growth as did surfaces coated with the original mimetic, GST/III1H,8-10 (FIG. 6B), and was greater than that observed with cells adherent to surfaces coated with RGD peptides alone (FIG. 6B). Of note, after 4 days, cells were no longer adherent to wells coated with GRGDSP peptides (FIG. 6B).

Figure 7A:
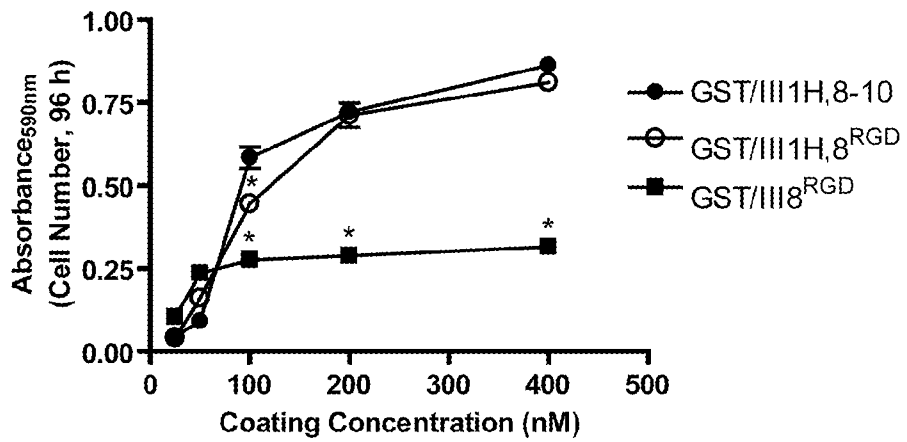
FIGS. 7A-7B depict a role of FNIII1H in the proliferative response to GST/III1H,$8^{RGD}$. FN-null MEFs were seeded at a density of $2.5\times10^3$ cells/cm$^2$ (FIG. 7A) or $1.5\times10^5$ cells/cm$^2$ (FIG. 7B) on tissue culture plates coated with recombinant fibronectin constructs at increasing concentrations (FIG. 7A) or 400 nM (FIG. 7B). Relative cell number was determined after 4 days (FIG. 7A) or cells were allowed to adhere for 30 min and attached cell number was determined (FIG. 7B). Data are expressed as mean absorbance of quadruplicate wells±SEM and represent 1 of 3 experiments. *Significantly different from GST/III1H,8-10, $p<0.05$ (ANOVA).
Figure 7B:
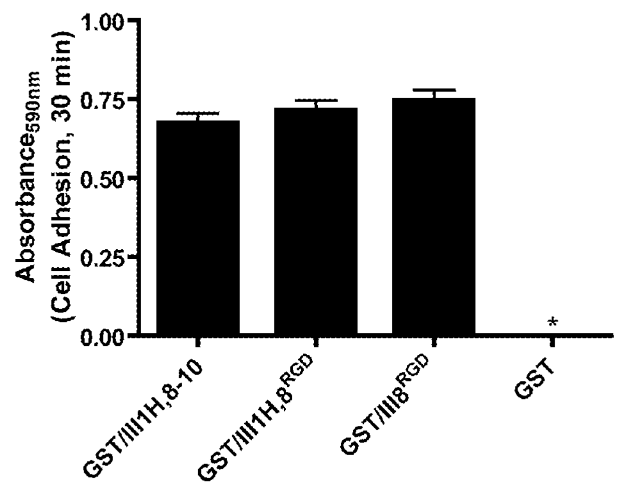
Figure 8:
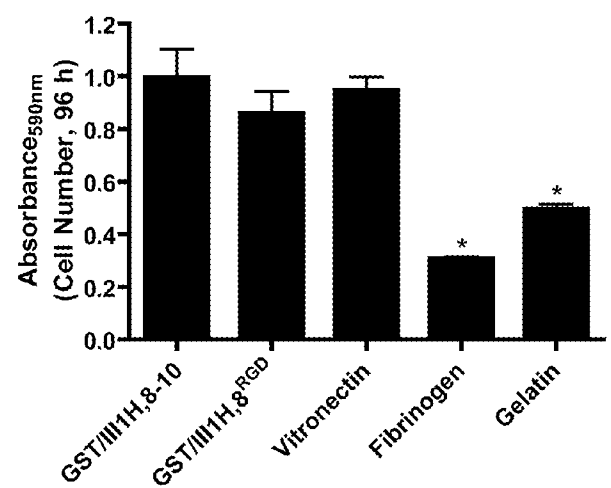
FIG. 8 shows the proliferative response to fibronectin matrix mimetics of the present invention compared to other ECM proteins. FN-null MEFs were seeded ($2.5\times10^3$ cells/cm$^2$) on tissue culture plates coated with various proteins at a concentration of 200 nM. Relative cell number was determined after 4 days. Data are expressed as mean absorbance of quadruplicate wells±SEM and represent 1 of 3 experiments. *Significantly different from GST/III1H,8-10, $p<0.05$ (ANOVA).

Dose-response studies indicate that the growth-promoting activity of GST/III1H, $8^{RGD}$ was nearly identical to that of GST/III1H,8-10 at various protein coating concentrations (FIG. 7A). Removal of FNIII1H from GST/III1H,$8^{RGD}$ (GST/III$8^{RGD}$) resulted in significantly lower cell numbers on Day 4 (FIG. 7A), providing further evidence that the heparin-binding fragment of FNIII1 is required for the enhanced cell growth response. No differences in initial cell adhesion were observed on surfaces coated with GST/III$8^{RGD}$, GST/III1H,8-10 and GST/III1H,$8^{RGD}$ (FIG. 7B). Furthermore, a comparison of the proliferative activity of the fibronectin matrix mimetics to that of other intact ECM ligands revealed that surfaces coated with GST/III1H,$8^{RGD}$ promoted cell growth to a similar extent as vitronectin-coated surfaces, and to a greater extent than that observed for fibrinogen- or gelatin-coated surfaces (FIG. 8). Taken together, these data indicate that by inserting the RGD loop into FNIII8, both FNIII9 and FNIII10 can be removed from the initial matrix mimetic without loss of cell adhesion and growth-promoting activity.

Example 5

Recombinant Fibronectin Matrix Mimetics Support Cell Migration

Figure 9A:
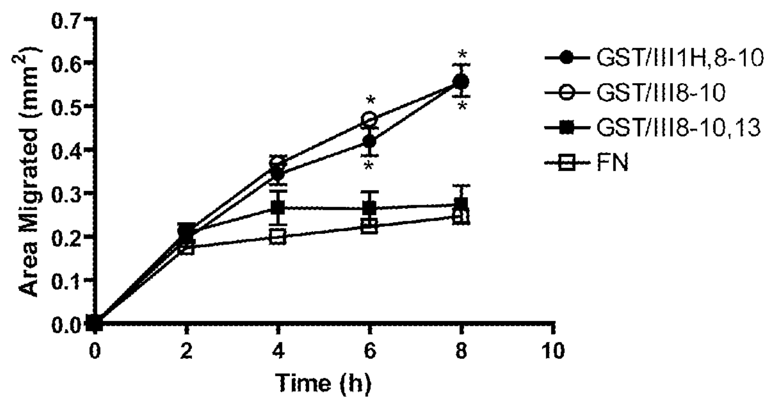
FIGS. 9A-9C demonstrate that fibronectin matrix mimetics support cell migration. FN-null MEFs were seeded ($7.4\times10^4$ cells/cm$^2$) on tissue culture plates coated with 200 nM plasma fibronectin (FN) or the various indicated recombinant fibronectin constructs. Cells were allowed to spread to confluence for 16 h (FIGS. 9A and 9B) or 4 h (FIG. 9C). Cell monolayers were wounded and images of five non-overlapping regions were obtained at 0, 2, 4, 6, and 8 hours post-wounding. Data are presented as mean area migrated at each time point±SEM and represent 1 of 3 experiments.

The ability of the recombinant fibronectin constructs to support cell migration was assessed using an in vitro assay of wound repair. FN-null MEFs were seeded at high densities onto surfaces coated with 200 nM of the various fusion proteins and allowed to form confluent monolayers. A region of the monolayer was then removed and migration of cells into the denuded space was quantified. Surfaces coated with either the original matrix mimetic (GST/III1H,8-10) or the integrin-binding fragment of fibronectin (GST/III8-10) promoted cell migration into the denuded area to a greater extent than surfaces coated with intact, plasma fibronectin (FIG. 9A). Substituting the heparin-binding module, FNIII13, for FNIII1H (see Peptide #11, FIG. 1A) decreased the rate of cell migration (GST/III1H,8-10 versus GST/III8-10,13; FIG. 9A), resulting in a rate of migration similar to that of plasma fibronectin-coated surfaces (GST/III8-10,13 versus FN; FIG. 9A).

Figure 9B:
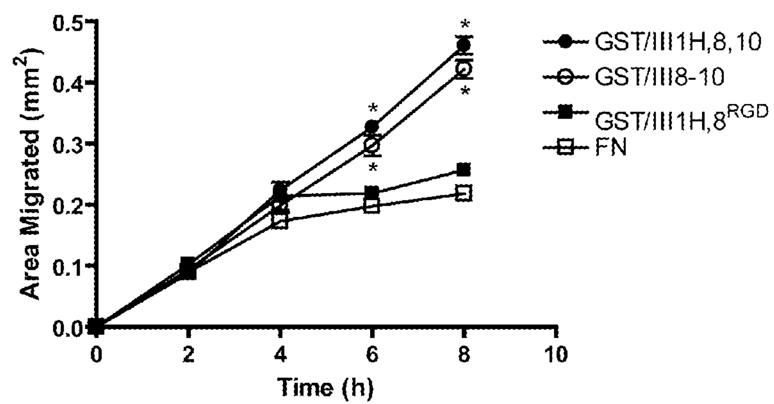
Figure 9C:
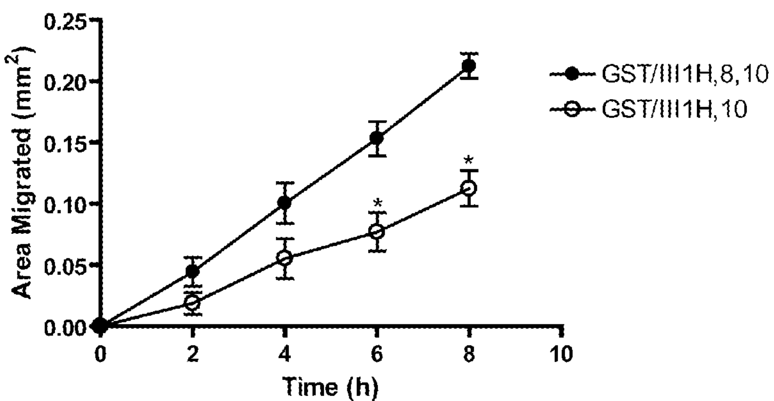

Similar to results obtained in the growth assays (FIG. 5A), removal of FNIII9 from the original matrix mimetic did not reduce the rate of cell migration, which was similar to that of the integrin-binding fragment, GST/III8-10 (GST/III1H,8,10 versus GST/III8-10, FIG. 9B). The rate of cell migration on surfaces coated with the growth-promoting, chimeric construct, GST/III1H,$8^{RGD}$, was similar to that of plasma fibronectin (FIG. 9B). Removing FNIII8 from GST/III1H,8,10 decreased the rate of cell migration (GST/III1H,10 versus GST/III1H,8,10; FIG. 9C), indicating a possible role for FNIII8 in promoting higher rates of cell migration. These data indicate that as adhesive substrates, the recombinant fibronectin matrix mimetics equal or exceed the ability of plasma fibronectin to promote cell migration.

Example 6

Fibronectin Matrix Mimetics Stimulate Collagen Gel Contraction

Figure 10:
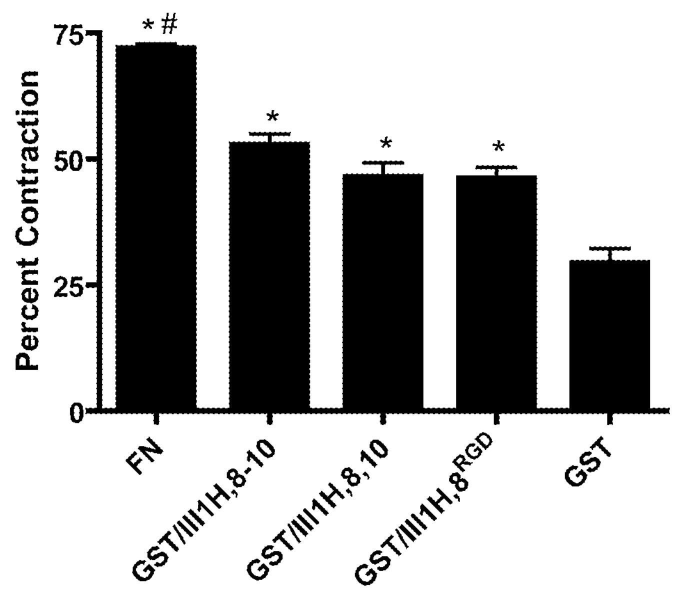
FIG. 10 shows that fibronectin matrix mimetics of the present invention stimulate collagen gel contraction. FN-null MEFs were imbedded ($2\times10^5$ cells/ml) in neutralized collagen gels in the presence of recombinant fibronectin constructs, the control protein, GST (400 nM), or plasma fibronectin (20 mg/ml; 40 nM). Collagen gel contraction was determined after 20 h as described infra in the Examples. Data are presented as average percent contraction versus 'no-cell' controls from 3 experiments performed in quadruplicate±SEM. * Significantly different from GST, $p<0.05$. # Significantly different from GST/III1H,8-10, $p<0.05$ (ANOVA).

Collagen gel contraction assays are utilized as in vitro models of collagen matrix reorganization during wound repair (Grinnell et al., "Reorganization of Hydrated Collagen Lattices by Human Skin Fibroblasts," *J. Cell Sci.* 66:51-63 (1984), which is hereby incorporated by reference in its entirety). Previous studies showed that fibronectin matrix polymerization stimulates collagen gel contraction (Hocking et al., "Stimulation of Integrin-Mediated Cell Contractility by Fibronectin Polymerization," *J. Biol. Chem.* 275:10673-10682 (2000), which is hereby incorporated by reference in its entirety) and that this activity is mimicked by the original matrix mimetic, GST/III1H,8-10 (Hocking et al., "A Cryptic Fragment From Fibronectin's III-1 Module Localizes To Lipid Rafts And Stimulates Cell Growth And Contractility," *J. Cell Biol.* 158:175-184 (2002), which is hereby incorporated by reference in its entirety). To assess the ability of the new fibronectin matrix mimetics to stimulate collagen gel contraction, FN-null MEFs were embedded in collagen gels and the extent of contraction after 20 h was determined. Addition of plasma fibronectin or the original matrix mimetic (GST/III1H,8-10) to FN-null MEFs embedded in floating collagen gels stimulated collagen gel contraction (FIG. 10). Addition of either GST/III1H,8,10 or GST/III1H,$8^{RGD}$ to cell-embedded collagen gels stimulated collagen gel contraction to a similar extent as that observed in response to the original matrix mimetic, GST/III1H,8-10 (FIG. 10). The extent of collagen gel contraction in response to GST/III1H,8,10 and GST/III1H,$8^{RGD}$ was significantly greater than that observed in response to the control protein, GST (FIG. 10).

Discussion of Examples 1-6

Described herein is the development of several recombinant fibronectin proteins that couple the "open" conformation of FNIII1 with integrin-binding sequences in order to mimic the effects of the ECM form of fibronectin on cell growth and migration. The bioactivity of the fibronectin matrix mimetics was compared to full-length, plasma fibronectin and to integrin-binding fragments and peptides. These studies show that a chimeric fibronectin fragment composed of FNIII1H and FNIII8, with the RGDS loop inserted into FNIII8, supports cell adhesion and migration, stimulates collagen gel reorganization, and displays enhanced proliferative activity over integrin-binding fibronectin fragments and other full-length ECM proteins. The growth-promoting activity in FNIII1H was localized to amino acids $Arg^{613}$, $Arg^{615}$, and $Lys^{617}$, and new evidence demonstrates that FNIII8 has cell growth- and migration-promoting properties.

Surfaces presenting the RGD-loop in FNIII8 exhibited identical adhesive activities compared to the original matrix mimetic (GST/III1H,8-10; FIG. 6A), which was comparable to that observed with integrin-binding fragments (FIG. 3B). Deleting FNIII9 from the original matrix mimetic did not decrease the proliferation response of cells (FIG. 5A) and was not required for cell migration (FIG. 9B), indicating that binding of the PHSRN sequence in FNIII9 to $\alpha5\beta1$ integrins (Aota et al., "The Short Amino Acid Sequence Pro-His-Ser-Arg-Asn in Human Fibronectin Enhances Cell-Adhesive Function," *J. Biol. Chem.* 269(40):24756-24761 (1994) and Garcia et al., "Distinct Activation States of Alpha5beta1 Integrin Show Differential Binding to RGD and Synergy Domains of Fibronectin," *Biochem.* 41(29):9063-9069 (2002), which is hereby incorporated by reference in its entirety) does not contribute to the observed activities. Surfaces coated with the chimeric RGD-construct produced higher levels of cell growth over surfaces coated with linear GRGDSP peptides (FIG. 6B), suggesting that the structural framework of the FNIII module provides support for the RGD loop to allow for higher affinity interactions with integrin receptors (Ruoslahti E, "RGD and Other Recognition Sequences for Integrins," *Annu. Rev. Cell Dev. Biol.* 12:697-715 (1996), which is hereby incorporated by reference in its entirety). The growth-promoting activity of the chimeric fibronectin matrix mimetic, than that observed for other full-length ECM substrates including fibrinogen and gelatin (FIG. 8). Thus, tethering or incorporating chimeric fibronectin matrix mimetics into biomaterials will provide robust proliferative activity to tissue-engineered scaffolds and medical devices.

The bioactivities of the fibronectin fragments tested were not identical. Surfaces coated with either GST/III1H,8-10 or GST/III1H,8,10 induced high-growth and high-migration responses; GST/III1H,$8^{RGD}$-coated surfaces provided high-growth and moderate-migration activities; GST/III8-10 induced low-growth but high-migration activities. Hence, engineering interfaces with different fibronectin matrix mimetics and fragments represents a strategy to spatially pattern different cellular responses. In contrast to results obtained in the growth studies, a large decrease in cell migration rate occurred when FNIII10 was removed and replaced by the RGD loop (compare FIG. 6B with FIG. 9B), indicating that an auxiliary site in FNIII10 (Ruoslahti E, "RGD and Other Recognition Sequences for Integrins," *Annu. Rev. Cell Dev. Biol.* 12:697-715 (1996), which is hereby incorporated by reference in its entirety) may contribute to enhanced cell migration, but not to enhanced cell growth. On the other hand, deletion of FNIII8 from GST/III1H,8-10 reduced both growth (FIG. 5A) and migration (FIG. 9C). Previous studies have identified a region within the amino-terminus of FNIII8 that is involved in cell adhesion (Aota et al., "Characterization of Regions of Fibronectin Besides the Arginine-Glycine-Aspartic Acid Sequence Required for Adhesive Function of the Cell-Binding Domain Using Site-Directed Mutagenesis," *J. Biol. Chem.* 266:15938-15943 (1991), which is hereby incorporated by reference in its entirety). Taken together, the results indicate that at least two additional sites within the cell-binding domain of fibronectin, one in FNIII10 and one in FNIII8, contribute to integrin-mediated cellular responses.

Proteolysis of the first type III repeat of fibronectin at residue $Ile^{597}$ removes both the A and B $\beta$ strands and results in a carboxyl-terminal fragment that binds to heparin (Litvinovich et al., "Reversible Unfolding of an Isolated Heparin and DNA Binding Fragment, the First Type III Module from Fibronectin," *Biochim. Biophys. Acta.* 1119:57-62 (1992), which is hereby incorporated by reference in its entirety). Previous studies localized the growth-promoting activity of GST/III1H,8-10 to the heparin-binding sequence, $K^{611}$_$R^{615}$WR_$K^{619}$. The preceding Examples herein demonstrate that FNIII1H is also required for the enhanced growth response to surfaces coated with GST/III1H,8-10 and further, pinpoint the growth-enhancing sequence in FNIII1 to $R^{613}$, $R^{615}$, and $K^{617}$. The cell surface receptor that binds to FNIII1H is currently unknown, however, it is feasible that FNIII1 interacts with cells via heparan sulfate proteoglycans (Hocking et al., "A Cryptic Fragment From Fibronectin's III-1 Module Localizes To Lipid Rafts And Stimulates Cell Growth And Contractility," *J. Cell Biol.* 158:175-184 (2002), which is hereby incorporated by reference in its entirety). Aortic smooth muscle cells adhere to surfaces coated with micromolar concentrations of a similar FNIII1 fragment, III1-C, via a heparin-dependent mechanism that involves $\alpha5\beta1$ integrins (Mercurius et al., "Cell Adhesion and Signaling on the Fibronectin 1st Type III Repeat; Requisite Roles for Cell Surface Proteoglycans and Integrins," *BMC Cell Biol.* 2:18 (2001), which is hereby incorporated by reference in its entirety). Together, these studies indicate that FNIII1H may bind either directly or indirectly to $\alpha5\beta1$ integrins via heparan sulfate proteoglycans to elicit cellular responses. In support of this, it has been shown that FNIII1H must be directly coupled to FNIII8-10 to stimulate cell growth, as individual fragments added simultaneously to cells do not have growth-promoting effects (Hocking et al., "A Cryptic Fragment From Fibronectin's III-1 Module Localizes to Lipid Rafts and Stimulates Cell Growth and Contractility," *J. Cell Biol.* 158:175-184 (2002), which is hereby incorporated by reference in its entirety). Similarly, the proliferative response to surfaces coated with a mixture of FNIII1H and FNIII8-10 fragments was not different from that observed with GST/III8-10-coated surfaces.

Fibronectin type III repeats are found in ~2% of all human proteins and show a high degree of structural similarity (Bloom et al., "FN3: A New Protein Scaffold Reaches the Clinic," *Drug Discov. Today* (19-20):949-955 (2009), which is hereby incorporated by reference in its entirety). The anti-parallel $\beta$-sheets of FNIII repeats are composed of three (A, B, and E) and four (C, D, F, and G) $\beta$ strands that overlap to form a hydrophobic core (Bork et al., "Proposed Acquisition of an Animal Protein Domain by Bacteria," *Proc. Natl. Acad. Sci. U.S.A.* 89(19):8990-8994 (1992) and Leahy et al., "Structure of a Fibronectin Type III Domain From Tenascin Phased by MAD Analysis of the Selenomethionyl Protein," *Science* 258:987-991 (1992), which are hereby incorporated by reference in their entirety), imparting a high degree of stability to the protein's structure (Litvinovich et al., "Interactions Between Type III Domains in the 110 kDa Cell-Binding Fragment of Fibronectin," *J. Mol. Biol.* 248(3):611-626 (1995), which is hereby incorporated by reference in its entirety). The six loops formed at the poles between 13 strands (termed AB, BC, etc.) are highly variable and can withstand extensive modification without loss of stability (Siggers et al., "Conformational Dynamics in Loop Swap Mutants of Homologous Fibronectin Type III Domains," *Biophys. J.* 93(7):2447-2456 (2007) and Billings et al., "Crosstalk Between the Protein Surface and Hydrophobic Core in a Core-Swapped Fibronectin Type III Domain," *J. Mol. Biol.* 375(2):560-571 (2008), which are hereby incorporated by reference in their entirety). This inherent stability likely facilitated the insertion of the RGDS sequence into the FG loop of FNIII8. The stability of fibronectin type III repeats has also allowed for the development of FNIII-domains as scaffolds for the display of binding elements (Koide et al., "The Fibronectin Type III Domain as a Scaffold for Novel Binding Proteins," *J. Mol. Biol.* 284(4):1141-1151 (1998), which is hereby incorporated by reference in its entirety), while an engineered FNIII scaffold is currently in Phase II trials as an anti-angiogenesis agent (Bloom et al., "FN3: A New Protein Scaffold Reaches the Clinic," *Drug Discov. Today* (19-20):949-955 (2009), which is hereby incorporated by reference in its entirety). Both FNIII1 and FNIII8 lack cysteine residues and post-translation modifications (Petersen et al., "Partial Primary Structure of Bovine Plasma Fibronectin: Three Types of Internal Homology," *Proc. Natl. Acad. Sci. U.S.A.* 80:137-141 (1983), which is hereby incorporated by reference in its entirety), which facilitates production in bacteria. For the studies described herein, GST/III1H,$8^{RGD}$ was generated with a cleavable GST-tag that allows for rapid purification via glutathione chromatography; yields of ~4 mg of purified GST/III1H,$8^{RGD}$ per liter of bacterial culture were obtained. The molecular mass of the chimeric matrix mimetic, excluding the GST-tag, is ~19 kDa. In contrast, the molecular mass of a single, soluble fibronectin molecule is ~500 kDa. The small size of the fibronectin matrix mimetic decreases potential immunogenicity, provides increased structure and stability over peptides, and reduces the number of binding sites for other receptors.

In conclusion, a small, chimeric fibronectin matrix mimetic has been developed by inserting the integrin-binding RGDS sequence into the FG loop of FNIII8 and then coupling FNIII$8^{RGD}$ to the heparin-binding fragment of FNIII1. Surfaces passively coated with GST/III1H,$8^{RGD}$ support cell adhesion and migration, induce collagen matrix contraction, and display enhanced proliferative activity over either integrin-binding fibronectin fragments or full-length fibronectin. These results provide proof-of-principle for the development of chimeric fibronectin type III repeats as novel adhesive ligands for synthetic biomaterials that support cell migration and stimulate high rates of cell proliferation for wound healing.

Example 7

Fibronectin Matrix Mimetics as Integrin-Specific Adhesive Substrates

Figure 11A:
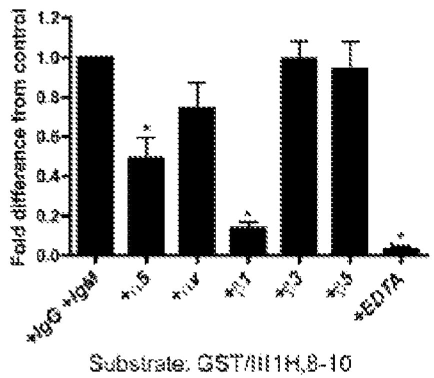
FIGS. 11A-11D show the selective integrin-mediated adhesion to fibronectin matrix mimetics. FN-null MEFs were seeded onto tissue culture plates pre-coated with 400 nM GST/III1H,8-10 (FIG. 11A), GST/III1H,8,10 (FIG. 11B), GST/III1H,8RGD (FIG. 11C), or 10 nM full-length fibronectin (FIG. 11D), in the presence of integrin function-blocking antibodies, isotype-matched control antibodies (+IgG+IgM), or EDTA. Cell adhesion was determined as described infra in the Examples. Data are compiled from 3 separate experiments each performed in triplicate. Values are represented as mean fold difference from '+IgG+IgM' control+/−SEM. *Significantly different from '+IgG+IgM', $p<0.05$ (ANOVA).
Figure 11B:
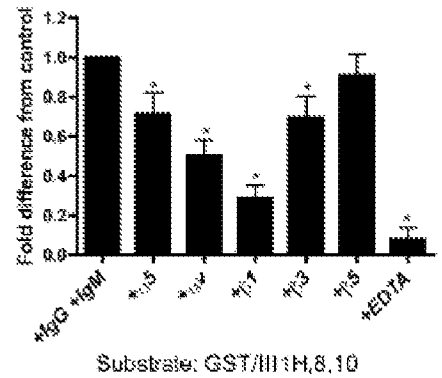
Figure 11C:
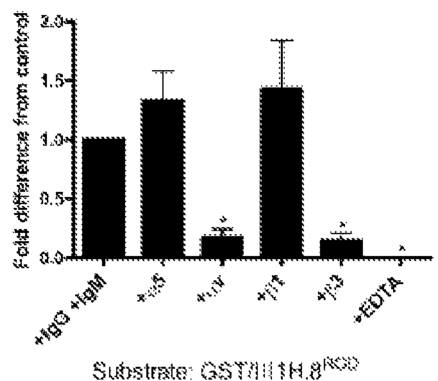
Figure 11D:
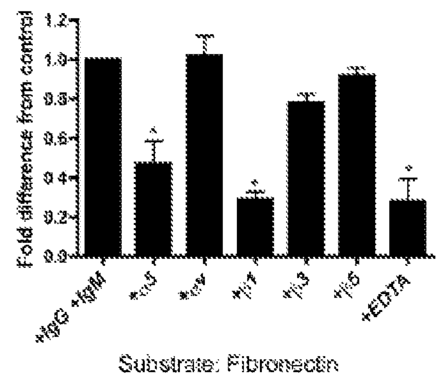

As shown supra, fibronectin matrix mimetics, GST/III1H, 8-10, GST/III1H,8,10 and GST/III1H,$8^{RGD}$ support cell adhesion, proliferation, and migration to a similar or greater extent than full-length fibronectin. FN-null MEFs were used for these studies as they do not produce endogenous fibronectin and are cultured under fibronectin- and serum-free conditions, thus allowing for direct comparison between fibronectin matrix mimetics and full-length fibronectin. To determine which integrin receptors mediate adhesion to the fibronectin matrix mimetics, various function-blocking anti-integrin antibodies were tested for their ability to block FN-null MEF attachment to protein-coated plates. Blocking antibodies directed against $\alpha5$, $\alpha v$, $\beta1$, and $\beta3$ integrins were used as these integrin subunits are expressed by FN-null MEFs and have been reported to bind full-length fibronectin (Sottile et al., "Fibronectin Matrix Assembly Enhances Adhesion-Dependent Cell Growth," *J. Cell Sci.* 111:2933-2943 (1998) and Pankov et al., "Fibronectin at a Glance," *J. Cell Sci.* 115(20):3861-3863 (2002), which are hereby incorporated by reference in their entirety). EDTA, a divalent cation chelating agent, was used to inhibit all integrin-mediated adhesion to the substrate. In the presence of $\alpha5$ or $\beta1$ integrin blocking antibodies, cell adhesion to GST/III1H,8-10-coated plates was reduced by 51.0%+/−9.49% and 86.5%+/−3.18%, respectively. In contrast, anti-$\alpha v$, -$\beta3$ or -$\beta5$ integrin antibodies had no effect on cell adhesion to GST/III1H,8-10 indicating that $\alpha5\beta1$ integrins mediate adhesion to this substrate (FIG. 11A). Cell adhesion to GST/III1H,8,10, which lacks FNIII9 and the $\alpha5\beta1$ integrin-binding synergy site, was reduced with $\alpha5$ (by 28.8%+/−10.9%), $\alpha v$ (49.8%+/−7.84%), $\beta1$ (71.0%+/−6.26%) and P3 (30.5%+/−10.7%) integrin-blocking antibodies (FIG. 11B), indicating that cell adhesion to this construct is mediated through a combination of α5β1, αvβ3 and potentially αvβ1 integrins. Cell adhesion to GST/III1H,8$^{RGD}$ was inhibited using either αv or P3 integrin blocking antibodies, by 82.7%+/−7.05% and 85.24%+/−6.09%, respectively (FIG. 11C). In contrast, addition of anti-α5 or β1 integrin antibodies had no effect on cell adhesion to GST/III1H,8$^{RGD}$, indicating that αvβ3 integrins mediate adhesion to GST/III1H,8$^{RGD}$ (FIG. 11C). In comparison, cell adhesion to full-length fibronectin was reduced only with α5 (by 53.0%+/−11.5%) and 131 (by 71.3%+/−3.97%) integrin-blocking antibodies, indicating α5β1 integrin-mediated adhesion to the fibronectin substrate (FIG. 1D). Thus, cell adhesion to both full-length fibronectin and the fibronectin matrix mimetic that has the full cell-binding domain (GST/III1H,8-10) is mediated by α5β1 integrins. Removal of FNIII9 (GST/III1H,8,10) results in cell adhesion via a combination of α5β1 and αvβ3 integrins. Further reducing the cell-binding domain by removing FNIII10 and inserting the GRGDSP loop into FNIII8 (GST/III1H,8$^{RGD}$) results in cell adhesion that is mediated exclusively by αvβ3 integrins.

Example 8

Fibronectin Matrix Assembly by Cells Adherent to Matrix Mimetics

Figure 12:
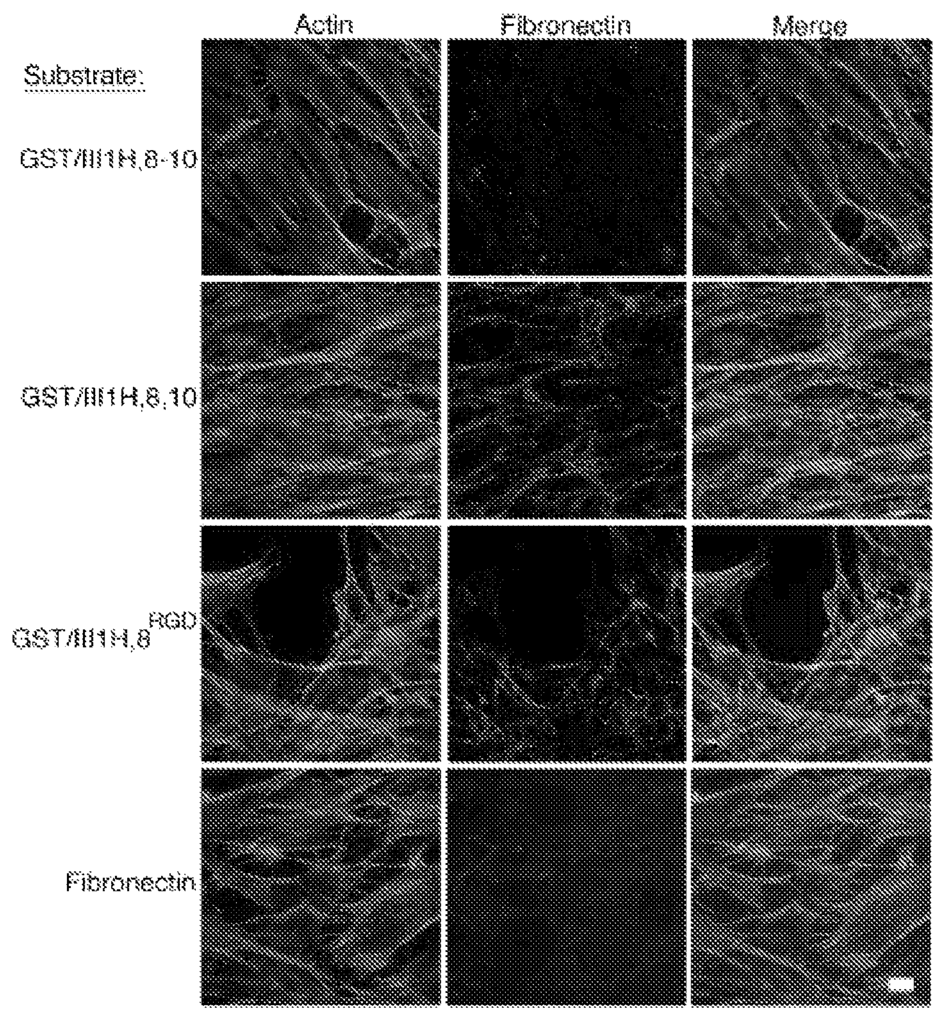
FIG. 12 shows that $\alpha v\beta 3$-binding substrates support fibronectin matrix assembly. FN-null MEFs were seeded ($3.0\times10^4$ cells/cm$^2$) onto tissue culture plates pre-coated with matrix mimetics (400 nM) or fibronectin (10 nM). Four hours after seeding, fibronectin (10 μg/ml) was added to each well, and cells were incubated for an additional 20 h. Cells were processed for immunofluorescence microscopy as described infra. Fibronectin fibrils were visualized using a polyclonal anti-fibronectin antibody. Actin was visualized using Alexa$^{488}$ labeled phalloidin. Images represent 1 of 3 experiments. Bar=10 μm.

Previous studies have shown that various adhesive substrates can either support or inhibit cell-dependent assembly of a fibronectin matrix (Bae et al., "Assembly of Exogenous Fibronectin by Fibronectin-Null Cells is Dependent on the Adhesive Substrate," *J. Biol. Chem.* 279(34):35749-35759 (2004) and Xu et al., "Display of Cell Surface Sites for Fibronectin Assembly is Modulated by Cell Adherence to (1)F3 and C-Terminal Modules of Fibronectin," *PLoS One* 4(1):e4113 (2009), which are hereby incorporated by reference in their entirety). To assess the effects of fibronectin matrix mimetic substrates on the ability of cells to assemble a fibronectin matrix, immunofluorescence microscopy was used to visualize fibronectin fibril formation by FN-null MEFs, which assemble exogenous fibronectin into ECM fibrils by mechanisms similar to those of fibronectin-expressing cells (Sottile et al., "Fibronectin Matrix Assembly Enhances Adhesion-Dependent Cell Growth," *J. Cell Sci.* 111(19):2933-2943 (1998), which is hereby incorporated by reference in its entirety). α5β1 integrin-specific substrates (GST/III1H,8-10 and fibronectin) did not support the assembly of a fibrillar fibronectin matrix (FIG. 12). In contrast, matrix mimetic substrates that bind αvβ3 integrins (GST/III1H,8,10 and GST/III1H,8$^{RGD}$) supported fibronectin fibril formation (FIG. 12).

Figures 13A, 13B, 13C:
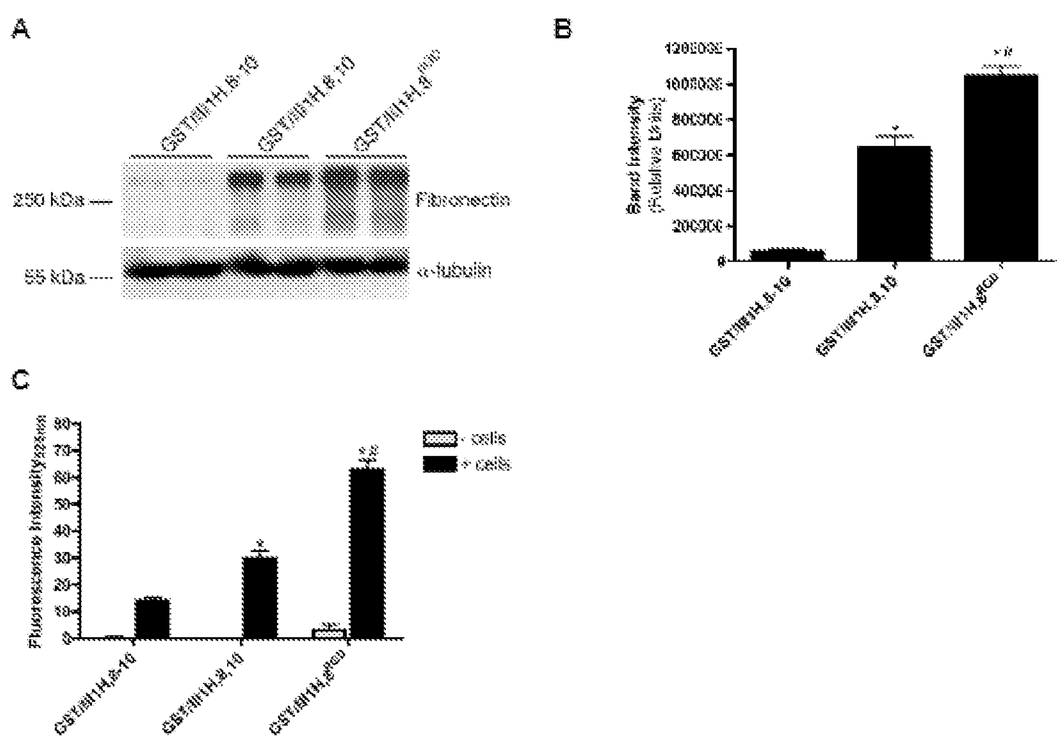
FIGS. 13A-13C show the quantification of fibronectin matrix accumulation. FN-null MEFs were seeded ($3.0\times10^4$ cells/cm$^2$) on tissue culture plates pre-coated with matrix mimetics at 400 nM. Four hours after seeding, unlabeled (FIGS. 13A and 13B) or Alexa$^{488}$-labeled (FIG. 13C) fibronectin was added at 10 μg/ml and cells were incubated for 20 h.

Fibronectin binding and deposition by FN-null MEFs adherent to matrix mimetic substrates was quantified by immunoblot analysis of cell/matrix lysates. Consistent with the immunofluorescence images shown in FIG. 12, fibronectin was absent from lysates of cells adherent to the α5β1 integrin-binding substrate, GST/III1H,8-10, but present in lysates from cells adherent to αvβ3-binding substrates (FIG. 13A). Interestingly, fibronectin deposition by cells adherent to the matrix mimetic substrate that binds solely via αvβ3 integrins (GST/III1H,8$^{RGD}$) was approximately two-fold greater than that of GST/III1H,8,10 (FIGS. 13A and 13B), which binds to cells through both αvβ3 and α5β1 integrins.

Fibronectin binding was also assessed by quantifying Alexa-labeled FN$^{488}$ accumulation by cells adherent to the various matrix mimetics. Similar to results shown in FIG. 13A, fibronectin accumulation by cells adherent to the αvβ3-binding substrates, GST/III-1H,8,10 and GST/III1H, 8$^{RGD}$, was significantly greater than that of cells adherent to GST/III1H,8-10 (FIG. 13C). In addition, the amount of fibronectin deposited by cells adherent to GST/III1H,8$^{RGD}$ was approximately twice that of cells adherent to GST/III1H,8,10 (FIG. 13C). Fluorescence intensity of cell-free, FN$^{488}$-treated wells was negligible for all substrates (FIG. 13C), indicating that FN$^{488}$ does not bind directly to the matrix mimetics. Taken together, these data indicate that cells adherent to the αvβ3 integrin-specific substrate, GST/III1H,8$^{RGD}$, incorporate significantly more fibronectin into a fibrillar matrix than GST/III1H,8,10, the α5β1 and αvβ3 integrin-binding substrate.

Example 9

ECM Collagen I Deposition by Cells Adherent to Fibronectin Matrix Mimetics

Figures 14A, 14B, 14C:
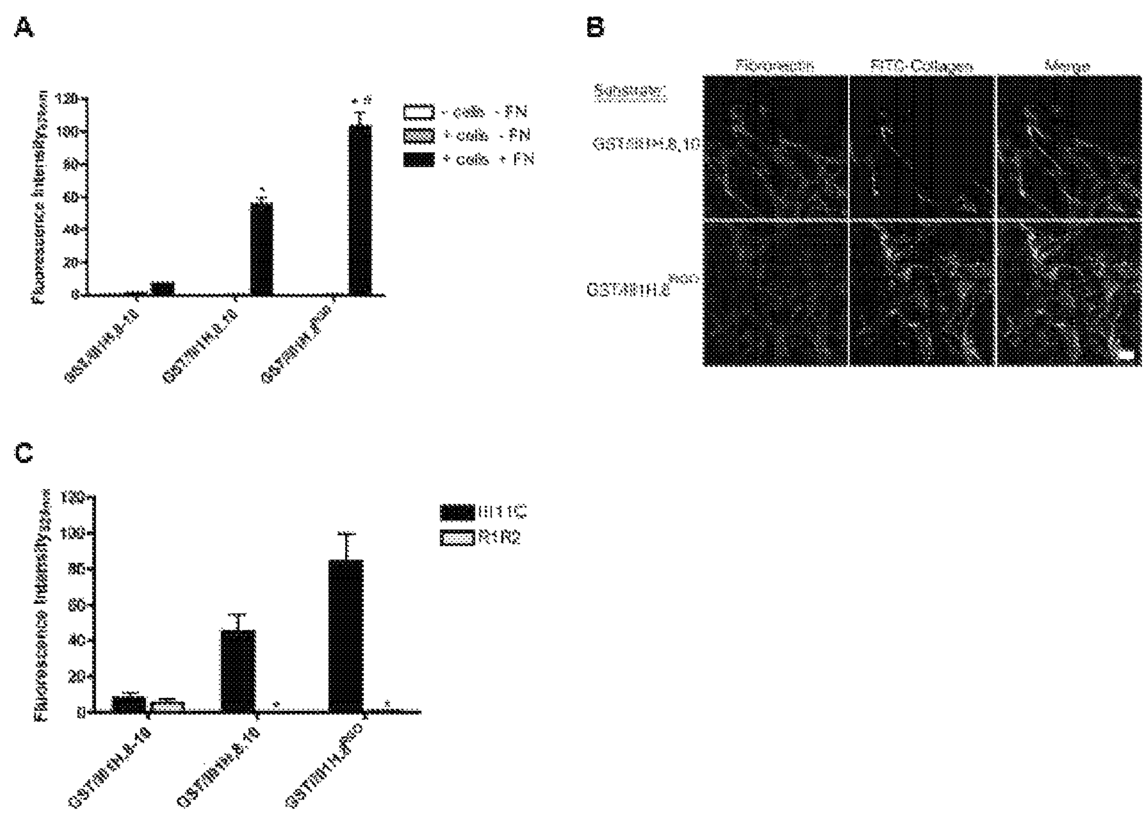
FIGS. 14A-14C show collagen I deposition by cells adherent to matrix mimetics. FN-null MEFs were seeded ($3.0\times10^4$ cells/cm$^2$) on tissue culture plates pre-coated with matrix mimetics (400 nM). Four hours after seeding, cells were treated with fibronectin (10 μg/ml) and FITC-collagen I (10 μg/ml) for 20 h.

The deposition of collagen I into the ECM is dependent on the co-assembly of a fibronectin matrix (Sottile et al., "Fibronectin Polymerization Regulates the Composition and Stability of Extracellular Matrix Fibrils and Cell-Matrix Adhesions," *Mol. Biol. Cell.* 13(10):3546-3559 (2002), which is hereby incorporated by reference in its entirety). To determine if the fibronectin matrix mimetics that support fibronectin matrix assembly also support collagen I deposition, FN-null MEFs adherent to saturating densities of matrix mimetics were incubated with FITC-labeled collagen I in the absence or presence of fibronectin. FITC-collagen I deposition was quantified 20 h after fibronectin and collagen addition. In the absence of fibronectin, FN-null MEFs adherent to the various matrix mimetics did not bind FITC-collagen I (FIG. 14A, '+cells, −FN'). Similarly, FITC-collagen I did not bind to the matrix mimetic substrates in the absence of cells (FIG. 14A, '−cells, −FN'), indicating that FITC-collagen I does not bind directly to the protein-coated plates. In the presence of soluble fibronectin, cells adherent to GST/III1H, 8-10 showed limited collagen I deposition 20 h after treatment (FIG. 14A; '+cells, +FN'). In contrast, GST/III1H,8,10 and GST/III1H,8$^{RGD}$ supported collagen I deposition by cells in the presence of fibronectin (FIG. 14A). GST/III1H,8$^{RGD}$-adherent cells treated with fibronectin showed a nearly two-fold increase in collagen I deposition compared to GST/III1H,8,10 (FIG. 14A), which was similar to the two-fold increase in fibronectin matrix deposition observed with GST/III1H,8$^{RGD}$-adherent cells (FIGS. 13B and 13C)

To determine if collagen I fibrils co-localized with fibronectin matrix fibrils, FITC-collagen I and fibronectin were visualized using immunofluorescence microscopy. FN-null MEFs adherent to GST/III1H,8,10 or GST/III1H,8$^{RGD}$ displayed collagen fibrils that co-localized extensively with fibronectin fibrils (FIG. 14B). To determine whether the interaction of collagen with fibronectin was required for collagen deposition, FITC-collagen I and fibronectin were co-incubated in the presence of the R1R2 peptide, a protein fragment that inhibits fibronectin-collagen interactions without affecting fibronectin matrix assembly (Sottile et al., "Fibronectin-Dependent Collagen I Deposition Modulates the Cell Response to Fibronectin," *Am. J. Physiol. Cell Physiol.* 293 (6):C1934-1946 (2007), which is hereby incorporated by reference in its entirety). Addition of R1R2 blocked FITC-collagen I deposition by cells adherent to GST/III1H,8,10 and GST/III1H,8$^{RGD}$ substrates (FIG. 14C). Co-incubation of fibronectin and FITC-collagen I with the control peptide, FNIII11C, had no effect on FITC-collagen I incorporation (FIG. 14C). These data indicate that fibronectin is required for collagen I deposition by cells adherent to fibronectin matrix mimetic substrates. Further, the αvβ3 integrin-binding substrate, GST/III1H,$8^{RGD}$ supports increased fibronectin and collagen I deposition into the matrix compared to substrates that have an α5β1 integrin-binding component (GST/III1H, 8-10 and GST/III1H,8,10).

Figure 15:
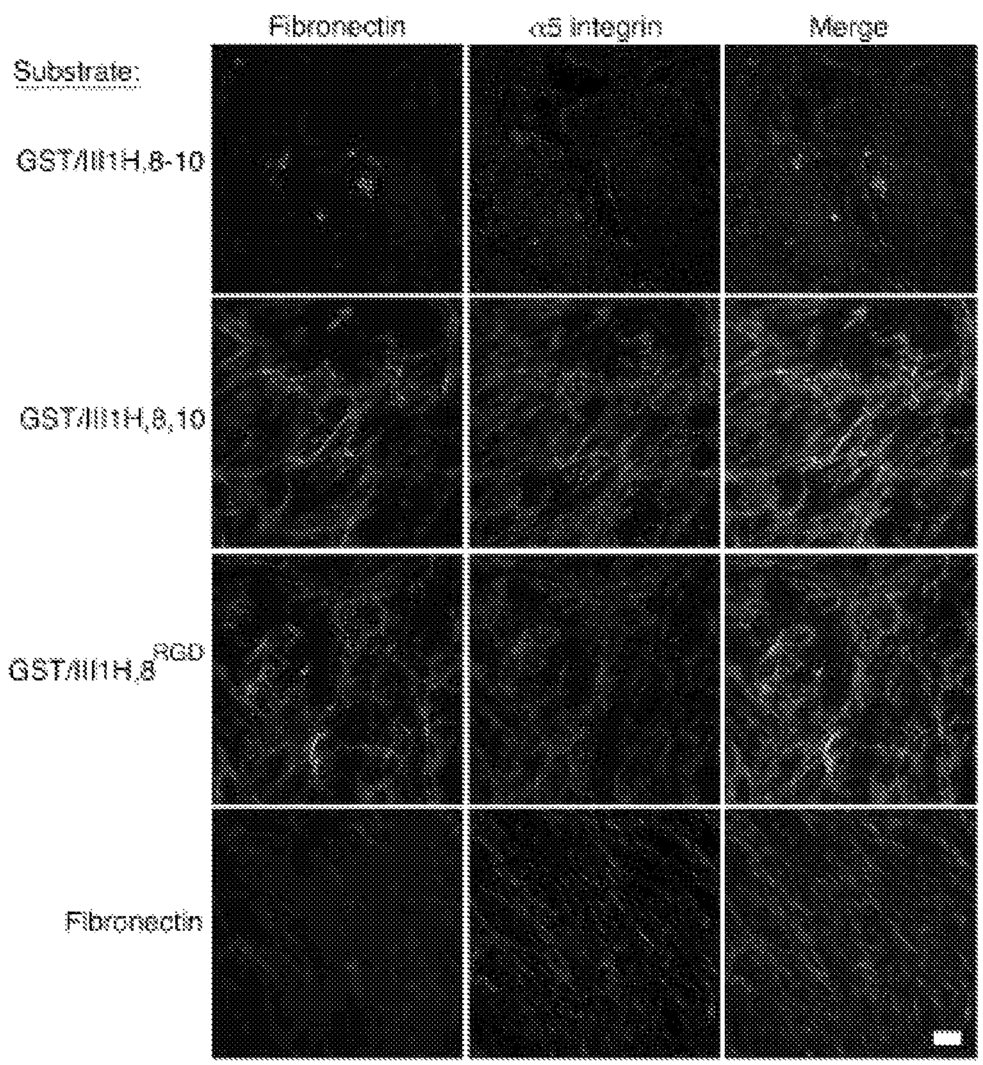
FIG. 15 shows α5β1 integrin translocation on αvβ3-binding substrates. FN-null MEFs were seeded ($3.0\times10^4$ cells/$cm^2$) on tissue culture plates pre-coated with fibronectin matrix mimetics (400 nM) or full-length fibronectin (10 nM). Four hours after seeding, soluble fibronectin (10 μg/ml) was added to each well and cells were incubated for 20 h. Cells were processed for immunofluorescence microscopy and stained using antibodies directed against fibronectin and α5 integrin. Images represent 1 of 3 experiments. Bar=10 μm.

Example 10

α5β1 Integrin Ligation and Translocation by Cells Adherent to Matrix Mimetic Substrates Upon binding of soluble fibronectin to the cell surface, α5β1 integrins translocate centripetally from focal adhesions into mature matrix adhesions (Pankov et al., "Integrin Dynamics and Matrix Assembly: Tensin-Dependent Translocation of Alpha(5)Beta(1) Integrins Promotes Early Fibronectin Fibrillogenesis," *J. Cell Biol.* 148(6):1075-1090 (2000), which is hereby incorporated by reference in its entirety). Integrin translocation along the actin cytoskeleton applies forces that unfold soluble fibronectin molecules to expose cryptic sites that allow for fibronectin multimerization and the establishment of an insoluble, fibrillar matrix (Zhong et al., "Rho-Mediated Contractility Exposes a Cryptic Site in Fibronectin and Induces Fibronectin Matrix Assembly," *J. Cell Biol.* 141:539-551 (1998); Pankov et al., "Integrin Dynamics and Matrix Assembly: Tensin-Dependent Translocation of Alpha(5)Beta(1) Integrins Promotes Early Fibronectin Fibrillogenesis," *J. Cell Biol.* 148(6):1075-1090 (2000); Danen et al., "The Fibronectin-Binding Integrins Alpha5beta1 and Alphavbeta3 Differentially Modulate RhoA-GTP Loading, Organization of Cell Matrix Adhesions, and Fibronectin Fibrillogenesis," *J. Cell Biol.* 159(6):1071-1086 (2002); and Lemmon et al., "Cell Traction Forces Direct Fibronectin Matrix Assembly," *Biophys. J.* 96(2):729-738 (2009), which are hereby incorporated by reference in their entirety). The data herein indicates the matrix mimetic substrate, GST/III1H,8-10, mediates cell adhesion through α5β1 integrins but does not support fibronectin matrix assembly. Thus, αvβ3 integrin-binding substrates (GST/III1H,8,10 and GST/III1H,$8^{RGD}$) may allow for α5β1 integrin translocation into matrix adhesions during the matrix assembly process, whereas on the GST/III1H,8-10 substrate, α5β1 integrins remain in focal adhesions and matrix assembly is inhibited. To test this possibility, immunofluorescence microscopy was used to localize α5β1 integrins on cell surfaces following fibronectin fibril formation. FN-null MEFs were seeded onto plates pre-coated with saturating densities of the fibronectin matrix mimetics, then treated with soluble fibronectin for 20 h. α5β1 integrin-specific substrates (GST/III1H,8-10 and fibronectin) did not support cell-mediated assembly of a fibronectin matrix and had α5β1 integrin localized to central and peripheral focal adhesions (FIG. 15). In contrast, α5β1 integrins co-localized with fibronectin fibrils in matrix adhesions of cells adherent to GST/III1H,8,10 and GST/III1H, $8^{RGD}$ (FIG. 15). These data indicate that α5β1 integrin translocation into fibrillar adhesions takes place only on substrates that ligate cells, at least in part, via αvβ3 integrins.

Example 11

Quantifying Substrate-Bound α5β1 Integrins

Figure 16A:
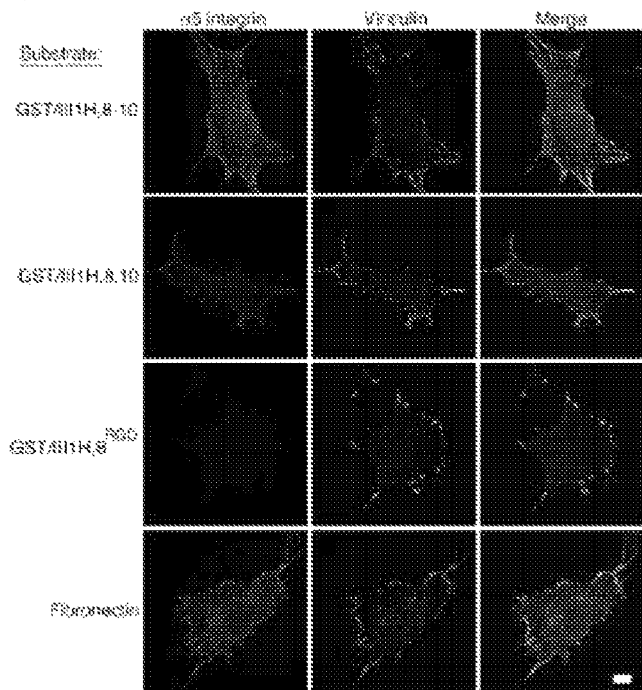
FIGS. 16A-16C show substrate-dependent ligation and clustering of α5β1 integrins. FN-null MEFs were seeded at a density of $2.5\times10^3$ cells/$cm^2$ (FIG. 16A) or $3\times10^4$ cells/$cm^2$ (FIG. 16B) onto tissue culture plates precoated with 400 nM of the various fibronectin matrix mimetics or 10 nM full-length fibronectin and allowed to adhere and spread for 4 h.

The preceding Examples indicate that saturating coating densities of GST/III1H,8,10 and GST/III1H,$8^{RGD}$ support fibronectin matrix assembly and α5β1 integrin translocation, whereas GST/III1H,8-10 and full-length fibronectin do not support matrix assembly and retain α5β1 integrins in focal adhesions after fibronectin treatment. The preceding Examples therefore indicate that upon adhesion to GST/III1H,8-10, α5β1 integrins preferentially engage the adhesive substrate instead of soluble fibronectin, thus inhibiting the initiation of the matrix assembly process. To assess α5β1 integrin clustering in response to substrate adhesion, FN-null MEFs were allowed to adhere and spread for 4 h on plates pre-coated with saturating densities of matrix mimetics in the absence of soluble fibronectin. α5β1 integrins were visualized by immunofluorescence microscopy. As expected, α5β1 integrins co-localized with vinculin in central and peripheral focal adhesions of cells adherent to both GST/III1H,8-10 and full-length fibronectin (FIG. 16A). Cells adherent to GST/III1H,8,10, which lacks the α5β1 binding site in FNIII9, showed reduced α5β1 integrin clustering compared to GST/III1H,8-10, and α5β1 integrin-containing focal adhesions were localized primarily to the cell edge (FIG. 16A). α5β1 integrin staining was completely absent from cells adherent to GST/III1H,$8^{RGD}$, despite strong vinculin staining of focal adhesions at the periphery of cells (FIG. 16A).

Figure 16B:
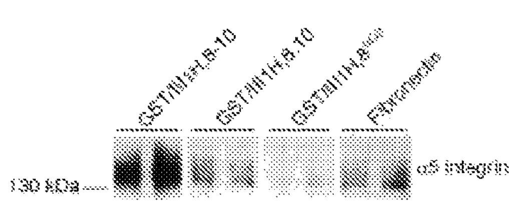
Figure 16C:
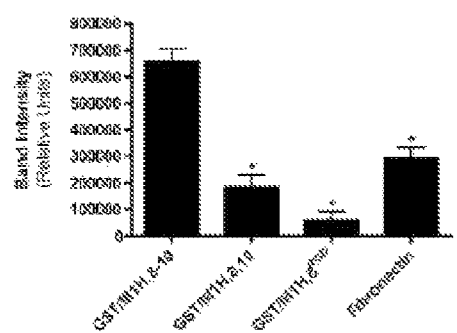

Substrate-bound α5β1 integrins were next quantified by treating adherent FN-null MEFs, in the absence of fibronectin, with a membrane-impermeable chemical cross-linker 4 h after seeding. In agreement with the immunofluorescence images shown in FIG. 16A, there was a significant increase in α5β1 integrins bound to the GST/III-1H,8-10 substrate versus GST/III1H,8,10 and GST/III1H,$8^{RGD}$ substrates (FIG. 16B-16C). Interestingly, there were fewer α5β1 integrins bound to full-length fibronectin compared to that of GST/III1H,8-10 (FIG. 16B-16C). This may be due, in part, to the fact that despite coating fibronectin at a saturating density (Sottile et al., "Fibronectin Matrix Assembly Enhances Adhesion-Dependent Cell Growth," *J. Cell Sci.* 111:2933-2943 (1998), which is hereby incorporated by reference in its entirety), there is a 20-fold difference in the molar coating concentration compared to GST/III1H,8-10. Together, these data indicate that removal of FNIII9 from GST/III1H,8-10 reduces the amount of substrate-bound α5β1 integrins.

Figures 17A, 17B, 17C:
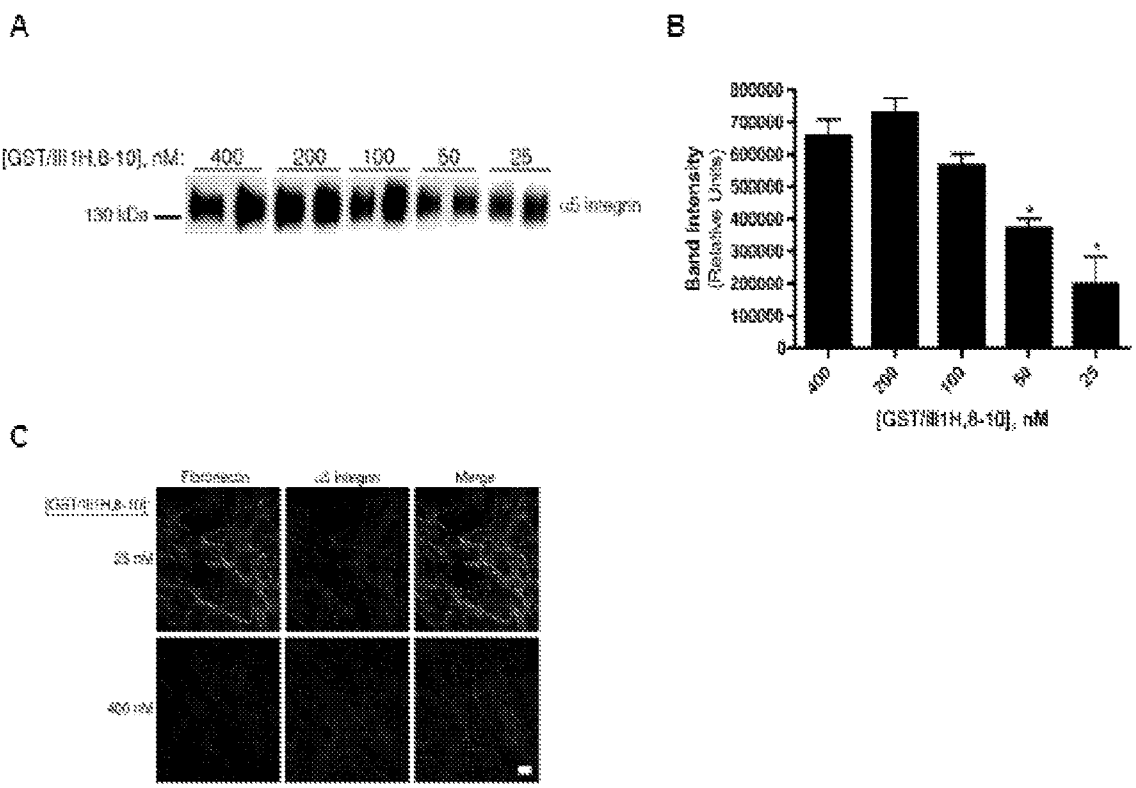
FIGS. 17A-17C show that the coating density of GST/III1H,8-10 controls fibronectin matrix assembly. FN-null MEFs were seeded ($3.0\times10^4$ cells/$cm^2$) onto tissue culture plates pre-coated with GST/III1H,8-10 at indicated concentrations. Four hours after seeding, cell surface proteins bound to the mimetic adhesive substrate were cross-linked using $BS^3$. Cells were extracted and ligated cell surface proteins were analyzed by immunoblotting with an anti-α5 integrin antibody (FIG. 17A). Immunoblot represents 1 of 3 experiments each performed in duplicate wells. α5 integrin band intensities were quantified and compiled from 3 separate experiments each performed in duplicate wells (FIG. 17B). *Significantly different from 400 nM GST/III1H,8-10, $p<0.05$ (ANOVA). Four hours after seeding, fibronectin (10 μg/ml) was added and cells were incubated an additional 20 h. Cells were processed for immunofluorescence microscopy and stained using antibodies against fibronectin and α5 integrin (FIG. 17C). Images represent 1 of 3 experiments. Bar=10 μm.

To determine if the total number of α5β1 integrin-binding sites in the mimetic substrate is a key regulator of fibronectin matrix assembly, FN-null MEFs were seeded on plates pre-coated with decreasing concentrations of GST/III1H,8-10 and substrate-bound integrins were isolated 4 h after seeding. There were no observable differences in the ability of cells to adhere and spread at any of the coating concentrations used. The amount of substrate-bound α5β1 integrin was significantly decreased when plates were coated with 25 nM and 50 nM GST/III1H,8-10 compared to 400 nM GST/III1H,8-10 (FIG. 17A-17B). These data indicate that the amount of α5β1 integrin engaged in the cell-substrate interactions is dependent on the coating density of GST/III1H,8-10.

Studies were conducted to determine whether decreasing the coating density of GST/III1H,8-10 and, thus, reducing α5β1 integrin-substrate ligation, would allow for cell-dependent fibronectin matrix assembly. FN-null MEFs adherent to wells coated with 25 nM GST/III1H,8-10 assembled a fibronectin matrix with α5β1 integrins in fibrillar adhesions (FIG. 17C), whereas cells adherent to plates coated with 400 nM GST/III1H,8-10 did not assemble fibronectin fibrils and retained α5β1 integrins in focal adhesions (FIG. 17C). Taken together, these data provide evidence that modulating the number of binding sites for α5β1 integrins in the adhesive substrate directly affects α5β1 integrin translocation and the assembly of a fibronectin matrix.

Example 12

Fibronectin Matrix Assembly and Cell Proliferation

Figures 18A, 18B:
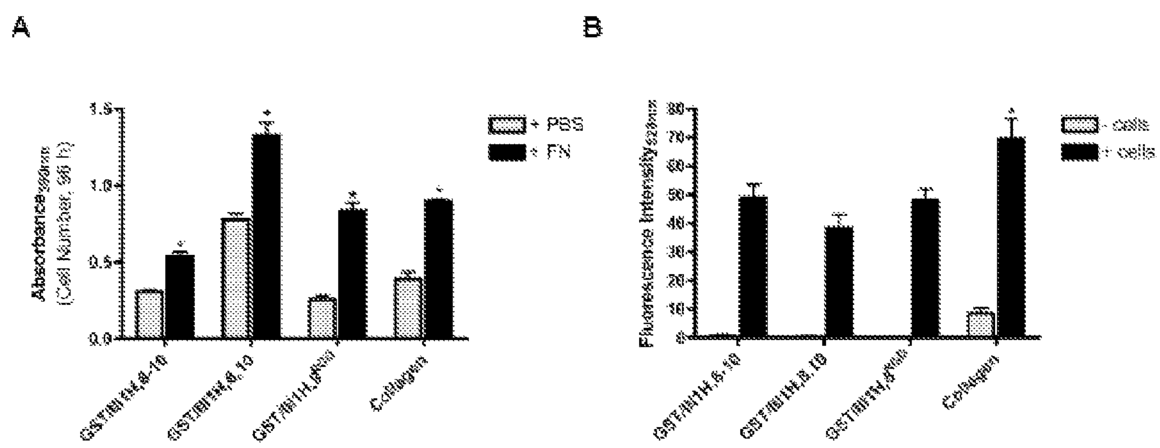
FIGS. 18A-18B show fibronectin-stimulated cell proliferation on matrix-supporting substrates. FN-null MEFs were seeded at a density of $2.5\times10^3$ cells/$cm^2$ (FIG. 18A) or $3.0\times10^4$ cells/$cm^2$ (FIG. 18B) on tissue culture plates pre-coated with matrix mimetics (50 nM) or collagen I (50 μg/ml). Four hours after seeding, fibronectin (10 μg/ml) or an equal volume of PBS was added and cells were incubated for 4 d. Cell number was determined and is shown FIG. 18A. The data are expressed as mean absorbance of triplicate wells+/−SEM and represent 1 of 3 experiments. *Significantly different from +PBS treatment, $p<0.05$ (ANOVA).

The assembly of a fibronectin matrix stimulates cell proliferation (Sottile et al., "Fibronectin Matrix Assembly Enhances Adhesion-Dependent Cell Growth," *J. Cell Sci.* 111:2933-2943 (1998), which is hereby incorporated by reference in its entirety). To determine whether the fibronectin matrix formed by FN-null cells adherent to the different fibronectin matrix mimetics similarly stimulates cell proliferation, FN-null MEFs adherent to the various fibronectin matrix mimetics were treated with soluble fibronectin and cell number was determined after 4 days. A protein coating concentration of 50 nM was used to allow for the assembly of a fibronectin matrix by cells adherent to GST/III-1H,8-10. Consistent with previous results, collagen-adherent FN-null MEFs displayed a 2.06-fold increase in cell number after 4 days with fibronectin treatment compared to cells treated with the vehicle control, PBS (FIG. 18A). Cells adherent to the $\alpha5\beta1$ integrin-binding substrate, GST/III1H,8-10 displayed a 1.54-fold increase in cell number with fibronectin treatment over PBS-treated control (FIG. 18A). GST/III1H,8,10, the $\alpha5\beta1$ and $\alpha v\beta3$ integrin-binding substrate, supported a 1.53-fold increase in cell number after 4 days with fibronectin treatment, while adhesion to the $\alpha v\beta3$ integrin-binding substrate, GST/III1H,$8^{RGD}$, resulted in a 2.90-fold increase in cell number with fibronectin treatment over the vehicle control (FIG. 18A). At this coating concentration, there were no significant differences in the amount of $FN^{488}$ deposited by cells adherent to GST/III1H,8-10, GST/III1H,8,10 or GST/III1H,$8^{RGD}$ (FIG. 18B). Together, these data demonstrate that fibronectin matrix assembly stimulates proliferation of cells adherent to fibronectin matrix mimetics. Furthermore, compared to the $\alpha5\beta1$ integrin-binding substrates (GST/III1H,8-10 and GST/III1H,8,10), the $\alpha v\beta3$ integrin-binding substrate (GST/III1H,$8^{RGD}$) supports the assembly of a more proliferative fibronectin matrix.

Example 13

FNIII1H,8,10 Promotes Wound Healing In Vivo

Figures 19A, 19B:
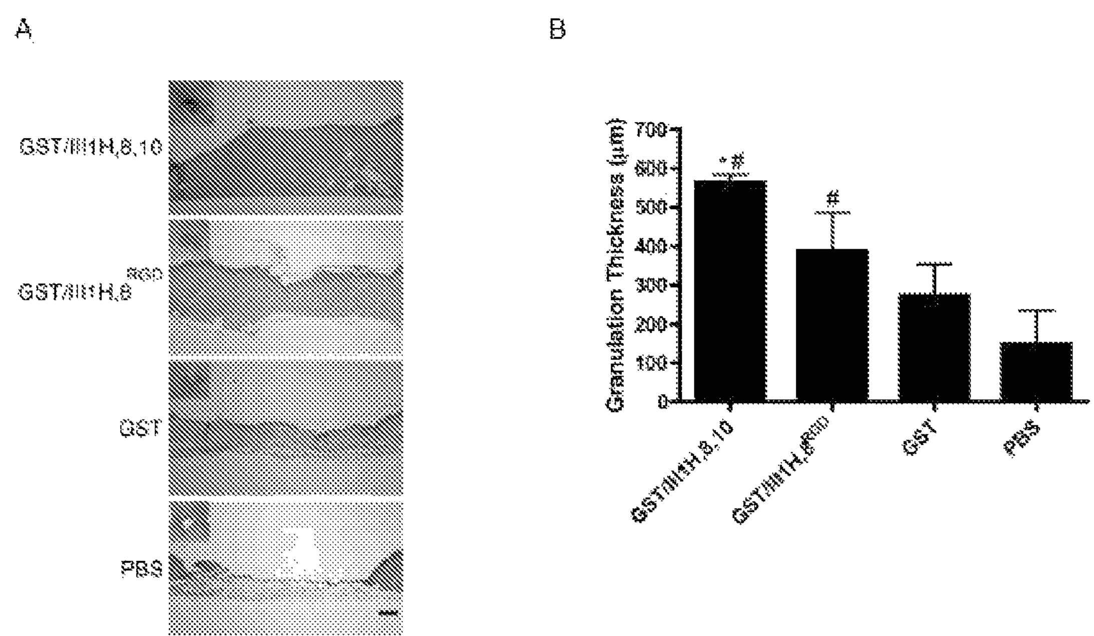
FIGS. 19A-19B show that GST/III1H,8,10 and GST/III1H,8RGD increase granulation tissue thickness in diabetic mice. Full thickness skin wounds were made on the dorsal side of C57BLKS/J-m+/+Lepr(db) mice (age 8-12 weeks) using a 6 mm biopsy punch (Miltex). Wounds were treated with either 15 μl of either mimetic or GST (25 μM diluted in PBS) or PBS alone. Wounds were sealed from the environment with a 1 cm×1 cm piece of Tegaderm™ (3M Health Care). Mice were treated with mimetics immediately following surgery as well as on days 2, 4, 7, 9, 11, 14 and 16 after surgery with new Tegaderm™ being applied following each treatment. Fourteen days (n=3) or 18 days (n=1) after wounding, the animals were sacrificed and the skin surrounding the wound was excised (FIG. 19A, inset images) and embedded in paraffin. Four-micrometer sections were cut, mounted on slides, and stained for hematoxylin and eosin. Slides were viewed using an inverted microscope (Carl Zeiss MicroImaging) with a 5× objective. Images of the wound space were obtained with a digital camera (Model Infinity 2; Lumenera) and represent 1 of 4 experiments (FIG. 19A). Bar=200 μm.

To test the effectiveness of the fibronectin peptide mimetics of the present invention to stimulate wound healing in vivo, GST/III1H,8,10 and GST/III1H,$8^{RGD}$ mimetics were administered to wounds in a genetically-diabetic mouse model. Full thickness skin wounds were made on the dorsal side of C57BLKS/J-m+/+Lepr(db) mice (age 8-12 weeks) using a 6 mm biopsy punch (Miltex). Wounds were treated with either 15 μl of fibronectin matrix mimetics or GST (25 μM diluted in PBS) or PBS alone. Wounds were sealed from the environment with a 1 cm×1 cm piece of Tegaderm (3M Health Care). Mice were treated with mimetics, GST, or PBS immediately following surgery as well as on days 2, 4, 7, 9, 11, 14 and 16 after surgery with new Tegaderm being applied following each treatment. Fourteen days (n=3) or 18 days (n=1) after wounding, the animals were sacrificed and the skin surrounding the wound was excised (FIG. 19A, inset images) and embedded in paraffin. Four-micrometer sections were cut, mounted on slides, and stained for hematoxylin and eosin. Slides were viewed using an inverted microscope (Carl Zeiss MicroImaging) with a 5× objective. Images of the wound space were obtained with a digital camera (Model Infinity 2; Lumenera) and represent 1 of 4 experiments (FIG. 19A). Bar=200 μm. As shown in FIG. 19B, granulation tissue thickness in animals administered GST/III1H,8,10 and GST/III1H, $8^{RGD}$ mimetics was significantly increased compared to animals administered PBS control. The granulation tissue thickness in animals administered GST/III1H,8,10 was also significantly increased compared to animals administered the GST control.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A recombinant fibronectin peptide mimetic comprising:

(i) at least a portion of the type III heparin-binding domain FNIII1H of fibronectin, wherein said portion comprises a heparin binding sequence and at least a portion of the type III integrin-binding domain FNIII8-10 of fibronectin, wherein said portion comprises an integrin binding sequence and wherein said portion does not contain FNIII9 in its entirety, wherein the at least a portion of the type III integrin binding domain comprises an amino acid sequence corresponding to amino acids 1266-1356 of SEQ ID NO:1 linked to amino acids 1447-1536 of SEQ ID NO: 1.

2. A recombinant fibronectin peptide mimetic comprising:

(i) at least a portion of the type III heparin-binding domain FNIII1H of fibronectin, wherein said portion comprises a heparin binding sequence and (ii) at least a portion of the type III integrin-binding domain FNIII8-10 of fibronectin, wherein said portion comprises an integrin binding sequence and wherein said portion does not contain FNIII9 in its entirety, wherein the peptide comprises-an amino acid sequence of SEQ ID NO: 3.

* * * * *

SEQUENCE LISTING

```
<160> NUMBER OF SEQ ID NOS: 41

<210> SEQ ID NO 1
<211> LENGTH: 2386
<212> TYPE: PRT
<213> ORGANISM: Homo sapiens

<400> SEQUENCE: 1

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125
```

```
Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540
```

```
Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960
```

```
Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro  Thr Asn Leu Gln Phe  Val Asn Glu
        995                 1000                 1005

Thr Asp  Ser Thr Val Leu Val  Arg Trp Thr Pro Pro  Arg Ala Gln
    1010                 1015                 1020

Ile Thr  Gly Tyr Arg Leu Thr  Val Gly Leu Thr Arg  Arg Gly Gln
    1025                 1030                 1035

Pro Arg  Gln Tyr Asn Val Gly  Pro Ser Val Ser Lys  Tyr Pro Leu
    1040                 1045                 1050

Arg Asn  Leu Gln Pro Ala Ser  Glu Tyr Thr Val Ser  Leu Val Ala
    1055                 1060                 1065

Ile Lys  Gly Asn Gln Glu Ser  Pro Lys Ala Thr Gly  Val Phe Thr
    1070                 1075                 1080

Thr Leu  Gln Pro Gly Ser Ser  Ile Pro Pro Tyr Asn  Thr Glu Val
    1085                 1090                 1095

Thr Glu  Thr Thr Ile Val Ile  Thr Trp Thr Pro Ala  Pro Arg Ile
    1100                 1105                 1110

Gly Phe  Lys Leu Gly Val Arg  Pro Ser Gln Gly Gly  Glu Ala Pro
    1115                 1120                 1125

Arg Glu  Val Thr Ser Asp Ser  Gly Ser Ile Val Val  Ser Gly Leu
    1130                 1135                 1140

Thr Pro  Gly Val Glu Tyr Val  Tyr Thr Ile Gln Val  Leu Arg Asp
    1145                 1150                 1155

Gly Gln  Glu Arg Asp Ala Pro  Ile Val Asn Lys Val  Val Thr Pro
    1160                 1165                 1170

Leu Ser  Pro Pro Thr Asn Leu  His Leu Glu Ala Asn  Pro Asp Thr
    1175                 1180                 1185

Gly Val  Leu Thr Val Ser Trp  Glu Arg Ser Thr Thr  Pro Asp Ile
    1190                 1195                 1200

Thr Gly  Tyr Arg Ile Thr Thr  Thr Pro Thr Asn Gly  Gln Gln Gly
    1205                 1210                 1215

Asn Ser  Leu Glu Glu Val Val  His Ala Asp Gln Ser  Ser Cys Thr
    1220                 1225                 1230

Phe Asp  Asn Leu Ser Pro Gly  Leu Glu Tyr Asn Val  Ser Val Tyr
    1235                 1240                 1245

Thr Val  Lys Asp Asp Lys Glu  Ser Val Pro Ile Ser  Asp Thr Ile
    1250                 1255                 1260

Ile Pro  Ala Val Pro Pro Pro  Thr Asp Leu Arg Phe  Thr Asn Ile
    1265                 1270                 1275

Gly Pro  Asp Thr Met Arg Val  Thr Trp Ala Pro Pro  Pro Ser Ile
    1280                 1285                 1290

Asp Leu  Thr Asn Phe Leu Val  Arg Tyr Ser Pro Val  Lys Asn Glu
    1295                 1300                 1305

Glu Asp  Val Ala Glu Leu Ser  Ile Ser Pro Ser Asp  Asn Ala Val
    1310                 1315                 1320

Val Leu  Thr Asn Leu Leu Pro  Gly Thr Glu Tyr Val  Val Ser Val
    1325                 1330                 1335

Ser Ser  Val Tyr Glu Gln His  Glu Ser Thr Pro Leu  Arg Gly Arg
    1340                 1345                 1350
```

```
Gln Lys  Thr Gly Leu Asp Ser  Pro Thr Gly Ile Asp  Phe Ser Asp
    1355                 1360                 1365

Ile Thr  Ala Asn Ser Phe Thr  Val His Trp Ile Ala  Pro Arg Ala
    1370                 1375                 1380

Thr Ile  Thr Gly Tyr Arg Ile  Arg His His Pro Glu  His Phe Ser
    1385                 1390                 1395

Gly Arg  Pro Arg Glu Asp Arg  Val Pro His Ser Arg  Asn Ser Ile
    1400                 1405                 1410

Thr Leu  Thr Asn Leu Thr Pro  Gly Thr Glu Tyr Val  Val Ser Ile
    1415                 1420                 1425

Val Ala  Leu Asn Gly Arg Glu  Glu Ser Pro Leu Leu  Ile Gly Gln
    1430                 1435                 1440

Gln Ser  Thr Val Ser Asp Val  Pro Arg Asp Leu Glu  Val Val Ala
    1445                 1450                 1455

Ala Thr  Pro Thr Ser Leu Leu  Ile Ser Trp Asp Ala  Pro Ala Val
    1460                 1465                 1470

Thr Val  Arg Tyr Tyr Arg Ile  Thr Tyr Gly Glu Thr  Gly Gly Asn
    1475                 1480                 1485

Ser Pro  Val Gln Glu Phe Thr  Val Pro Gly Ser Lys  Ser Thr Ala
    1490                 1495                 1500

Thr Ile  Ser Gly Leu Lys Pro  Gly Val Asp Tyr Thr  Ile Thr Val
    1505                 1510                 1515

Tyr Ala  Val Thr Gly Arg Gly  Asp Ser Pro Ala Ser  Ser Lys Pro
    1520                 1525                 1530

Ile Ser  Ile Asn Tyr Arg Thr  Glu Ile Asp Lys Pro  Ser Gln Met
    1535                 1540                 1545

Gln Val  Thr Asp Val Gln Asp  Asn Ser Ile Ser Val  Lys Trp Leu
    1550                 1555                 1560

Pro Ser  Ser Ser Pro Val Thr  Gly Tyr Arg Val Thr  Thr Thr Pro
    1565                 1570                 1575

Lys Asn  Gly Pro Gly Pro Thr  Lys Thr Lys Thr Ala  Gly Pro Asp
    1580                 1585                 1590

Gln Thr  Glu Met Thr Ile Glu  Gly Leu Gln Pro Thr  Val Glu Tyr
    1595                 1600                 1605

Val Val  Ser Val Tyr Ala Gln  Asn Pro Ser Gly Glu  Ser Gln Pro
    1610                 1615                 1620

Leu Val  Gln Thr Ala Val Thr  Asn Ile Asp Arg Pro  Lys Gly Leu
    1625                 1630                 1635

Ala Phe  Thr Asp Val Asp Val  Asp Ser Ile Lys Ile  Ala Trp Glu
    1640                 1645                 1650

Ser Pro  Gln Gly Gln Val Ser  Arg Tyr Arg Val Thr  Tyr Ser Ser
    1655                 1660                 1665

Pro Glu  Asp Gly Ile His Glu  Leu Phe Pro Ala Pro  Asp Gly Glu
    1670                 1675                 1680

Glu Asp  Thr Ala Glu Leu Gln  Gly Leu Arg Pro Gly  Ser Glu Tyr
    1685                 1690                 1695

Thr Val  Ser Val Val Ala Leu  His Asp Asp Met Glu  Ser Gln Pro
    1700                 1705                 1710

Leu Ile  Gly Thr Gln Ser Thr  Ala Ile Pro Ala Pro  Thr Asp Leu
    1715                 1720                 1725

Lys Phe  Thr Gln Val Thr Pro  Thr Ser Leu Ser Ala  Gln Trp Thr
    1730                 1735                 1740
```

```
Pro Pro  Asn Val Gln Leu Thr  Gly Tyr Arg Val Arg  Val Thr Pro
    1745                 1750                 1755

Lys Glu  Lys Thr Gly Pro Met  Lys Glu Ile Asn Leu  Ala Pro Asp
    1760                 1765                 1770

Ser Ser  Ser Val Val Val Ser  Gly Leu Met Val Ala  Thr Lys Tyr
    1775                 1780                 1785

Glu Val  Ser Val Tyr Ala Leu  Lys Asp Thr Leu Thr  Ser Arg Pro
    1790                 1795                 1800

Ala Gln  Gly Val Val Thr Thr  Leu Glu Asn Val Ser  Pro Pro Arg
    1805                 1810                 1815

Arg Ala  Arg Val Thr Asp Ala  Thr Glu Thr Thr Ile  Thr Ile Ser
    1820                 1825                 1830

Trp Arg  Thr Lys Thr Glu Thr  Ile Thr Gly Phe Gln  Val Asp Ala
    1835                 1840                 1845

Val Pro  Ala Asn Gly Gln Thr  Pro Ile Gln Arg Thr  Ile Lys Pro
    1850                 1855                 1860

Asp Val  Arg Ser Tyr Thr Ile  Thr Gly Leu Gln Pro  Gly Thr Asp
    1865                 1870                 1875

Tyr Lys  Ile Tyr Leu Tyr Thr  Leu Asn Asp Asn Ala  Arg Ser Ser
    1880                 1885                 1890

Pro Val  Val Ile Asp Ala Ser  Thr Ala Ile Asp Ala  Pro Ser Asn
    1895                 1900                 1905

Leu Arg  Phe Leu Ala Thr Thr  Pro Asn Ser Leu Leu  Val Ser Trp
    1910                 1915                 1920

Gln Pro  Pro Arg Ala Arg Ile  Thr Gly Tyr Ile Ile  Lys Tyr Glu
    1925                 1930                 1935

Lys Pro  Gly Ser Pro Pro Arg  Glu Val Val Pro Arg  Pro Arg Pro
    1940                 1945                 1950

Gly Val  Thr Glu Ala Thr Ile  Thr Gly Leu Glu Pro  Gly Thr Glu
    1955                 1960                 1965

Tyr Thr  Ile Tyr Val Ile Ala  Leu Lys Asn Asn Gln  Lys Ser Glu
    1970                 1975                 1980

Pro Leu  Ile Gly Arg Lys Lys  Thr Asp Glu Leu Pro  Gln Leu Val
    1985                 1990                 1995

Thr Leu  Pro His Pro Asn Leu  His Gly Pro Glu Ile  Leu Asp Val
    2000                 2005                 2010

Pro Ser  Thr Val Gln Lys Thr  Pro Phe Val Thr His  Pro Gly Tyr
    2015                 2020                 2025

Asp Thr  Gly Asn Gly Ile Gln  Leu Pro Gly Thr Ser  Gly Gln Gln
    2030                 2035                 2040

Pro Ser  Val Gly Gln Gln Met  Ile Phe Glu Glu His  Gly Phe Arg
    2045                 2050                 2055

Arg Thr  Thr Pro Pro Thr Thr  Ala Thr Pro Ile Arg  His Arg Pro
    2060                 2065                 2070

Arg Pro  Tyr Pro Pro Asn Val  Gly Glu Glu Ile Gln  Ile Gly His
    2075                 2080                 2085

Ile Pro  Arg Glu Asp Val Asp  Tyr His Leu Tyr Pro  His Gly Pro
    2090                 2095                 2100

Gly Leu  Asn Pro Asn Ala Ser  Thr Gly Gln Glu Ala  Leu Ser Gln
    2105                 2110                 2115

Thr Thr  Ile Ser Trp Ala Pro  Phe Gln Asp Thr Ser  Glu Tyr Ile
    2120                 2125                 2130
```

```
Ile Ser  Cys His Pro Val Gly  Thr Asp Glu Glu Pro  Leu Gln Phe
    2135                 2140                 2145

Arg Val  Pro Gly Thr Ser Thr  Ser Ala Thr Leu Thr  Gly Leu Thr
    2150                 2155                 2160

Arg Gly  Ala Thr Tyr Asn Val  Ile Val Glu Ala Leu  Lys Asp Gln
    2165                 2170                 2175

Gln Arg  His Lys Val Arg Glu  Glu Val Val Thr Val  Gly Asn Ser
    2180                 2185                 2190

Val Asn  Glu Gly Leu Asn Gln  Pro Thr Asp Asp Ser  Cys Phe Asp
    2195                 2200                 2205

Pro Tyr  Thr Val Ser His Tyr  Ala Val Gly Asp Glu  Trp Glu Arg
    2210                 2215                 2220

Met Ser  Glu Ser Gly Phe Lys  Leu Leu Cys Gln Cys  Leu Gly Phe
    2225                 2230                 2235

Gly Ser  Gly His Phe Arg Cys  Asp Ser Ser Arg Trp  Cys His Asp
    2240                 2245                 2250

Asn Gly  Val Asn Tyr Lys Ile  Gly Glu Lys Trp Asp  Arg Gln Gly
    2255                 2260                 2265

Glu Asn  Gly Gln Met Met Ser  Cys Thr Cys Leu Gly  Asn Gly Lys
    2270                 2275                 2280

Gly Glu  Phe Lys Cys Asp Pro  His Glu Ala Thr Cys  Tyr Asp Asp
    2285                 2290                 2295

Gly Lys  Thr Tyr His Val Gly  Glu Gln Trp Gln Lys  Glu Tyr Leu
    2300                 2305                 2310

Gly Ala  Ile Cys Ser Cys Thr  Cys Phe Gly Gly Gln  Arg Gly Trp
    2315                 2320                 2325

Arg Cys  Asp Asn Cys Arg Arg  Pro Gly Gly Glu Pro  Ser Pro Glu
    2330                 2335                 2340

Gly Thr  Thr Gly Gln Ser Tyr  Asn Gln Tyr Ser Gln  Arg Tyr His
    2345                 2350                 2355

Gln Arg  Thr Asn Thr Asn Val  Asn Cys Pro Ile Glu  Cys Phe Met
    2360                 2365                 2370

Pro Leu  Asp Val Gln Ala Asp  Arg Glu Asp Ser Arg  Glu
    2375                 2380                 2385
```

<210> SEQ ID NO 2
<211> LENGTH: 8815
<212> TYPE: DNA
<213> ORGANISM: Homo sapiens

<400> SEQUENCE: 2

```
gcccgcgccg gctgtgctgc acagggggag gagagggaac cccaggcgcg agcgggaaga     60

ggggacctgc agccacaact tctctggtcc tctgcatccc ttctgtccct ccacccgtcc    120

ccttccccac cctctggccc ccaccttctt ggaggcgaca acccccggga ggcattagaa    180

gggatttttc ccgcaggttg cgaagggaag caaacttggt ggcaacttgc ctcccggtgc    240

gggcgtctct cccccaccgt ctcaacatgc ttaggggtcc ggggcccggg ctgctgctgc    300

tggccgtcca gtgcctgggg acagcggtgc cctccacggg agcctcgaag agcaagaggc    360

aggctcagca aatggttcag ccccagtccc cggtggctgt cagtcaaagc aagcccggtt    420

gttatgacaa tggaaaacac tatcagataa atcaacagtg ggagcggacc tacctaggca    480

atgcgttggt ttgtacttgt tatggaggaa gccgaggttt taactgcgag agtaaacctg    540

aagctgaaga gacttgcttt gacaagtaca ctgggaacac ttaccgagtg ggtgacactt    600
```

-continued

```
atgagcgtcc taaagactcc atgatctggg actgtacctg catcggggct gggcgaggga    660
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct cacccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattggag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatggggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
```

```
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cgggctgtcc cctggggtca   3180
cctattactt caaagtcttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccagggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agaggtgccc caactcactg   4080
acctaagctt tgttgatata accgattcaa gcatcggcct gaggtggacc ccgctaaact   4140
cttccaccat tattgggtac cgcatcacag tagttgcggc aggagaaggt atccctattt   4200
ttgaagattt tgtggactcc tcagtaggat actacacagt cacagggctg gagccgggca   4260
ttgactatga tatcagcgtt atcactctca ttaatggcgg cgagagtgcc cctactacac   4320
tgacacaaca aacggctgtt cctcctccca ctgacctgcg attcaccaac attggtccag   4380
acaccatgcg tgtcacctgg gctccacccc catccattga tttaaccaac ttcctggtgc   4440
gttactcacc tgtgaaaaat gaggaagatg ttgcagagtt gtcaatttct ccttcagaca   4500
atgcagtggt cttaacaaat ctcctgcctg gtacagaata tgtagtgagt gtctccagtg   4560
tctacgaaca acatgagagc acacctctta gaggaagaca gaaaacaggt cttgattccc   4620
caactggcat tgacttttct gatattactg ccaactcttt tactgtgcac tggattgctc   4680
ctcgagccac catcactggc tacaggatcc gccatcatcc cgagcacttc agtgggagac   4740
ctcgagaaga tcgggtgccc cactctcgga attccatcac cctcaccaac ctcactccag   4800
gcacagagta tgtggtcagc atcgttgctc ttaatggcag agaggaaagt cccttattga   4860
ttggccaaca atcaacagtt tctgatgttc cgagggacct ggaagttgtt gctgcgaccc   4920
ccaccagcct actgatcagc tgggatgctc ctgctgtcac agtgagatat tacaggatca   4980
cttacggaga gacaggagga aatagccctg tccaggagtt cactgtgcct gggagcaagt   5040
ctacagctac catcagcggc cttaaacctg gagttgatta taccatcact gtgtatgctg   5100
tcactggccg tggagacagc cccgcaagca gcaagccaat ttccattaat taccgaacag   5160
aaattgacaa accatcccag atgcaagtga ccgatgttca ggacaacagc attagtgtca   5220
agtggctgcc ttcaagttcc cctgttactg gttacagagt aaccaccact cccaaaaatg   5280
gaccaggacc aacaaaaact aaaactgcag gtccagatca aacagaaatg actattgaag   5340
gcttgcagcc cacagtggag tatgtggtta gtgtctatgc tcagaatcca agcggagaga   5400
```

```
gtcagcctct ggttcagact gcagtaacca acattgatcg ccctaaagga ctggcattca   5460
ctgatgtgga tgtcgattcc atcaaaattg cttgggaaag cccacagggg caagtttcca   5520
ggtacagggt gacctactcg agccctgagg atggaatcca tgagctattc cctgcacctg   5580
atggtgaaga agacactgca gagctgcaag gcctcagacc gggttctgag tacacagtca   5640
gtgtggttgc cttgcacgat gatatggaga gccagcccct gattggaacc cagtccacag   5700
ctattcctgc accaactgac ctgaagttca ctcaggtcac acccacaagc ctgagcgccc   5760
agtggacacc acccaatgtt cagctcactg gatatcgagt gcgggtgacc cccaaggaga   5820
agaccggacc aatgaaagaa atcaaccttg ctcctgacag ctcatccgtg gttgtatcag   5880
gacttatggt ggccaccaaa tatgaagtga gtgtctatgc tcttaaggac actttgacaa   5940
gcagaccagc tcagggagtt gtcaccactc tggagaatgt cagcccacca agaagggctc   6000
gtgtgacaga tgctactgag accaccatca ccattagctg gagaaccaag actgagacga   6060
tcactggctt ccaagttgat gccgttccag ccaatggcca gactccaatc cagagaacca   6120
tcaagccaga tgtcagaagc tacaccatca caggtttaca accaggcact gactacaaga   6180
tctacctgta caccttgaat gacaatgctc ggagctcccc tgtggtcatc gacgcctcca   6240
ctgccattga tgcaccatcc aacctgcgtt tcctggccac cacacccaat tccttgctgg   6300
tatcatggca gccgccacgt gccaggatta ccggctacat catcaagtat gagaagcctg   6360
ggtctcctcc cagagaagtg gtccctcggc cccgccctgg tgtcacagag gctactatta   6420
ctggcctgga accgggaacc gaatatacaa tttatgtcat tgccctgaag aataatcaga   6480
agagcgagcc cctgattgga aggaaaaaga cagacgagct tccccaactg gtaacccttc   6540
cacaccccaa tcttcatgga ccagagatct tggatgttcc ttccacagtt caaaagaccc   6600
ctttcgtcac ccaccctggg tatgacactg gaaatggtat tcagcttcct ggcacttctg   6660
gtcagcaacc cagtgttggg caacaaatga tctttgagga acatggtttt aggcggacca   6720
caccgcccac aacggccacc cccataaggc ataggccaag accatacccg ccgaatgtag   6780
gtgaggaaat ccaaattggt cacatcccca gggaagatgt agactatcac ctgtacccac   6840
acggtccggg actcaatcca aatgcctcta caggacaaga agctctctct cagacaacca   6900
tctcatgggc cccattccag gacacttctg agtacatcat ttcatgtcat cctgttggca   6960
ctgatgaaga acccttacag ttcagggttc ctggaacttc taccagtgcc actctgacag   7020
gcctcaccag aggtgccacc tacaacatca tagtggaggc actgaaagac cagcagaggc   7080
ataaggttcg ggaagaggtt gttaccgtgg gcaactctgt caacgaaggc ttgaaccaac   7140
ctacggatga ctcgtgcttt gacccctaca cagtttccca ttatgccgtt ggagatgagt   7200
gggaacgaat gtctgaatca ggctttaaac tgttgtgcca gtgcttaggc tttggaagtg   7260
gtcatttcag atgtgattca tctagatggt gccatgacaa tggtgtgaac tacaagattg   7320
gagagaagtg ggaccgtcag ggagaaaatg gccagatgat gagctgcaca tgtcttggga   7380
acggaaaagg agaattcaag tgtgaccctc atgaggcaac gtgttatgat gatgggaaga   7440
cataccacgt aggagaacag tggcagaagg aatatctcgg tgccatttgc tcctgcacat   7500
gctttggagg ccagcggggc tggcgctgtg acaactgccg cagacctggg ggtgaaccca   7560
gtcccgaagg cactactggc cagtcctaca accagtattc tcagagatac catcagagaa   7620
caaacactaa tgttaattgc ccaattgagt gcttcatgcc tttagatgta caggctgaca   7680
gagaagattc ccgagagtaa atcatctttc caatccagag gaacaagcat gtctctctgc   7740
caagatccat ctaaactgga gtgatgttag cagacccagc ttagagttct tctttcttc   7800
```

```
ttaagccctt tgctctggag gaagttctcc agcttcagct caactcacag cttctccaag   7860

catcaccctg ggagtttcct gagggttttc tcataaatga gggctgcaca ttgcctgttc   7920

tgcttcgaag tattcaatac cgctcagtat tttaaatgaa gtgattctaa gatttggttt   7980

gggatcaata ggaaagcata tgcagccaac caagatgcaa atgttttgaa atgatatgac   8040

caaaatttta agtaggaaag tcacccaaac acttctgctt tcacttaagt gtctggcccg   8100

caatactgta ggaacaagca tgatcttgtt actgtgatat tttaaatatc cacagtactc   8160

actttttcca aatgatccta gtaattgcct agaaatatct ttctcttacc tgttatttat   8220

caatttttcc cagtattttt atacggaaaa aattgtattg aaaacactta gtatgcagtt   8280

gataagagga atttggtata attatggtgg gtgattattt tttatactgt atgtgccaaa   8340

gctttactac tgtggaaaga caactgtttt aataaaagat ttacattcca caacttgaag   8400

ttcatctatt tgatataaga caccttcggg ggaaataatt cctgtgaata ttctttttca   8460

attcagcaaa catttgaaaa tctatgatgt gcaagtctaa ttgttgattt cagtacaaga   8520

ttttctaaat cagttgctac aaaaactgat tggtttttgt cacttcatct cttcactaat   8580

ggagatagct ttacactttc tgctttaata gatttaagtg gaccccaata tttattaaaa   8640

ttgctagttt accgttcaga agtataatag aaataatctt tagttgctct tttctaacca   8700

ttgtaattct tcccttcttc cctccacctt tccttcattg aataaacctc tgttcaaaga   8760

gattgcctgc aagggaaata aaaatgacta agatattaaa aaaaaaaaaa aaaaa        8815
```

```
<210> SEQ ID NO 3
<211> LENGTH: 258
<212> TYPE: PRT
<213> ORGANISM: artificial
<220> FEATURE:
<223> OTHER INFORMATION: FNIII1H, 8, 10

<400> SEQUENCE: 3

Ile Gln Trp Asn Ala Pro Gln Pro Ser His Ile Ser Lys Tyr Ile Leu
1               5                   10                  15

Arg Trp Arg Pro Lys Asn Ser Val Gly Arg Trp Lys Glu Ala Thr Ile
            20                  25                  30

Pro Gly His Leu Asn Ser Tyr Thr Ile Lys Gly Leu Lys Pro Gly Val
        35                  40                  45

Val Tyr Glu Gly Gln Leu Ile Ser Ile Gln Gln Tyr Gly His Gln Glu
    50                  55                  60

Val Thr Arg Phe Asp Phe Thr Thr Thr Ser Thr Ser Thr Ala Val Pro
65                  70                  75                  80

Pro Pro Thr Asp Leu Arg Phe Thr Asn Ile Gly Pro Asp Thr Met Arg
                85                  90                  95

Val Thr Trp Ala Pro Pro Pro Ser Ile Asp Leu Thr Asn Phe Leu Val
            100                 105                 110

Arg Tyr Ser Pro Val Lys Asn Glu Glu Asp Val Ala Glu Leu Ser Ile
        115                 120                 125

Ser Pro Ser Asp Asn Ala Val Val Leu Thr Asn Leu Leu Pro Gly Thr
    130                 135                 140

Glu Tyr Val Val Ser Val Ser Ser Val Tyr Glu Gln His Glu Ser Thr
145                 150                 155                 160

Pro Leu Arg Gly Arg Gln Lys Thr Val Ser Asp Val Pro Arg Asp Leu
                165                 170                 175

Glu Val Val Ala Ala Thr Pro Thr Ser Leu Leu Ile Ser Trp Asp Ala
            180                 185                 190
```

```
Pro Ala Val Thr Val Arg Tyr Tyr Arg Ile Thr Tyr Gly Glu Thr Gly
        195                 200                 205

Gly Asn Ser Pro Val Gln Glu Phe Thr Val Pro Gly Ser Lys Ser Thr
    210                 215                 220

Ala Thr Ile Ser Gly Leu Lys Pro Gly Val Asp Tyr Thr Ile Thr Val
225                 230                 235                 240

Tyr Ala Val Thr Gly Arg Gly Asp Ser Pro Ala Ser Ser Lys Pro Ile
                245                 250                 255

Ser Ile


<210> SEQ ID NO 4
<211> LENGTH: 792
<212> TYPE: DNA
<213> ORGANISM: artificial
<220> FEATURE:
<223> OTHER INFORMATION: FNIII1H, 8, 10

<400> SEQUENCE: 4

atccagtgga atgcaccaca gccatctcac atttccaagt acattctcag gtggagacct     60

aaaaattctg taggccgttg gaaggaagct accataccag gccacttaaa ctcctacacc    120

atcaaaggcc tgaagcctgg tgtggtatac gagggccagc tcatcagcat ccagcagtac    180

ggccaccaag aagtgactcg ctttgacttc accaccacca gcaccagcac aggatctgct    240

gttcctcctc ccactgacct gcgattcacc aacattggtc cagacaccat gcgtgtcacc    300

tgggctccac ccccatccat tgatttaacc aacttcctgg tgcgttactc acctgtgaaa    360

aatgaggaag atgttgcaga gttgtcaatt tctccttcag acaatgcagt ggtcttaaca    420

aatctcctgc ctggtacaga atatgtagtg agtgtctcca gtgtctacga acaacatgag    480

agcacacctc ttagaggaag acagaaaaca gtttctgatg ttccgaggga cctggaagtt    540

gttgctgcga cccccaccag cctactgatc agctgggatg ctcctgctgt cacagtgaga    600

tattacagga tcacttacgg agaaacagga ggaaatagcc ctgtccagga gttcactgtg    660

cctgggagca agtctacagc taccatcagc ggccttaaac ctggagttga ttataccatc    720

actgtgtatg ctgtcactgg ccgtggagac agccccgcaa gcagcaagcc aatttccatt    780

aattaccgaa ca                                                        792


<210> SEQ ID NO 5
<211> LENGTH: 786
<212> TYPE: DNA
<213> ORGANISM: artificial
<220> FEATURE:
<223> OTHER INFORMATION: FNIIIH, 8, 10

<400> SEQUENCE: 5

atccagtgga atgcaccaca gccatctcac atttccaagt acattctcag gtggagacct     60

aaaaattctg taggccgttg gaaggaagct accataccag gccacttaaa ctcctacacc    120

atcaaaggcc tgaagcctgg tgtggtatac gagggccagc tcatcagcat ccagcagtac    180

ggccaccaag aagtgactcg ctttgacttc accaccacca gcaccagcac agctgttcct    240

cctcccactg acctgcgatt caccaacatt ggtccagaca ccatgcgtgt cacctgggct    300

ccacccccat ccattgattt aaccaacttc ctggtgcgtt actcacctgt gaaaaatgag    360

gaagatgttg cagagttgtc aatttctcct tcagacaatg cagtggtctt aacaaatctc    420

ctgcctggta cagaatatgt agtgagtgtc tccagtgtct acgaacaaca tgagagcaca    480

cctcttagag gaagacagaa aacagtttct gatgttccga gggacctgga agttgttgct    540
```

```
gcgaccccca ccagcctact gatcagctgg gatgctcctg ctgtcacagt gagatattac    600

aggatcactt acggagaaac aggaggaaat agccctgtcc aggagttcac tgtgcctggg    660

agcaagtcta cagctaccat cagcggcctt aaacctggag ttgattatac catcactgtg    720

tatgctgtca ctggccgtgg agacagcccc gcaagcagca agccaatttc cattaattac    780

cgaaca                                                                786


<210> SEQ ID NO 6
<211> LENGTH: 81
<212> TYPE: PRT
<213> ORGANISM: artificial
<220> FEATURE:
<223> OTHER INFORMATION: FNIII1H, RGD

<400> SEQUENCE: 6

Ile Gln Trp Asn Ala Pro Gln Pro Ser His Ile Ser Lys Tyr Ile Leu
1               5                   10                  15

Arg Trp Arg Pro Lys Asn Ser Val Gly Arg Trp Lys Glu Ala Thr Ile
            20                  25                  30

Pro Gly His Leu Asn Ser Tyr Thr Ile Lys Gly Leu Lys Pro Gly Val
        35                  40                  45

Val Tyr Glu Gly Gln Leu Ile Ser Ile Gln Gly Arg Gly Asp Ser Pro
    50                  55                  60

Ala Ser Gln Glu Val Thr Arg Phe Asp Phe Thr Thr Thr Ser Thr Ser
65                  70                  75                  80

Thr


<210> SEQ ID NO 7
<211> LENGTH: 243
<212> TYPE: DNA
<213> ORGANISM: artificial
<220> FEATURE:
<223> OTHER INFORMATION: FNIII1H, RGD

<400> SEQUENCE: 7

atccagtgga atgcaccaca gccatctcac atttccaagt acattctcag gtggagacct     60

aaaaattctg taggccgttg gaaggaagct accataccag gccacttaaa ctcctacacc    120

atcaaaggcc tgaagcctgg tgtggtatac gagggccagc tcatatcgat tcagggccgt    180

ggagactcgc cggcaagcca agaagtgact cgctttgact tcaccaccac cagcaccagc    240

aca                                                                  243


<210> SEQ ID NO 8
<211> LENGTH: 243
<212> TYPE: DNA
<213> ORGANISM: artificial
<220> FEATURE:
<223> OTHER INFORMATION: FNIII1H, RGD

<400> SEQUENCE: 8

atccagtgga atgcaccaca gccatctcac atttccaagt acattctcag gtggagacct     60

aaaaattctg taggccgttg gaaggaagct accataccag gccacttaaa ctcctacacc    120

atcaaaggcc tgaagcctgg tgtggtatac gagggccagc tcatcagcat ccagggccgt    180

ggagactcgc cggcaagcca agaagtgact cgctttgact tcaccaccac cagcaccagc    240

aca                                                                  243
```

<210> SEQ ID NO 9
<211> LENGTH: 172
<212> TYPE: PRT
<213> ORGANISM: artificial
<220> FEATURE:
<223> OTHER INFORMATION: FNIII1H, 8RGD

<400> SEQUENCE: 9

```
Ile Gln Trp Asn Ala Pro Gln Pro Ser His Ile Ser Lys Tyr Ile Leu
1               5                   10                  15

Arg Trp Arg Pro Lys Asn Ser Val Gly Arg Trp Lys Glu Ala Thr Ile
            20                  25                  30

Pro Gly His Leu Asn Ser Tyr Thr Ile Lys Gly Leu Lys Pro Gly Val
        35                  40                  45

Val Tyr Glu Gly Gln Leu Ile Ser Ile Gln Gln Tyr Gly His Gln Glu
    50                  55                  60

Val Thr Arg Phe Asp Phe Thr Thr Thr Ser Thr Ser Thr Ala Val Pro
65                  70                  75                  80

Pro Pro Thr Asp Leu Arg Phe Thr Asn Ile Gly Pro Asp Thr Met Arg
                85                  90                  95

Val Thr Trp Ala Pro Pro Pro Ser Ile Asp Leu Thr Asn Phe Leu Val
            100                 105                 110

Arg Tyr Ser Pro Val Lys Asn Glu Glu Asp Val Ala Glu Leu Ser Ile
        115                 120                 125

Ser Pro Ser Asp Asn Ala Val Val Leu Thr Asn Leu Leu Pro Gly Thr
    130                 135                 140

Glu Tyr Val Val Ser Val Ser Ser Val Tyr Gly Arg Gly Asp Ser Pro
145                 150                 155                 160

Ala Ser Ser Thr Pro Leu Arg Gly Arg Gln Lys Thr
                165                 170
```

<210> SEQ ID NO 10
<211> LENGTH: 522
<212> TYPE: DNA
<213> ORGANISM: artificial
<220> FEATURE:
<223> OTHER INFORMATION: FNIII1H, 8RGD

<400> SEQUENCE: 10

```
atccagtgga atgcaccaca gccatctcac atttccaagt acattctcag gtggagacct     60

aaaaattctg taggccgttg gaaggaagct accataccag gccacttaaa ctcctacacc    120

atcaaaggcc tgaagcctgg tgtggtatac gagggccagc tcatatcgat tcagcagtac    180

ggccaccaag aagtgactcg ctttgacttc accaccacca gcaccagcac aggatctgct    240

gttcctcctc ccactgacct gcgattcacc aacattggtc cagacaccat gcgtgtcacc    300

tgggctccac ccccatccat tgatttaacc aacttcctgg tgcgttactc acctgtgaaa    360

aatgaggaag atgttgcaga gttgtcaatt tctccttcag acaatgcagt ggtcttaaca    420

aatctcctgc ctggtacaga atatgtagtg agtgtctcca gtgtctacgg ccgtggagac    480

tcgccggcaa gcagcacacc tcttagagga agacagaaaa ca                       522
```

<210> SEQ ID NO 11
<211> LENGTH: 516
<212> TYPE: DNA
<213> ORGANISM: artificial
<220> FEATURE:
<223> OTHER INFORMATION: FNIII1H, 8 RGD

<400> SEQUENCE: 11

```
atccagtgga atgcaccaca gccatctcac atttccaagt acattctcag gtggagacct     60
aaaaattctg taggccgttg gaaggaagct accataccag gccacttaaa ctcctacacc    120
atcaaaggcc tgaagcctgg tgtggtatac gagggccagc tcatcagcat ccagcagtac    180
ggccaccaag aagtgactcg ctttgacttc accaccacca gcaccagcac agctgttcct    240
cctcccactg acctgcgatt caccaacatt ggtccagaca ccatgcgtgt cacctgggct    300
ccacccccat ccattgattt aaccaacttc ctggtgcgtt actcacctgt gaaaaatgag    360
gaagatgttg cagagttgtc aatttctcct tcagacaatg cagtggtctt aacaaatctc    420
ctgcctggta cagaatatgt agtgagtgtc tccagtgtct acggccgtgg agactcgccg    480
gcaagcagca cacctcttag aggaagacag aaaaca                              516
```

<210> SEQ ID NO 12
<211> LENGTH: 5
<212> TYPE: PRT
<213> ORGANISM: artificial
<220> FEATURE:
<223> OTHER INFORMATION: heparin binding sequence
<220> FEATURE:
<221> NAME/KEY: MISC_FEATURE
<222> LOCATION: (1)..(1)
<223> OTHER INFORMATION: Xaa is a charged amino acid
<220> FEATURE:
<221> NAME/KEY: MISC_FEATURE
<222> LOCATION: (3)..(3)
<223> OTHER INFORMATION: Xaa is a charged amino acid
<220> FEATURE:
<221> NAME/KEY: MISC_FEATURE
<222> LOCATION: (5)..(5)
<223> OTHER INFORMATION: Xaa is a charged amino acid

<400> SEQUENCE: 12

```
Xaa Trp Xaa Pro Xaa
1               5
```

<210> SEQ ID NO 13
<211> LENGTH: 5
<212> TYPE: PRT
<213> ORGANISM: artificial
<220> FEATURE:
<223> OTHER INFORMATION: heparin binding sequence

<400> SEQUENCE: 13

```
Arg Trp Arg Pro Lys
1               5
```

<210> SEQ ID NO 14
<211> LENGTH: 7
<212> TYPE: PRT
<213> ORGANISM: artificial
<220> FEATURE:
<223> OTHER INFORMATION: RGD sequence

<400> SEQUENCE: 14

```
Arg Gly Asp Ser Pro Ala Ser
1               5
```

<210> SEQ ID NO 15
<211> LENGTH: 4
<212> TYPE: PRT
<213> ORGANISM: artificial
<220> FEATURE:
<223> OTHER INFORMATION: RGD sequence

<400> SEQUENCE: 15

Gly Arg Gly Asp
1

<210> SEQ ID NO 16
<211> LENGTH: 5
<212> TYPE: PRT
<213> ORGANISM: artificial
<220> FEATURE:
<223> OTHER INFORMATION: RGD sequence

<400> SEQUENCE: 16

Gly Arg Gly Asp Ser
1 5

<210> SEQ ID NO 17
<211> LENGTH: 7
<212> TYPE: PRT
<213> ORGANISM: artificial
<220> FEATURE:
<223> OTHER INFORMATION: RGD sequence

<400> SEQUENCE: 17

Gly Arg Gly Asp Ser Pro Lys
1 5

<210> SEQ ID NO 18
<211> LENGTH: 6
<212> TYPE: PRT
<213> ORGANISM: artificial
<220> FEATURE:
<223> OTHER INFORMATION: RGD sequence

<400> SEQUENCE: 18

Gly Arg Gly Asp Thr Pro
1 5

<210> SEQ ID NO 19
<211> LENGTH: 9
<212> TYPE: PRT
<213> ORGANISM: artificial
<220> FEATURE:
<223> OTHER INFORMATION: RGD sequence

<400> SEQUENCE: 19

Ser Asp Gly Arg Gly Arg Gly Asp Ser
1 5

<210> SEQ ID NO 20
<211> LENGTH: 4
<212> TYPE: PRT
<213> ORGANISM: artificial
<220> FEATURE:
<223> OTHER INFORMATION: RGD sequence

<400> SEQUENCE: 20

Arg Gly Asp Ser
1

<210> SEQ ID NO 21
<211> LENGTH: 10
<212> TYPE: PRT
<213> ORGANISM: artificial
<220> FEATURE:
<223> OTHER INFORMATION: RGD sequence

<400> SEQUENCE: 21

Arg Gly Asp Ser Pro Ala Ser Ser Lys Pro
1 5 10

<210> SEQ ID NO 22
<211> LENGTH: 11
<212> TYPE: PRT
<213> ORGANISM: artificial
<220> FEATURE:
<223> OTHER INFORMATION: RGD sequence

<400> SEQUENCE: 22

Arg Arg Arg Arg Arg Arg Gly Asp Ser Pro Lys
1 5 10

<210> SEQ ID NO 23
<211> LENGTH: 10
<212> TYPE: PRT
<213> ORGANISM: artificial
<220> FEATURE:
<223> OTHER INFORMATION: RGD sequence
<220> FEATURE:
<221> NAME/KEY: MISC_FEATURE
<222> LOCATION: (2)..(2)
<223> OTHER INFORMATION: Xaa is D-arginine

<400> SEQUENCE: 23

Gly Xaa Gly Asp Ser Pro Ala Ser Ser Lys
1 5 10

<210> SEQ ID NO 24
<211> LENGTH: 6
<212> TYPE: PRT
<213> ORGANISM: artificial
<220> FEATURE:
<223> OTHER INFORMATION: RGD peptide

<400> SEQUENCE: 24

Gly Arg Gly Asp Ser Pro
1 5

<210> SEQ ID NO 25
<211> LENGTH: 30
<212> TYPE: DNA
<213> ORGANISM: artificial
<220> FEATURE:
<223> OTHER INFORMATION: primer

<400> SEQUENCE: 25
cccagatctc tgaggtggac cccgctaaac 30

<210> SEQ ID NO 26
<211> LENGTH: 35
<212> TYPE: DNA
<213> ORGANISM: artificial
<220> FEATURE:
<223> OTHER INFORMATION: primer

<400> SEQUENCE: 26
ccccccgggc tatgttcggt aattaatgga aattg 35

<210> SEQ ID NO 27
<211> LENGTH: 84
<212> TYPE: DNA
<213> ORGANISM: artificial
<220> FEATURE:
<223> OTHER INFORMATION: primer

<400> SEQUENCE: 27
cccggtacca tccagtggaa tgcaccacag ccatctcaca tttccaagta cattctcacg 60
tggacacctg caaattctgt aggc 84

<210> SEQ ID NO 28
<211> LENGTH: 31
<212> TYPE: DNA
<213> ORGANISM: artificial
<220> FEATURE:
<223> OTHER INFORMATION: primer

<400> SEQUENCE: 28
cccgaattcc tatgtgctgg tgctggtggt g 31

<210> SEQ ID NO 29
<211> LENGTH: 38
<212> TYPE: DNA
<213> ORGANISM: artificial
<220> FEATURE:
<223> OTHER INFORMATION: primer

<400> SEQUENCE: 29
ggtatacgac ggcaacctga tcagcatcca gcactacg 38

<210> SEQ ID NO 30
<211> LENGTH: 35
<212> TYPE: DNA
<213> ORGANISM: artificial
<220> FEATURE:
<223> OTHER INFORMATION: primer

<400> SEQUENCE: 30
ccccccgggc tatgttcggt aattaatgga aattg 35

<210> SEQ ID NO 31
<211> LENGTH: 30
<212> TYPE: DNA
<213> ORGANISM: artificial
<220> FEATURE:
<223> OTHER INFORMATION: primer

<400> SEQUENCE: 31
cccggatcca tccagtggaa tgcaccacag 30

<210> SEQ ID NO 32
<211> LENGTH: 41
<212> TYPE: DNA
<213> ORGANISM: artificial
<220> FEATURE:
<223> OTHER INFORMATION: primer

<400> SEQUENCE: 32
gtcacgatca attcccgggc tatgttttct gtcttcctct a 41

<210> SEQ ID NO 33
<211> LENGTH: 46
<212> TYPE: DNA
<213> ORGANISM: artificial
<220> FEATURE:
<223> OTHER INFORMATION: primer

<400> SEQUENCE: 33
ggtccctcgg aacatcagaa actgttttct gtcttcctct aagagg 46

<210> SEQ ID NO 34
<211> LENGTH: 42
<212> TYPE: DNA
<213> ORGANISM: artificial
<220> FEATURE:
<223> OTHER INFORMATION: primer

<400> SEQUENCE: 34
ccaggtccct cggaacatca gaaactgtgc tggtgctggt gg 42

<210> SEQ ID NO 35
<211> LENGTH: 39
<212> TYPE: DNA
<213> ORGANISM: Artificial Sequence
<220> FEATURE:
<223> OTHER INFORMATION: primer

<400> SEQUENCE: 35
ggtatacgag ggccagctca tatcgatcca gcagtacgg 39

<210> SEQ ID NO 36
<211> LENGTH: 90
<212> TYPE: DNA
<213> ORGANISM: Artificial Sequence
<220> FEATURE:
<223> OTHER INFORMATION: primer

<400> SEQUENCE: 36
catatcgatc cagcagtacg gccaccaaga agtgactcgc tttgacttca ccaccaccag 60
caccagcaca ggtcttgatt ccccaactgg 90

<210> SEQ ID NO 37
<211> LENGTH: 85
<212> TYPE: DNA
<213> ORGANISM: artificial
<220> FEATURE:
<223> OTHER INFORMATION: primer

<400> SEQUENCE: 37
gtgagtgtct ccagtgtcta cggccgtgga gactcgccgg caagcagcac acctcttaga 60
ggaagacaga aaacatagga attca 85

<210> SEQ ID NO 38
<211> LENGTH: 8
<212> TYPE: PRT
<213> ORGANISM: artificial
<220> FEATURE:
<223> OTHER INFORMATION: RGD sequence

<400> SEQUENCE: 38

Gly Arg Gly Asp Ser Pro Ala Ser
1 5

<210> SEQ ID NO 39
<211> LENGTH: 41
<212> TYPE: DNA
<213> ORGANISM: artificial
<220> FEATURE:
<223> OTHER INFORMATION: primer

<400> SEQUENCE: 39
ggtatacgag ggccagctca tatcgattca gcagtacggc c 41

-continued

```
<210> SEQ ID NO 40
<211> LENGTH: 33
<212> TYPE: DNA
<213> ORGANISM: artificial
<220> FEATURE:
<223> OTHER INFORMATION: primer

<400> SEQUENCE: 40

cggatccgct gttcctcctc ccactgacct gcg                    33


<210> SEQ ID NO 41
<211> LENGTH: 25
<212> TYPE: DNA
<213> ORGANISM: artificial
<220> FEATURE:
<223> OTHER INFORMATION: primer

<400> SEQUENCE: 41

cgaattccta tgttttctgt cttcc                             25
```